US011229728B1

(12) United States Patent
Barneck et al.

(10) Patent No.: US 11,229,728 B1
(45) Date of Patent: *Jan. 25, 2022

(54) METHOD AND APPARATUS TO DELIVER THERAPEUTIC, NON-ULTRAVIOLET ELECTROMAGNETIC RADIATION IN A DIALYSIS SYSTEM

(71) Applicant: LIGHT LINE MEDICAL, INC., Salt Lake City, UT (US)

(72) Inventors: Mitchell D. Barneck, Orlando, FL (US); Nathaniel L. R. Rhodes, Salt Lake City, UT (US); James P. Allen, Maple Grove, MN (US); Curtis D. Long, Cottonwood Heights, UT (US); Perry Croll, Sandy, UT (US)

(73) Assignee: Light Line Medical, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/000,736

(22) Filed: Aug. 24, 2020

(51) Int. Cl.
*A61M 1/28* (2006.01)
*A61N 5/06* (2006.01)

(52) U.S. Cl.
CPC .......... *A61M 1/285* (2013.01); *A61N 5/0601* (2013.01); *A61N 5/0624* (2013.01); *A61M 2205/051* (2013.01); *A61N 2005/063* (2013.01)

(58) Field of Classification Search
CPC ............ A61M 1/285; A61M 2205/051; A61N 5/0601; A61N 5/0624; A61N 2005/063; A61N 5/06–2005/073
See application file for complete search history.

(56) References Cited

U.S. PATENT DOCUMENTS

| | | | |
|---|---|---|---|
| 4,412,834 A | 11/1983 | Kulin et al. |
| 4,512,762 A | 4/1985 | Spears |
| 5,053,003 A | 10/1991 | Dadson et al. |
| 5,260,020 A | 11/1993 | Wilk et al. |
| 5,445,608 A | 8/1995 | Chen et al. |
| 5,607,419 A | 3/1997 | Amplatz et al. |
| 5,637,877 A | 6/1997 | Sinofsky |
| 5,695,482 A | 12/1997 | Kaidany |
| 5,702,432 A | 12/1997 | Chen et al. |

(Continued)

FOREIGN PATENT DOCUMENTS

| | | |
|---|---|---|
| WO | WO2006/074509 | 7/2006 |
| WO | WO2019/027478 | 2/2019 |

*Primary Examiner* — Jonathan T Kuo
(74) *Attorney, Agent, or Firm* — Madson IP, P.C.

(57) ABSTRACT

Methods and apparatus provide therapeutic electromagnetic radiation (EMR) for inactivating infectious agents in, on or around a catheter residing in a patient's body cavity and/or for enhancing healthy cell growth. Transmitting non-ultraviolet therapeutic EMR substantially axially along an optical element in a lumen of the catheter body and/or the catheter body. Through delivery of the therapeutic EMR to particular infected areas and/or areas requiring tissue healing. The inactivation of the major sources of infection in, on, and around catheters and/or enhance healthy cell growth around catheters is accomplished by utilizing controlled relative intensity and/or treatment region specific dosing of the therapeutic EMR emitted radially from the optical element. Specific embodiments of urinary catheters, peritoneal dialysis catheters, dialysis accesses, and hemodialysis accesses are also disclosed.

20 Claims, 32 Drawing Sheets

(56) References Cited

U.S. PATENT DOCUMENTS

| | | | |
|---|---|---|---|
| 5,855,203 A | 1/1999 | Matter | |
| 6,119,037 A | 9/2000 | Kellogg et al. | |
| 6,461,569 B1 | 10/2002 | Boudreaux | |
| 6,551,346 B2 | 1/2003 | Crossley | |
| 6,562,295 B1 | 5/2003 | Neuberger | |
| 7,232,429 B2 | 6/2007 | Moreci | |
| 7,449,026 B2 | 11/2008 | Zalesky | |
| 7,730,894 B2 | 6/2010 | Bishop et al. | |
| 8,057,464 B2 | 11/2011 | Chen et al. | |
| 8,933,416 B2 | 1/2015 | Arcand et al. | |
| 9,039,966 B2 | 5/2015 | Anderson et al. | |
| 9,808,647 B2 * | 11/2017 | Rhodes | A61N 5/0624 |
| 10,307,612 B2 * | 6/2019 | Barneck | A61L 2/084 |
| 2003/0018324 A1 | 1/2003 | Davenport et al. | |
| 2004/0039242 A1 | 2/2004 | Tolkoff et al. | |
| 2004/0193218 A1 | 9/2004 | Butler | |
| 2005/0090722 A1 | 4/2005 | Perez | |
| 2006/0009821 A1 | 1/2006 | Perez | |
| 2007/0219605 A1 | 9/2007 | Yaroslavsky et al. | |
| 2007/0260295 A1 | 11/2007 | Chen et al. | |
| 2008/0051736 A1 | 2/2008 | Rioux et al. | |
| 2008/0159908 A1 | 7/2008 | Redmond | |
| 2008/0306454 A1 | 12/2008 | Sikora | |
| 2009/0048648 A1 | 2/2009 | Dacey, Jr. et al. | |
| 2009/0257910 A1 | 10/2009 | Segal | |
| 2010/0072399 A1 | 3/2010 | Latham et al. | |
| 2010/0246169 A1 | 9/2010 | Anderson et al. | |
| 2010/0256607 A1 | 10/2010 | Burnett | |
| 2011/0085936 A1 | 4/2011 | Deutsch et al. | |
| 2011/0208274 A1 | 8/2011 | Bornstein | |
| 2011/0295343 A1 | 12/2011 | Bornstein et al. | |
| 2012/0321509 A1 | 12/2012 | Bak | |
| 2013/0030249 A1 | 1/2013 | Vazales et al. | |
| 2013/0060188 A1 | 3/2013 | Bedwell et al. | |
| 2013/0267888 A1 | 10/2013 | Rhodes et al. | |
| 2013/0303996 A1 | 11/2013 | Rasooly et al. | |
| 2014/0058253 A1 | 2/2014 | Prough et al. | |
| 2014/0150782 A1 | 6/2014 | Vazales et al. | |
| 2014/0235942 A1 | 8/2014 | Hellstrom et al. | |
| 2015/0057648 A1 | 2/2015 | Swift et al. | |
| 2015/0231287 A1 | 8/2015 | Lin et al. | |
| 2015/0297767 A1 | 10/2015 | Gaska et al. | |
| 2015/0343182 A1 | 12/2015 | Vazales et al. | |
| 2016/0151639 A1 | 6/2016 | Scharf et al. | |
| 2016/0256646 A1 | 9/2016 | Vazales | |
| 2016/0279402 A1 | 9/2016 | Stigall et al. | |
| 2016/0317832 A1 | 11/2016 | Barneck et al. | |
| 2018/0015302 A1 | 1/2018 | Barneck et al. | |
| 2018/0178029 A1 | 6/2018 | Rogers et al. | |
| 2019/0217117 A1 * | 7/2019 | Barneck | A61N 5/0601 |
| 2019/0358387 A1 | 11/2019 | Elbadry et al. | |

\* cited by examiner

METHOD AND APPARATUS TO DELIVER THERAPEUTIC, NON-ULTRAVIOLET ELECTROMAGNETIC RADIATION IN A DIALYSIS SYSTEM

RELATED APPLICATIONS

This application is a continuation-in-part of U.S. patent application Ser. No. 16/364,051, filed on Mar. 25, 2019 and entitled METHODS AND APPARATUS TO DELIVER THERAPEUTIC, NON-ULTRAVIOLET ELECTROMAGNETIC RADIATION VERSATILELY VIA A CATHETER RESIDING IN A BODY CAVITY (hereinafter the "Parent Application"), which is a continuation-in-part of U.S. patent application Ser. No. 15/668,266, filed on Aug. 3, 2017 and entitled METHODS AND APPARATUS TO DELIVER THERAPEUTIC, NON-ULTRAVIOLET ELECTROMAGNETIC RADIATION TO INACTIVATE INFECTIOUS AGENTS AND/OR TO ENHANCE HEALTHY CELL GROWTH VIA A CATHETER RESIDING IN A BODY CAVITY (hereinafter the "Grandparent Application"), which is a continuation-in-part of U.S. patent application Ser. No. 13/801,750, filed on Mar. 13, 2013 and entitled METHODS AND APPARATUS TO INACTIVATE INFECTIOUS AGENTS ON A CATHETER RESIDING IN A BODY CAVITY (hereinafter the "Great-Grandparent Application"), now issued as U.S. Pat. No. 9,808,647 on Nov. 7, 2017, which claimed the benefit of U.S. Provisional Application No. 61/686,432 filed Apr. 5, 2012 and was entitled HINS LASER LIGHT CATHETER. The Grandparent Application is also a continuation-in-part of U.S. application Ser. No. 15/424,732, filed Feb. 3, 2017 and entitled METHOD AND APPARATUS FOR REMOVABLE CATHETER VISUAL LIGHT THERAPEUTIC SYSTEM, now issued as U.S. Pat. No. 10,543,338 on Jan. 28, 2020, which claims the benefit of U.S. Provisional Application No. 62/292,028 that was filed Feb. 5, 2016, for an invention titled METHOD AND APPARATUS FOR REMOVABLE CATHETER VISUAL LIGHT STERILIZATION SYSTEM. Each of the related applications mentioned in this paragraph is hereby incorporated by this reference as if fully set forth herein.

TECHNICAL FIELD

The present invention is a method and apparatus to provide versatile delivery of therapeutic doses of non-ultraviolet light to inactivate infectious agents residing on, within, or generally around a catheter while the catheter is residing within a body cavity or residing on, within, or around extension catheters and connectors outside the body along the flow path of dialysate and waste dialysate, to stimulate healthy cell growth within the body and at the entry/exit site causing a healing effect. Such versatile delivery of therapeutic doses of non-ultraviolet light may employ controlled relative intensity and/or treatment region specific application of the therapeutic doses. In particular, this disclosure is of a medical device assembly that utilizes non-ultraviolet visual therapeutic electromagnetic radiation (EMR) at a high enough intensity to stimulate healthy cell growth causing a healing effect and/or to reduce or eliminate infectious agents in, on, and around a catheter while the catheter resides inside a body cavity and/or in, on, and around the extension catheters and connectors outside the body along the flow path of dialysate and waste dialysate.

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "some embodiments," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

BACKGROUND

Catheters are commonly used as channels to inject medications into or retrieve fluid samples from a patient. Each catheter comprises a tube, usually derived from plastic or other polymers, such as silicone, polyurethane, and the like, that is inserted into an area of the body and may contain one or more separate lines in which these fluids may be delivered or retrieved. A "lumen" designates a pathway in the catheter that goes from outside the body to inside the body. Catheters are used in various applications, including intravascularly, abdominally, urologically, gastrointestinally, ophthalmically, within the respiratory tract, within cranial space, within the spinal column, during dialysis and the like. In all cases, the catheter extends from outside the body to be placed inside of a space in the body where the catheter resides, herein referred to as a "body cavity". These devices frequently give rise to infections caused by growth of infectious agents in, on, and around the catheter and on tissue surrounding the catheter. Infectious agents can include bacteria, fungi, viruses, or the like that enter the body and lead to illness of a patient. Depending on the location of the catheter placement, these infections can arise in the form of urinary tract infections, blood stream infections, soft tissue infection, and the like.

Catheter related infections (CRIs) are a large problem in medicine, leading to high morbidity and mortality rates. Current methods of reducing or eliminating the number of infectious agents in, on, around a catheter are of low efficacy. Typically, catheters will be removed if they are suspected to be harboring infectious agents, increasing both the cost associated with treatment and patient discomfort. Various methods to deter or eliminate growth of infectious agents in, on, and around catheters have been attempted, such as using sterile handling techniques, antibiotics, and replacing the catheter when an infection is suspected. Despite these techniques, infections resulting from catheters remain a major problem. According to the Centers for Disease Control and Prevention, over 31,000 people died specifically from catheter-related bloodstream infections in 2010. These infections, along with urinary tract infections, gastrointestinal infections, and other infections from catheters, increase both medical costs and patient discomfort.

Catheters come in various sizes. Those that are smaller in diameter, such as many PICC lines (peripherally inserted central catheters), have small diameter lumens. Such smaller diameter catheters may be suitable for prolonged insertion. Consequently, with smaller diameter catheters, there may be inadequate thickness to the catheter wall to carry a sterilization and/or healthy growth enhancing delivery system.

The use of ultraviolet (UV) light, disinfecting chemicals, catheters impregnated with drugs, to name a few, have been attempted to reduce the prevalence of infection. Many patents have attempted to utilize UV light to disinfect catheters. Unfortunately, UV light is well known to cause damage to living cells. Methods to disinfect connectors, stopcocks, and valves using sterilizing electromagnetic radiation (EMR) have also been attempted using 405 nm light to sterilize these points, but these methods neglect disinfection of the catheter body as well as the tip of the catheter.

The emergence of infectious agents that are resistant to current treatments, such as methicillin-resistance *Staphylococcus aureus* (MRSA), further substantiate the need for another treatment of CRIs. To reduce the costs associated with having to remove and replace the catheters from the patient, there is a need for a catheter that can be sterilized while residing in the patient. Additionally, it would be advantageous to be able to stimulate healthy cell growth by providing therapeutic EMR via the indwelling catheter.

Immediate disinfection after placement could help prevent the growth of biofilm on the catheter. Biofilm consists of extracellular polymeric material created by microorganisms after they adhere to a surface. This biofilm facilitates the growth of infectious agents and is very difficult to break down once it has begun to grow.

The growth of infectious agents can result from agents outside the patient (at the point of access as the catheter crosses the skin or from the catheter hub) or from inside the patient, wherein infectious agents already in the body attach to the surface of the catheter and proliferate. Scientific literature suggests that approximately 65% of CRI's come from infectious agents residing on the skin of the patient (S. Öncü, Central Venous Catheter—Related Infections: An Overview with Special Emphasis on Diagnosis, Prevention and Management. The Internet Journal of Anesthesiology. 2003 Volume 7 Number 1). These agents travel down the outside of the catheter and colonize the catheter tip. For short term catheterization, this is believed to be the most likely mechanism of infection (Crump. Intravascular Catheter-Associated Infections. Eur J Clin Microbiol Dis (2000) 19:1-8). Thirty percent (30%) of CRIs are believed to come from a contaminated hub, in which infectious agents travel down the interior of the catheter (Öncü). This is believed to be the most likely mechanism of infection for long-term catheterization (Crump).

EMR in the range of 380-900 nm has been shown to be effective in killing infectious agents. Research done by a group at the University of Strathclyde shows that light in this range is effective in killing surface bacteria in burn wards without harming the patients (Environmental decontamination of a hospital isolation room using high-intensity light. J Hosp Infect. 2010 November; 76(3):247-51). Published patent application 2010/0246169, written by the members who conducted the study, utilizes ambient lighting to disinfect a large surrounding area. The mechanism proposed by the team suggests that light in this range leads to photosensitization of endogenous porphyrins within the bacteria, which causes the creation of singlet oxygen, leading to the death of the bacteria. (Inactivation of Bacterial Pathogens following Exposure to Light from a 405-Nanometer Light-Emitting Diode Array. Appl Environ Microbiol. 2009 April; 75(7):1932-7).

Heretofore, however, there has never been apparatus or methods for making or using such apparatus to safely and effectively disinfect a catheter while it is still implanted in a patient. Accordingly, there exists a need for a methods and apparatus designed to deliver non-antibiotic, bactericidal therapeutics in-vivo. Such methods and apparatus, using novel technology, may provide removable delivery of safe, effective, and reproducible disinfection and/or enhance healthy cell growth.

SUMMARY OF THE INVENTION

The exemplary embodiments of this disclosure relate to medical device assemblies for insertion into a cavity of a patient's body and for delivery from outside the body to inside the body and retrieval of fluids from inside the body to outside the body. Each assembly comprises an electromagnetic radiation (EMR) source for providing non-ultraviolet, therapeutic EMR having intensity sufficient to inactivate one or more infectious agents and/or to enhance healthy cell growth. Each assembly either comprises a catheter or may be used with a catheter having an elongate catheter body with at least one internal lumen, a coupling end, and a distal end. This distal end is insertable into the cavity of the patient's body whether the cavity is venous, arterial, gastrointestinal, abdominal, urological, respiratory, cranial, spinal, or the like, wherein the indwelling catheter body directs both the fluid and the propagation of the therapeutic EMR axially relative to the catheter body for radial delivery into a catheter extension or the catheter, into the patient's body and/or at the distal end. Also, when appropriate, the therapeutic EMR may be directed at or into catheter extensions and connectors outside the body at or into the insertion area. An optical element disposed within a lumen of the catheter body and/or within the catheter body acts conducive to the axial propagation of the therapeutic EMR relative to the catheter body. The optical element or another optical element also may be disposed to act conducive to propagation of therapeutic EMR through at least one coupling element to connect the EMR component to the insertable catheter component.

For the purposes of this disclosure the use of the term "therapeutic" should be understood to mean of or relating to the treatment of disease, including reducing or eliminating infectious agents, as well as serving or performed to maintain health, including enhancing healthy cell growth.

For the purpose of this disclosure the use of the phrase "controlled relative intensity" should be understood to be a term of versatility meaning that the delivery of EMR at various desired intensities may be controlled in any of a number of ways such as 1) by using different single fibers; 2) by using different radial-emission gradients; 3) by using multiple differing fibers; and 4) by retro-fitting the fiber type and/or design for tailored use with an existing catheter or catheter extensions. The versatility contemplated by the phrase "controlled relative intensity" is the ability to deliver EMR of the desired/appropriate intensities to desired location(s) at time(s) most effective within the broad range of types and sizes of catheters.

For the purpose of this disclosure the use of the phrase "treatment region specific" should be understood likewise to be a term of versatility meaning that the delivery of EMR at various desired intensities for desired dosing may be delivered to specific treatment regions by utilizing fiber(s) with radial-emission capability compatible with the specific region or regions within the patient's body and/or in, on, or around the catheter or catheter extensions and connectors to be treated by the application of EMR.

The exemplary medical device assembly comprises an EMR source, an EMR conduction system, and at least one coupling to connect the EMR source to the EMR conduction system. The EMR source provides non-ultraviolet, therapeutic EMR having intensity sufficient to inactivate one or more infectious agents and/or to stimulate healthy cell growth causing a healing effect. In at least one exemplary embodiment, the EMR conduction system may be at least partially insertable into and removable from the lumen of an indwelling catheter. Because the EMR conduction system is removably insertable, in yet another exemplary embodiment, a differing, second EMR conduction system (or at least the optical element of a second EMR conduction system) may also be removably insertable such that the two differing EMR conduction systems may be interchangeably insertable into the same lumen of the catheter or into the extended lumen of the catheter and into catheter extension(s).

In some exemplary embodiments, methods and apparatuses are provided for effectively sterilizing a catheter and the area surrounding the catheter while the catheter is disposed in a body cavity. Such medical device assemblies use sterilizing EMR to reduce or eliminate the count of infectious agents in, on, or around the catheter and/or on or in tissue surrounding the catheter while in a body cavity. In other exemplary embodiments, systems (such as dialysis systems) may have catheter extensions (e.g., fluid extension lines) and connectors disposed outside the body for which effective sterilizing thereof enhances the reduction and elimination of infectious agents throughout the system, including in, on, or around the catheter and/or on or in tissue surrounding the catheter while in a body cavity.

The EMR source can be from a single or group of EMR sources including, but not limited to, a light emitting diode, a semiconductor laser, a diode laser, an incandescent (filtered or unfiltered) and a fluorescent (filtered or unfiltered) light source. This EMR source provides non-ultraviolet, therapeutic EMR providing one or more wavelengths in the range of above 380 nm to about 904 nm. In order to provide sufficient inactivation of infectious species and/or stimulation of healthy cell growth, each EMR wavelength should be of a narrow spectrum and centered around one wavelength from the group. The intensity should be sufficient to inactivate one or more infectious agents and/or to stimulate healthy cell growth causing a healing effect. This group includes several wavelengths centered about: 400 nm, 405 nm, 415 nm, 430 nm, 440 nm, 445 nm, 455 nm, 470 nm, 475 nm, 632 nm, 632.8 nm, 640 nm, 650 nm, 660 nm, 670 nm, 680 nm, 780 nm, 808 nm, 830 nm, and 904 nm.

The EMR source may require drivers and electronic support for full functionality. Consideration should be given to accommodating the support hardware and/or software, which may encompass a significant portion of the EMR source's functionality and efficacy. It is possible that the EMR source may generate heat, which could be detrimental to the EMR source and may need to be limited.

This disclosure describes a catheter having an elongate catheter body with at least one internal lumen, a coupling end and a distal end, the distal end being insertable into the cavity of the patient's body. The catheter body is meant to direct both the fluid and the therapeutic EMR axially relative to the catheter body for delivery into the patient's body at the insertion site, along the elongate catheter body, and/or at the distal end. This disclosure includes an optical element disposed within the catheter body and conducive to the axial propagation of the therapeutic EMR through the catheter body. Finally, this disclosure describes at least one coupling element to connect the radiation source to the catheter body. Further, the catheter may be connected to one or more extension catheters (e.g., fluid extension lines) and connectors through which fluid is supplied or retrieved. It may be advantageous to have such extension catheters and connectors also be conducive to the axial propagation of the therapeutic EMR therethrough so that the delivery of therapeutic EMR may enhance the reduction and elimination of infectious agents within the overall system.

The sterilizing EMR is transmitted down a specialized path within the catheter via an optical element conducive to the axial propagation of the light. Various methods could be used to facilitate axial propagation of the light relative to the catheter, including a reflective coating within a line of the catheter, a fiber optic cable, a lens, a waveguide, or the like. The light source can be a light-emitting diode (LED), laser, fiber optic filament, or the like.

One exemplary embodiment of the EMR source and support components is simplified to contain only the EMR source and necessary components. In another exemplary embodiment of the EMR conduction system, a passive heat sink is required to diffuse the heat generated into the surrounding environment. In yet another exemplary embodiment of the EMR source, a heat sink may be coupled to at least one fan to actively dissipate heat generated by the EMR source. In other embodiments, multiple EMR sources connected to separate individual optical elements or a single EMR source capable of connecting to separate individual optical elements and providing EMR of distinctly different intensities and/or wavelengths to separate optical elements may be employed.

Of particular interest to this disclosure is the use of light between 380 nm and about 900 nm wavelengths. Additionally, the intensity and power of the light emitted bear significantly on the inactivation of infectious agents, thus a range of radiant exposures covering 0.1 J/cm$^2$ to 1 kJ/cm$^2$ and a range of powers from 0.005 mW to 1 W, and power density range covering 1 mW/cm$^2$ and 1 W/cm$^2$ are of interest for these exemplary device assemblies and methods. These ranges of wavelengths, power densities, and radiant exposures have been shown to have either antimicrobial effects or positive biological effects on healing tissue. These positive biological effects include reduction of inflammatory cells, increased proliferation of fibroblasts, stimulation of collagen synthesis, angiogenesis inducement and granulation tissue formation.

For each exemplary embodiment described herein, the EMR conduction system and method for disinfection/healing could be utilized in an adjustable or predetermined duty cycle. If treatments begin immediately after sterile procedure was initiated, device related infections may be inhibited. This includes device related biofilm growth.

A treatment may include at least one wavelength of therapeutic EMR that acts as a predominant wavelength selected to sterilize one or more target organisms and selected from the group of wavelengths centered about 400 nm, 405 nm, 415 nm, 430 nm, 440 nm, 445 nm, 455 nm, 470 nm, 475 nm, 660 nm, and 808 nm. Or, a predominant wavelength selected to promote healing and healthy cell growth may be selected from the group of wavelengths centered about 632 nm, 632.8 nm, 640 nm, 650 nm, 660 nm, 670 nm, 680 nm, 780 nm, 808 nm, 830 nm, and 904 nm. Another treatment may include alternating the predominant wavelength between a first predominant wavelength and a second predominant wavelength (differing from the first predominant wavelength) in a selected treatment pattern. Further, sterilizing EMR and EMR that stimulates healthy cell growth may be transmitted alternatingly, simultaneously in tandem or alternatively.

A method for constructing an exemplary medical device assembly for insertion into a cavity of a patient's body and for delivery of a fluid (such as a dialysate, a saline solution, or hemodialysis freshened blood) to or retrieval of a fluid (such as waste dialysate or unfreshened blood) from the patient's body may comprise the steps of: locating an indwelling catheter or providing a catheter having an elongate catheter body with one or more internal lumens, a coupling end and an distal end, the distal end being previously inserted/insertable into the cavity of the patient's body; applying one or more optical elements within one or more lumens of the catheter body (or an extension catheter) and/or within a wall of the catheter body, the optical element being conducive to the axial propagation of therapeutic EMR relative to the catheter body; and coupling at least one EMR source to the EMR conduction system and/or the catheter body (or an extension catheter), the EMR source for providing non-ultraviolet, therapeutic EMR having an intensity sufficient to inactivate one or more infectious agent and/or to enhance healthy cell growth.

In one exemplary embodiment, the device uses a catheter that is inserted into a cavity of a patient's body, wherein said catheter allows both fluid and therapeutic EMR to travel axially relative to the catheter body. The catheter also contains at least one coupling lumen to connect an EMR source that will transmit the therapeutic EMR through the coupling lumen and axially relative to the catheter line. A coupling element in this context will usually refer to a typical hub on the therapeutic EMR source.

In at least one exemplary embodiment, a removably insertable EMR conduction system (i.e., an EMR conduction system that may be partially or fully inserted into a lumen of a catheter and may also be partially or fully extracted from disposition within a lumen of a catheter) may comprise at least one optical element having an elongate body conducive to the axial propagation of the therapeutic EMR through the elongate body. This elongate body may have an exterior surface between a coupling end and a distal end. The exterior surface may have at least one radial emission portion wherein the radial emission facilitates the radial emission of therapeutic EMR from the elongate body proximate each radial emission portion. Again, because the removably insertable EMR conduction system may be fully extracted from within a lumen of the catheter, in another exemplary embodiment, a differing, second removably insertable EMR conduction system (or at least the optical element of a second EMR conduction system) may be interchangeably insertable into the same lumen of the catheter. The second removably insertable EMR conduction system may differ in that it may have at least one radial emission portion that differs from at least one radial emission portion of the interchangeable EMR conduction system.

At least one coupling connects the radiation source to the EMR conduction system and, in some exemplary embodiments, may comprise at least one feature that allows for the coupling to be readily removable from the EMR conduction system. The exemplary coupling may be achieved by utilizing a uniquely designed connection, a pre-manufactured coupling system, or any combination thereof that optimizes the coupling efficiency and utility. Further, such couplings couple the removably insertable EMR conduction system to the EMR source and may comprise more than one coupling with an intermediate section optimized to further the propagation of the EMR. In one exemplary embodiment, the EMR source may be coupled to a patch cable or EMR conduction extending segment, which is then coupled to the formal removably insertable EMR conduction system.

The optical element further may comprise at least one optical feature selected from a group of optical features such as a reflective surface, an optically transmissible material, a lens, a fiber optic filament, and any combination thereof. The optical element also may be capable of transmitting more than one wavelength or intensity EMR, for example, the optical element may comprise one or more elongate bodies, with each elongate body transmitting a different wavelength and/or intensity of EMR. Multiple wavelengths may be transmitted alternatively, simultaneously, one after another or in tandem, or a combination thereof (for example, one constantly on and the other wavelength pulsed). Multiple intensities may be transmitted through the same element simultaneously. Alternating patterns of light treatments may also be transmitted.

The EMR conduction system may be configured to insert, at least partially, into one of any number of catheters, such as by way of example only and not to be limiting: a central venous catheter, a peripheral insertion catheter, a peripheral insertion central catheter, a midline catheter, a jugular catheter, a subclavian catheter, a femoral catheter, a cardiac catheter, a cardiovascular catheter, a urinary Foley catheter (see FIGS. 13 to 15), an intermittent urinary catheter, an endotracheal tube, a dialysis catheter with or without extension catheters connected thereto (whether hemodialysis or peritoneal dialysis (see FIGS. 16A to 23)), a gastrointestinal catheter, a nasogastric tube, a wound drainage catheter, or any similar accessing medical catheter or tube that has been inserted into a patient or is connected to a catheter or tube for the purpose of delivering or retrieving fluids or samples via an inserted catheter.

One exemplary embodiment of the EMR conduction system has an optical element comprising a single, insertable optical fiber. With a single optical fiber, the single fiber may allow light to transmit radially or axially at various sections along its length. For sections where light will transmit radially, the exterior surface of the optical element may be altered to facilitate the radial emission of the EMR. The alteration of the exterior surface may be achieved by chemical etching, physical etching, or electromagnetic ablation through plasma or lasers to create various radial emission portions along the length of the optical fiber. The radial emission portions permit light to emit radially from the optical fiber. Of course, another exemplary embodiment of the EMR conduction system may comprise multiple single, insertable optical fibers, each being of the same length or differing lengths, or inserted partially or fully into a catheter or a catheter extension.

For purposes of this disclosure, light emitted radially means that the light has a radial component. Hence, the light emitted radially may emit perpendicularly and/or obliquely to the central axis of the optical fiber at the axial point of emission.

For embodiments having radial emission sections, the material comprising the optical fiber may be selected from a group of materials comprising optical fibers including plastic, silica, fluoride glass, phosphate glass, chalcogenide glass, and any other suitable material that is capable of axial light propagation and surface alteration to achieve radial emission. In addition, the optical fibers may be single mode, multi-mode, or plastic optical fibers that may have been optimized for alteration using a chemical, physical, or electromagnetic manufacturing alteration process. The optical fibers may also be optimized for alteration post-production.

Yet another exemplary embodiment employs a physical abrasion method of alteration to modify the EMR conduction system comprised of at least one optical fiber. This fiber would be utilized based on its optimal optical response to the physical abrasion process. This process may include, but is not limited to, sanding, media blasting, grinding, buffing, or media blasting at least one section of the optical fiber. The physical abrasion process would also necessarily be optimized in terms of the extent of physical abrasion to optimize the appropriate radial EMR emission or lack thereof. This may be accomplished by adjusting at least one of velocity, acceleration, pressure, modification time, or abrasion material utilized in modifying the optical fiber.

Yet another exemplary embodiment employs microscopic porous structures suspended within the optical fiber to achieve radial transmission of light. These microscopic structures may be positioned within the core and/or core-cladding boundary of the optical fiber. The microscopic structures having a refractive index lower than the region free of microscopic structures. The microscopic structures may be a material added to the optical fiber core or the core-cladding boundary, such as a metal, rubber, glass, or plastic. The microscopic structures may also be the lack of material creating an aberration within the optical fiber core or the core-cladding boundary. For example, the presence of microscopic bubbles in the optical fiber core would create an aberration or imperfection that would alter the materials refractive index, resulting in EMR being emitted radially from the optical fiber.

Another exemplary embodiment may comprise at least one optical fiber with cladding altered to optimize the radial or axial propagation of EMR. For example, the cladding may be altered to at least partially remove or thin the cladding in order to achieve partial radial transmission of EMR. Another example could include an optical fiber with only certain portions containing cladding, the EMR transmitting axially in the clad portions and at least partially axially and radially in the non-clad portions.

Yet another exemplary embodiment achieves uniform radial transmission wherein the radial emission portion of the optical fiber has substantially equivalent intensity over the length of the radial emission portion along the optical fiber. This may be done through chemical etching, physical etching, plasma ablation, or laser ablation in a gradient pattern. By altering at least one of velocity, acceleration, pressure gradients, flow, modification time, or modification material or process, it is possible to achieve radial transmission equivalency throughout each portion or the entire length of the modified optical fiber. During manufacturing, a gradient-provided uniformity also may be achieved through addition of microscopic structures positioned within the core and/or core-cladding boundary in a gradient pattern. Also, radial transmission uniformity achieved through gradient cladding or core features are contemplated for achieving desired radial emission, whether substantially uniform over a portion length or varying as desired.

Still another exemplary embodiment achieves a gradient radial transmission wherein at least one portion of the optical fiber emits EMR radially in a gradient distribution. The gradient distribution may also be accomplished through chemical etching, physical etching, plasma or laser ablation in a uniform or gradient pattern. By altering at least one of velocity, acceleration, pressure gradients, flow, modification time, or modification material or process, it is possible to achieve a gradient radial transmission throughout a portion of the optical fiber. This may also be achieved through addition of microscopic structures positioned within the core and/or core-cladding boundary. Gradient radial transmission enables another exemplary embodiment to exhibit controlled relative intensity that may be uniform over a portion of the length and/or non-uniform and varying as desired.

A further exemplary embodiment of a removably insertable EMR conduction system comprises an optical element such as at least one LED, its associated wiring components, and a scaffold. The LED(s) may emit EMR based on the LED's inherent distribution, or may utilize another optical element, such as a lens or mirror, to focus or diffuse the EMR in the direction of interest. In addition, more than one LED could be arranged in an array to appropriately emit EMR for maximal therapeutic benefit. The LED(s), together with associated wiring components may be permanently or removably attached to the scaffold, which allows for removable insertion of the EMR conduction system into a catheter. The scaffold may be rigid, semi-rigid, malleable, elastic, or flexible, or any combination thereof.

In another exemplary embodiment, a catheter with multiple lumens for fluid injection or retrieval contains one or more separate lumens for transmission of the therapeutic EMR. Each lumen may have a separate proximal catheter hub assembly. These internal lumens converge at a convergence chamber, where individual internal lumens consolidate into a single elongated catheter body while retaining their individual internal paths. Such exemplary device may include use of an optical method for diverting the radiation between the convergence chamber and axially through the designated catheter internal lumen.

Samples retrieved through the distal end are often used to characterize the type of infection. One exemplary embodiment of the disclosure focuses on maintaining axial propagation of the light relative to the catheter and delivering therapeutic light of sufficient intensity to the distal end of the catheter to reduce or eliminate the count of infectious agents residing thereon.

In yet another exemplary embodiment, the medical device assembly aforementioned would be used in a urological setting. The catheter (such as a Foley catheter) would be placed into the urethra and bladder of the urinary tract.

In yet another exemplary embodiment, the medical device assembly aforementioned would be used in a gastrointestinal setting.

In yet another exemplary embodiment, the medical device assembly aforementioned would be used in an intravascular setting.

In yet another exemplary embodiment, the medical device assembly aforementioned would be used within the cranial cavity of a patient.

In yet another exemplary embodiment, the medical device assembly aforementioned would be used within the spinal cavity of a patient.

In still another exemplary embodiment, the medical device assembly aforementioned would be used within an ophthalmic cavity of a patient.

In still another exemplary embodiment, the medical device assembly would be used within a dialysis catheter with or without extension catheter(s) and/or connector(s) (whether hemodialysis or peritoneal dialysis).

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the present disclosure will be described with additional specificity and detail through use of the accompanying drawings in which:

FIG. 8A is an elevation view of an exemplary embodiment of an optical element having no radial emission portion; FIG. 8B is an elevation view of another exemplary embodiment of an optical element having a single radial emission portion disposed over an intermediate segment between the coupling end and the distal end of the optical element having a gradient depicted to emit uniform EMR over the length of the intermediate segment; FIG. 8C is an elevation view of yet another exemplary embodiment of an optical element having a single radial emission portion disposed over substantially the entire distance between the coupling end and the distal end of the optical element having a gradient depicted to emit uniform EMR over the length of the segment; FIG. 8D is an elevation view of still another exemplary embodiment of an optical element having multiple radial emission portions, one disposed over an intermediate segment between the coupling end and the distal end of the optical element, and another proximate the distal end; FIG. 8E is an elevational view of another exemplary embodiment of an optical element having multiple radial emission portions, one being two non-gradient emission bands sandwiching a non-radial emission band, another being an example of varying gradients in an intermediate portion of the optical element, and another being a non-uniform gradient portion near the distal end of the optical element, each being examples of controlled relative intensity.

FIG. 16A is a perspective view of an exemplary two-cuff peritoneal dialysis catheter showing the radial emission extending from a connector hub and a point proximate to and downstream from the peritoneal cuff; FIG. 16B is a perspective view of another exemplary two-cuff peritoneal dialysis catheter showing the radial emission of EMR between a point upstream of the subcutaneous cuff and a point downstream of the peritoneal cuff; and FIG. 16C is a perspective view of yet another exemplary two-cuff peritoneal dialysis catheter showing the radial emission of EMR between the connector hub and a point within a peritoneal dialysis solution region;

Figure 1:
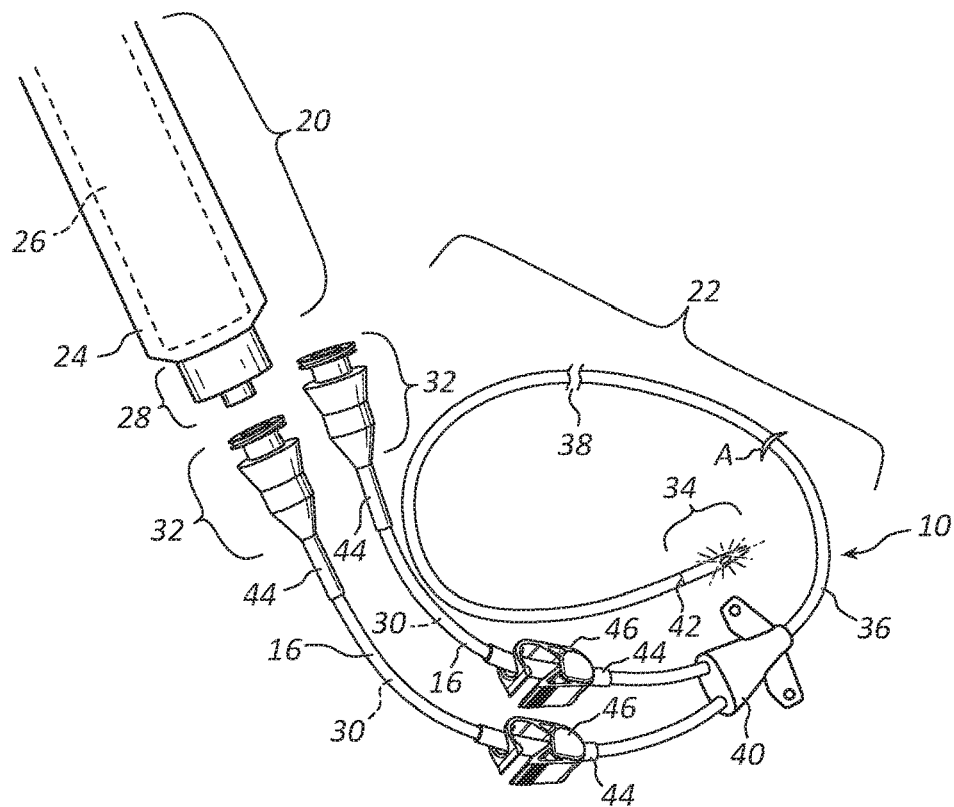
FIG. 1 is a perspective view of an exemplary embodiment of a double lumen catheter and an EMR component with the connection in an exploded view to illustrate the connection of the EMR source to the catheter.

| REFERENCE NUMERALS | |
|---|---|
| catheter 10 | patient's body 12 |
| optical element 14 | line tubing 16 |
| EMR conduction system 18 | electromagnetic radiation component 20 |
| insertable catheter component 22 | elongate body 24 |
| electromagnetic radiation power source 26 | coupling element 28 |
| internal lumen 30 | proximal catheter hub assembly 32 |
| distal end 34 | aperture 35 |
| elongate catheter body 36 | balloon cuff 37 |
| catheter of varying lengths 38 | urethra 39 |
| convergence chamber 40 | bladder 41 |
| termination of the optical element 42 | input port 43 |
| flexible protection tubing 44 | output port 45 |
| line clamp 46 | transdermal area 48 |
| optical assembly 50 | intermediate coupling 52 |
| patch cable 54 | EMR conduction extending segment 56 |
| forward connector 58 | rearward connector 60 |
| exterior surface 62 | distal end 64 |
| core 66 | cladding 68 |
| cladding-encased fiber optic 70 | bare fiber optic 72 |
| inner diameter 74 | outer diameter 76 |
| void 78 | surrounding void 79 |
| core-cladding boundary 80 | cladding outer boundary 82 |
| catheter wall 84 | interior divider walls 85 |
| connecting element 88 | EMR hub connector 90 |
| collimating lens 92 | optical element connector 94 |
| alignment shaft 98 | an aligning bore 99 |
| non-modified optical span 100 | segment-modified optical span 102 |
| radial emission portion 103 | fully-modified optical span 104 |
| elongated radial emission portion 105 | multi-modified optical span 106 |
| modified tip portion 107 | first section 108 |
| microscopic structures free area 109 | second section 110 |
| minimal concentration 111 | third section 112 |
| moderate concentration 113 | fourth section 114 |
| maximal concentration 115 | microscopic structures 117 |
| first dispersal 121 | control device 122 |
| second dispersal 123 | wand 124 |
| third dispersal 125 | acid spray 126 |
| outer region 127 | inner region 129 |
| boundary region 131 | adapter 150 |
| securing sleeve 152 | drain tube 154 |
| control device 155 | operational control features 156 |
| display 158 | optical jack 160 |
| fluid flow/EMR propagation 162 | urine flow 164 |
| meatal region 166 | penis 168 |
| connector hub 170 | peritoneal cuff 172 |
| subcutaneous cuff 174 | coiled Tenckhoff 176 |
| peritoneal dialysis solution region 177 | external segment 178 |
| tunneled segment 180 | exit site location 181 |
| intra-peritoneal segment 182 | extension set interface 184 |
| Y-port adapter 186 | extension line tubing 188 |
| connecting luer 190 | Y-site/transfer region 192 |
| connecting luer/connector hub region 194 | |
| holes 195 | peritoneal dialysis solution 196 |
| peritoneal dialysis system 200 | dialysis access 201 |
| fluid extension line 202 | dialysate exchange switch 204 |
| dialysate supply bag 206 | waste dialysate retrieval bag 208 |
| PD catheter 210 | extension connector 212 |
| extension line portal 214 | dialysate inlet 216 |
| waste dialysate outlet 218 | extension line portal 214 |
| dialysate inlet 216 | waste dialysate outlet 218 |
| exchange selector 220 | feed line 222 |
| peritoneal lining 224 | waste dialysate 226 |
| skin 228 | subcutaneous layer 230 |
| abdominal wall 232 | subcutaneous cuff 234 |

| REFERENCE NUMERALS | |
|---|---|
| deep abdominal wall cuff 236 | introducing adapter 238 |
| drainage line 240 | introducing Y-connector 242 |
| dual introducing Y-connector 244 | line clamp 246 |
| multi-direction adapter 248 | hemodialysis system 300 |
| hemodialysis unit 302 | dialyzer 304 |
| blood pump 306 | dialysate reservoir 308 |
| waste dialysate reservoir 310 | saline bag 312 |
| heparin pump 314 | air trap/air detector 316 |
| arterial-pressure monitor 318 | venous-pressure monitor 320 |
| inflow-pressure monitor 321 | inbound blood flow tubing 322 |
| outbound blood flow tubing 324 | outbound venous line 326 |
| an inbound arterial line 328 | saline line 330 |
| insertion site A | Arrow B |
| Arrows C | Flow Arrows D |
| Inflow Arrow E | Drainage Arrow F |

DETAILED DESCRIPTION

Exemplary embodiments of the present disclosure will be best understood by reference to the drawings, wherein like parts are designated by like numerals throughout. It will be readily understood that the components of the exemplary embodiments, as generally described and illustrated in the Figures herein, could be arranged and designed in a wide variety of different configurations. Thus, the following more detailed description of the exemplary embodiments of the apparatus, system, and method of the present disclosure, as represented in FIGS. 1 through 23, is not intended to limit the scope of the invention, as claimed, but is merely representative of exemplary embodiments.

The phrases "attached to", "secured to", and "mounted to" refer to a form of mechanical coupling that restricts relative translation or rotation between the attached, secured, or mounted objects, respectively. The phrase "slidably attached to" refers to a form of mechanical coupling that permits relative translation, respectively, while restricting other relative motions. The phrase "attached directly to" refers to a form of securement in which the secured items are in direct contact and retained in that state of securement.

The term "abutting" refers to items that are in direct physical contact with each other, although the items may not be attached together. The term "grip" refers to items that are in direct physical contact with one of the items firmly holding the other. The term "integrally formed" refers to a body that is manufactured as a single piece, without requiring the assembly of constituent elements. Multiple elements may be formed integral with each other, when attached directly to each other to form a single work piece. Thus, elements that are "coupled to" each other may be formed together as a single piece.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 2:
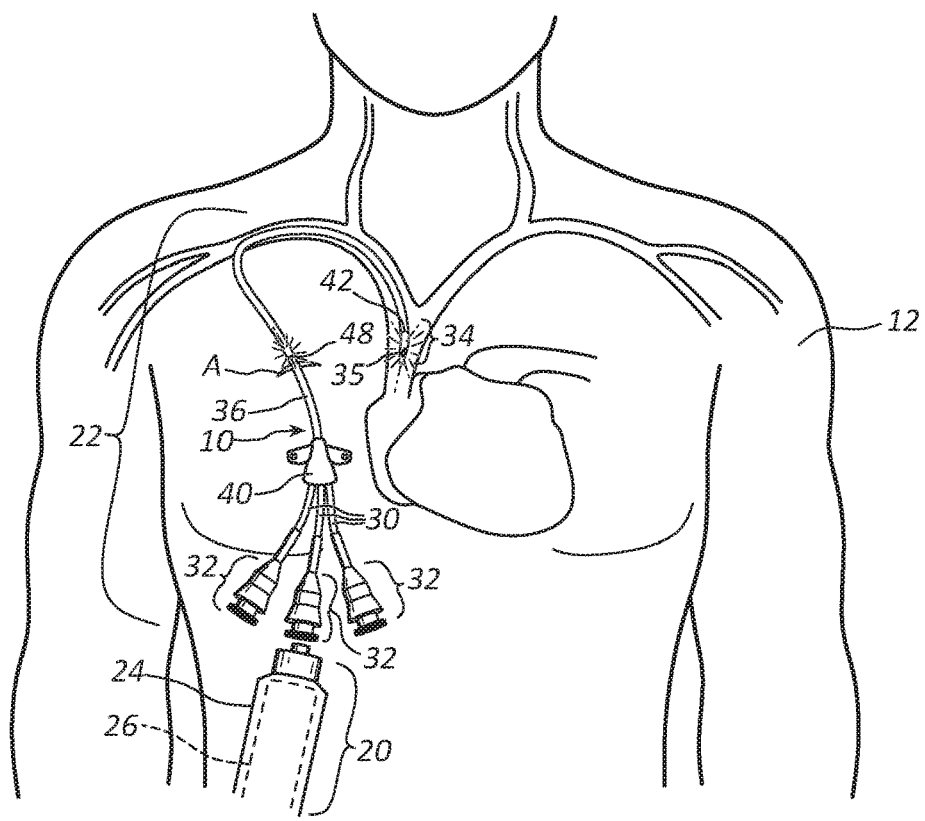
FIG. 2 is a schematic view of another exemplary embodiment of a tunneled triple lumen catheter as inserted into a body cavity through an insert incision in the patient's chest.

Referring now to FIG. 1, a catheter 10 is insertable into a patient's body 12 (see FIG. 2). A medical device assembly of the present disclosure comprises a non-ultraviolet, electromagnetic radiation (EMR) component 20, and an insertable catheter component 22. The non-ultraviolet, EMR component 20 broadly comprises an elongate body 24 used to enclose the EMR power source 26 and a coupling element 28 to couple the two components of the assembly. The EMR used manifests as visible light emitted (as depicted in an exemplary fashion by rays extending radially from the catheter 10) in a range from 380 nm to 904 nm having a high intensity sufficient to create a therapeutic effect such as inactivating one or more infectious agents and/or enhancing healthy cell growth. In some embodiments, the EMR source 26 has adjustability such as an adjustable duty cycle length so that the EMR can be provided with adjustment to an appropriate desired intensity at the most effective times and for beneficial time periods.

The catheters 10 depicted in FIGS. 1-5 are exemplary multiple lumen catheters 10 each of which also comprises line tubing 16, one or more (in FIGS. 1, 4, and 5 two are shown, in FIGS. 2 and 3, three are shown) proximal catheter hub assemblies 32, an elongate catheter body 36, a distal end 34 with one or more apertures 35 that open into internal lumens 30, and a convergence chamber 40. Each internal lumen 30 has an inner diameter (i.e., an interior surface dimension, for example see outer diameter 76 of FIG. 6A) and runs the length of the catheter 10, from the proximal catheter hub assembly 32, through the line tubing 16, the convergence chamber 40, and the elongate catheter body 36, to the distal end 34. Fluids may be injected into the lumen 30 and exit through the aperture 35 into the patient's body 12, or fluids may be drawn from the patient's body 12 through the aperture 35 into the lumen 30. Additionally, some catheters 10 may have inflatable balloon cuffs 37 (see FIGS. 13 and 14) that may seal the catheter 10 against the wall of the patient's body 12 cavity into which the catheter 10 is inserted. The optical element 14 is elongate and may be a reflective coating or it may be a fiber optic with an outer diameter (i.e., an exterior surface dimension, for example see outer diameter 76 of FIG. 6A) sufficiently small to be insertable within at least one of the internal lumens 30 and may extend at least as far into the catheter 10 as a termination of the optical element 42, although the insertion may be less than that length if desired.

Catheters 10 suitable for use with an insertable optical element 14 may be of several different makes, sizes, and functions. For example, a urinary catheter 10 (see FIGS. 13 and 14) inserted through a patient's urethra 39 into a patient's bladder 41 may have an input port 43, an output port 45, and an inflatable balloon cuff 37 to facilitate draining urine from the patient's bladder 41 while permitting fluids (or in the case of the present disclosure therapeutic EMR) to be injected into the patient's body 12. As another example, catheters 10 that are translucent may be particularly suited to permit the passage of radially emitted EMR through the catheter wall 84 (see an exemplary catheter wall 84 in FIGS. 6A-C) to the tissue surrounding the catheter 10. Catheters 10 that have an interior surface dimension (inside diameter 74) sufficiently larger than the exterior surface dimension (outer diameter 76) of the insertable optical element 14 to create a void 78 or passageway (see FIGS. 6A-C) that may permit the injection or withdrawal of fluid (liquid or gas) simultaneously through the catheter 10 while that insertable optical element 14 resides within the catheter 10.

Also, some catheters 10 have radiopacifiers embedded within the walls of the catheter 10 so that an image of where the catheter 10 is located within the patient's body 12 may be determined. However, some catheters 10 have no such radiopacifiers. In either case, it is contemplated by this disclosure that radiopacifiers may be contained in or on the insertable optical element 14 to provide detection of the location of the catheter 10 within the patient's body 12 when the catheter 10 does not have radiopacifiers, and to provide detection of the location of the insertable optical element 14 disposed within the catheter 10 whether or not the catheter 10 has radiopacifiers (this may require differing radiopacifiers in some instances so that the catheter 10 and the insertable optical element 14 may be distinguished).

With some exemplary embodiments, at least one of the proximal catheter hub assemblies 32 may have an optical fiber element alignment shaft 98 that aligns an optical element connector 94 and the insertable optical element 14.

Figure 3:
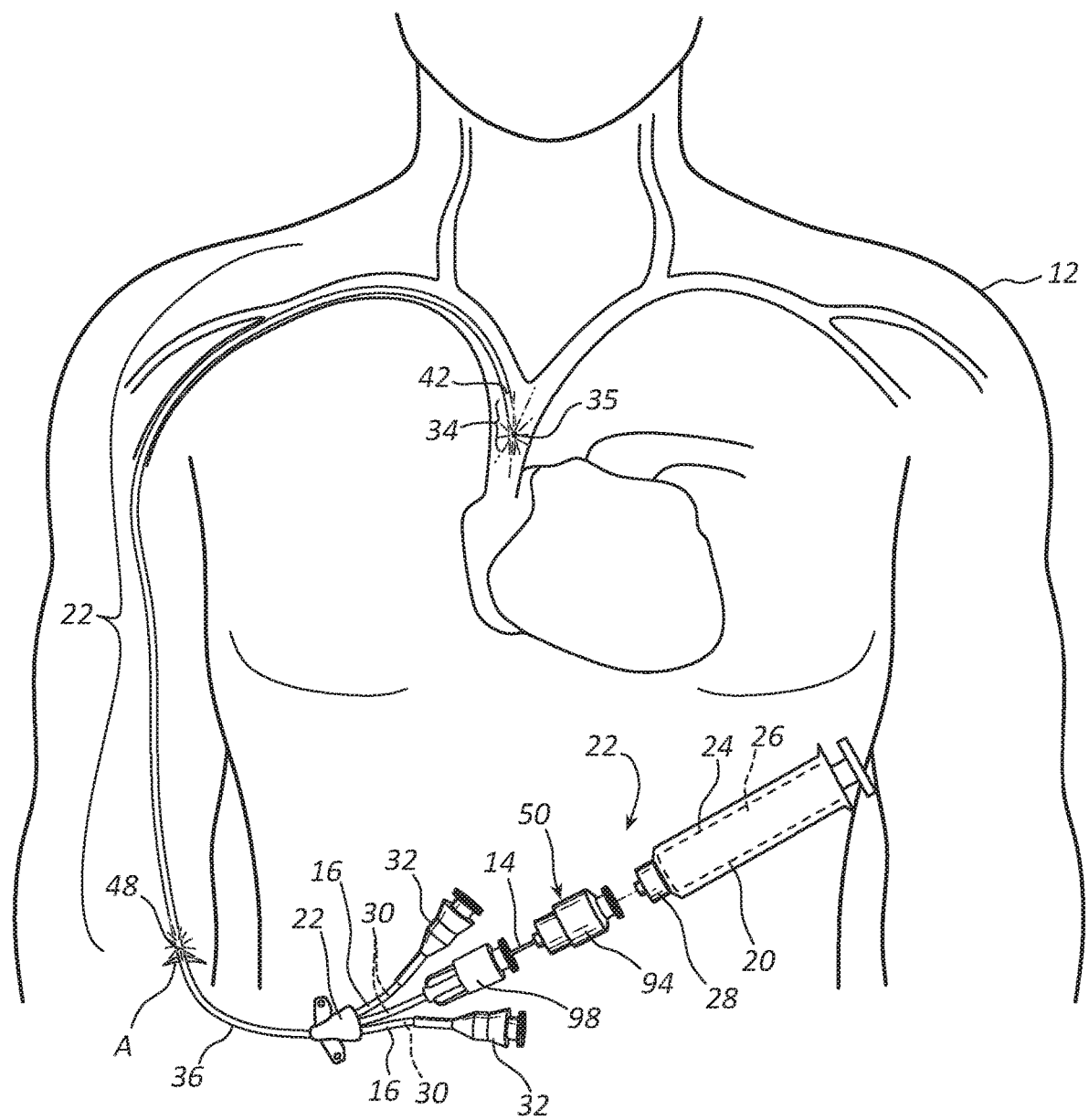
FIG. 3 is a schematic view of yet another exemplary embodiment of a tunneled triple lumen catheter, an insertable optical element, and an EMR component, showing the triple lumen catheter as inserted into a body cavity through an insert incision in the patient's arm and the connection in an exploded view to illustrate the connection of the EMR source to the catheter and the insertion of the optical element partially inserted into the catheter.

FIGS. 2 and 3 show the catheter 10, in a schematic view, inserted at an insertion site A in the chest of the patient's body 12 (FIG. 2) and in an arm of the patient's body 12 (FIG. 3), respectively. The depiction shows how non-ultraviolet, therapeutic EMR may be delivered at the insertion site A and to other sites within the patient's body 12. At the insertion site A, the therapeutic EMR may be delivered to a transdermal area 48 to inactivate infectious agents in that area and to enhance healing of the insert site A. Similarly, proximate the distal end 34, in this case within the vena cava, therapeutic EMR may be delivered to inactivate infectious agents and/or to enhance healing in that proximate vicinity.

Referring specifically to FIG. 2 of the present disclosure, a schematic view of another embodiment of the medical device assembly comprises a non-ultraviolet, EMR component 20, and an insertable catheter component 22. The embodiment shown is specifically a tunneled triple lumen central line variation of the disclosure; however, it should be understood that the catheter 10 may encompass any type of accessing catheter 10 (e.g., vascular, gastrointestinal, etc.) without departing from the scope and spirit of the invention. The non-ultraviolet EMR component 20 is coupled to the proximal catheter hub assembly 32 of the insertable catheter component 22. The other coupling hubs 32 are available for axial propagation of fluid (whether by injection or retrieval). Each designated internal lumen 30 propagates the EMR or fluid between its proximal catheter hub assembly 32 and distal end 34.

Although the triple lumen catheters 10 of FIGS. 2 and 3 depict specific uses of the triple lumen catheter 10, it should be understood that a triple lumen embodiment may be a desirable option in areas where multiple fluid delivery or extraction is necessary simultaneously. For example, in hemodialysis, venous and arterial blood is exchanged simultaneously. Similarly, in peritoneal dialysis, fluids and dissolved substances (electrolytes, urea, glucose, albumin, and other small molecules) are exchanged from the blood by catheter access through peritoneum in the abdomen of a patient. This exemplary triple lumen embodiment allows for the delivery of therapeutic EMR simultaneously with such dialysis function.

The incision site A and the proximate transcutaneous region of the insertable catheter body 36 is often a high source of infections. To reduce infections at the incision site and in the transdermal area 48, a dedicated region of the catheter body 36 may be provided to facilitate radial emission of the therapeutic EMR from the optical element 14 within the elongate catheter body 36. This allows the sterilizing EMR to irradiate outward and inactivate the infectious agents at the insertion site A and the transdermal area 48. By extending the length of the dedicated region towards the distal end 34, a transcutaneous region within the patient's body 12 proximate to the dedicated region may be dosed with therapeutic EMR. Of course, it should be understood that an incision site A could be an entry site and/or an exit site such as used for dialysis (whether peritoneal dialysis or hemodialysis), as will be discussed in more detail later in this disclosure.

Proximate the distal end 34 of the elongate catheter body 36, the optical element 14 discontinues at termination point 42 so that the therapeutic EMR can irradiate throughout the distal end 34 of the catheter 10 and the surrounding cavity area, while not poking or penetrating tissue beyond the distal tip of the catheter 10.

The EMR component 20 comprises the EMR power source 26 (FIGS. 2-5), a light source (not shown, such as a laser or the like), electrical circuitry (not shown), and optics (not shown, but dependent upon the light source) all housed within an elongate body 24. A coupling element 28 connects the EMR component 20 to an optical assembly 50. The optical assembly 50 comprises the insertable optical element 14 and the optical element connector 94. The combination of the EMR component 20, the coupling element 28, and the optical assembly 50, comprising the insertable optical element connector 94 and the insertable optical element 14, will be referred to herein as an EMR conduction system 18. In some embodiments, the EMR conduction system 18 is removable from its inserted disposition within the catheter 10. When the EMR conduction system 18 is removably insertable, therapeutic EMR may be directed into an existing indwelling catheter 10 in a retrofit context. Also, when the EMR conduction system 18 is removably insertable, a differing, second EMR conduction system 18 (or at least the optical element 14 of a second EMR conduction system 18) may also be removably insertable such that the two differing EMR conduction systems 18 may be interchangeably insertable into the same lumen 30 of the catheter 10.

Of particular interest to each of the embodiments is the use of light having wavelengths ranging from above 380 nm and about 904 nm. Additionally, the intensity and power of the light emitted serves to inactivate infectious agents and/or to promote healing. A range of radiant exposures covering 0.1 J/cm$^2$ to 1 kJ/cm$^2$ and a range of powers from 0.005 mW to 1 W, and power density range covering 1 mW/cm$^2$ and 1 W/cm$^2$ are of interest for these exemplary device assemblies and methods. These ranges of wavelengths, power densities, and radiant exposures have been shown to have either antimicrobial effects or positive biological effects on healing tissue. These positive biological effects include reduction of inflammatory cells, increased proliferation of fibroblasts, stimulation of collagen synthesis, angiogenesis inducement and granulation tissue formation.

For each exemplary embodiment described herein, the EMR conduction system 18 and method for disinfecting/healing could be utilized in an adjustable or predetermined duty cycle. If treatments begin immediately after sterile procedure has been initiated or in some instances, if treatments proceed during a sterile procedure, device-related infections may be inhibited or eliminated. This includes device-related biofilm growth.

Additionally, although a wavelength in a range from 380 nm to 904 nm with a sufficient intensity will inactivate one or more infectious agents and/or enhance healthy cell growth, more precise wavelengths may have more particular efficacy against certain infectious agents or for a desired healing purpose. It has been determined that sterilizing EMR of wavelengths including wavelengths centered about 400 nm, 405 nm, 415 nm, 430 nm, 440 nm, 455 m, 470 nm, 475 nm, 660 nm, and 808 nm have particular efficacy. A wavelength selected to promote healing and healthy cell growth may be selected from the group of wavelengths centered about 632 nm, 632.8 nm, 640 nm, 650 nm, 660 nm, 670 nm, 680 nm, 780 nm, 808 nm, 830 nm, and 904 nm.

The insertable catheter component 22 (which may be indwelling), being capable of at least partially being inserted into a cavity of the patient's body 12 to deliver the non-ultraviolet, therapeutic EMR, comprises at least one internal lumen 30, a proximal catheter hub assembly 32, and a distal end 34. An internal lumen 30 being simply defined as the internal path by which fluid and/or EMR may travel. In cases of a single or multi-lumen catheter 10, similar features in the drawings will be labeled with the same number. It should be noted that examples of multi-lumen catheters are described and depicted in the Great-Grandparent application (U.S. application Ser. No. 13/801,750, filed on Mar. 13, 2013) which has been incorporated into this application by a specific reference above. In multi-lumen embodiments, a dedicated single lumen may also be designated for the axial propagation of EMR and each additional lumen dedicated for the injection or retrieval of fluid axially. In this way both fluid and EMR can be axially propagated simultaneously through their individual lines and the EMR-delivering optical element 14 and fluids need not occupy the same lumen.

Figure 4:
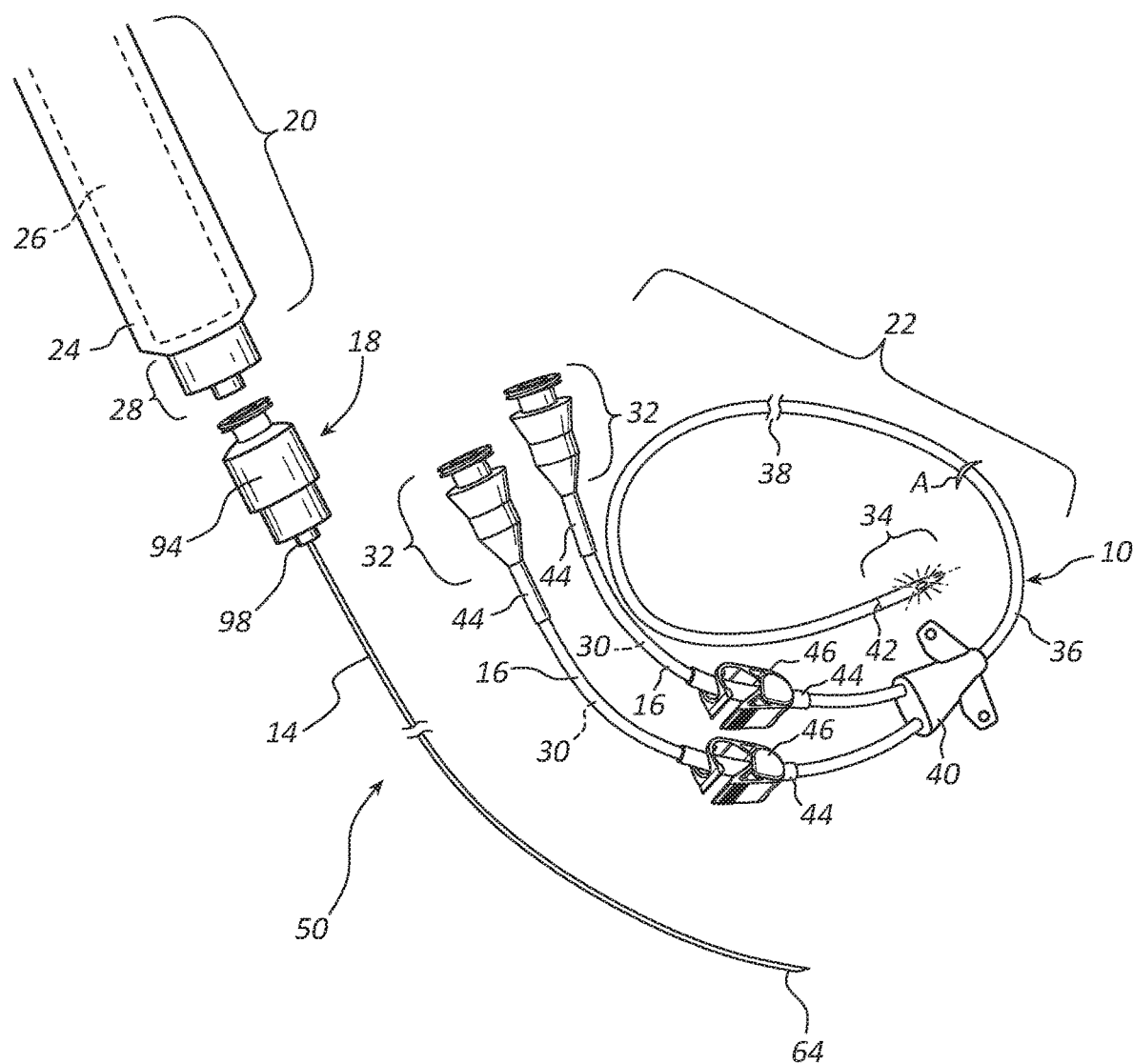
FIG. 4 is a perspective, partially exploded view of still another exemplary embodiment of a dual lumen catheter with the insertable optical element disposed outside the catheter and showing a convergence chamber.

The distal end 34 being insertable into the cavity of the patient's body 12 at a determined incision site A, enables the elongate catheter body 36 to direct the delivery and/or retrieval of fluid and the therapeutic EMR axially relative to the elongate catheter body 36 for delivery into the patient's body 12. The elongate catheter body 36 is described as being an elongated catheter 10 having at least one internal lumen 30. Another embodiment of the present disclosure is depicted in FIG. 4, showing a perspective view of a dual lumen catheter 10 with the removable EMR conduction system 18 outside the catheter 10. The catheter 10 portion of the depiction shows flexible protection tubing 44 that protects the coupling of the proximal catheter hub assembly 32 with the line tubing 16 and also protects line tubing 16 from wear imposed by line clamps 46.

Therapeutic EMR will travel axially relative to the catheter 10 which may be of varying lengths 38 depending on its specific need. The fluids passing through the internal lumen 30 may be injected and contain pharmacological compounds (e.g., a drug, a dialysate, or a saline solution) or may be retrieved biological fluids (e.g., blood, urine, waste dialysate or cerebral spinal fluid).

Each multi-lumen embodiment may contain a convergence chamber 40, at the point where individual internal lumens 30 converge into a single elongated catheter body 36 while retaining their individual internal paths. At the distal end 34 of the elongate catheter body 36, the optical element 14 discontinues at the termination point 42 so that the therapeutic EMR can irradiate throughout the distal end 34 of the catheter 10 and surrounding cavity area forward of the catheter 10.

This embodiment also may be fitted with flexible protection tubing 44 to protect the lumen at the proximal catheter hub assembly 32 and between the proximal catheter hub assembly 32 and convergence chamber 40. If manual line occlusion is necessary it may be performed with the line clamp 46.

Figure 5:
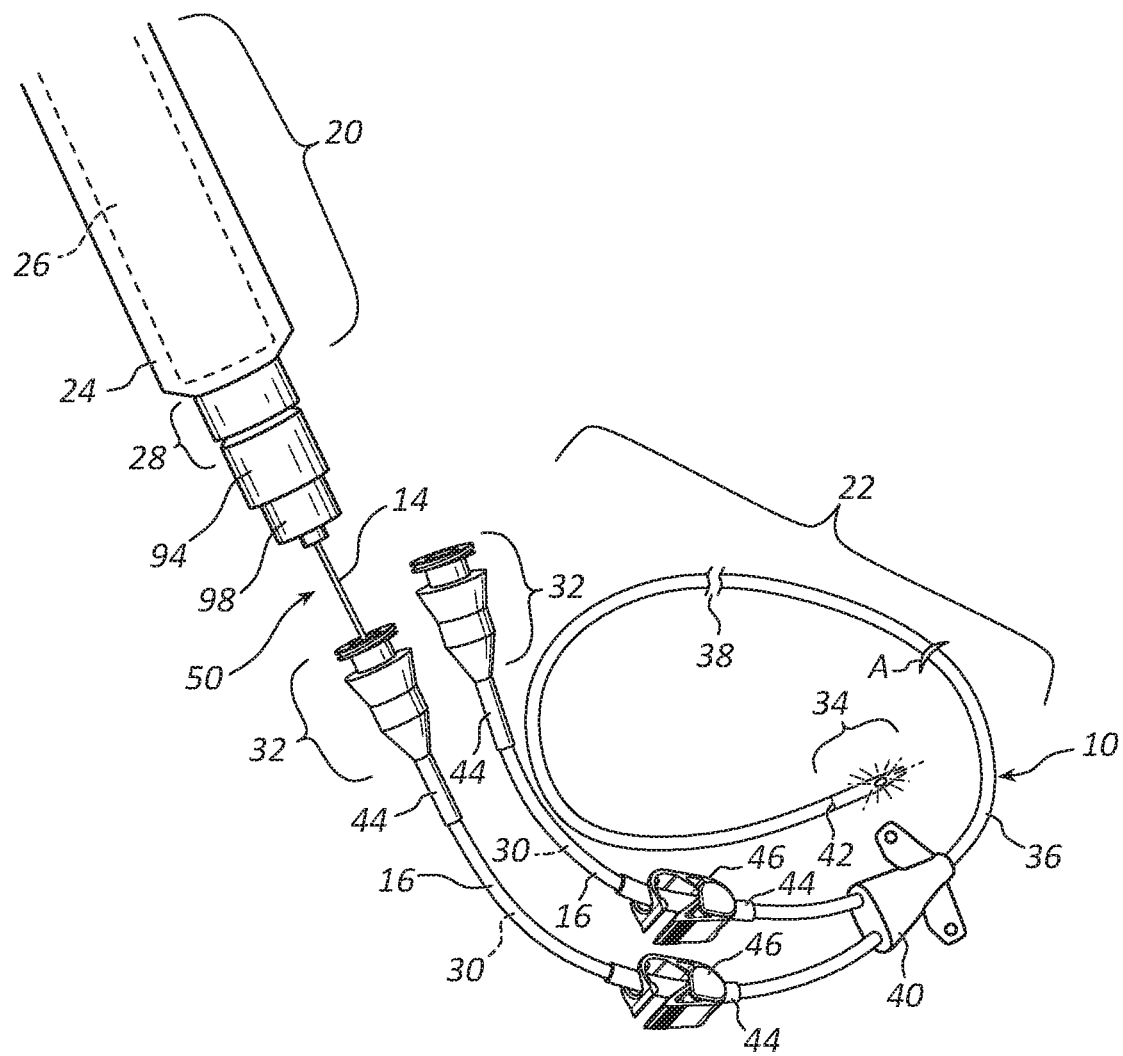
FIG. 5 is a perspective view of the exemplary dual lumen catheter of FIG. 4 with the insertable component disposed partially inside the catheter.

FIG. 5 shows the dual lumen catheter 10 of FIG. 4 with the removably insertable EMR conduction system 18 partially inserted into one of the lumens 30 of the catheter 10.

Figure 6A:
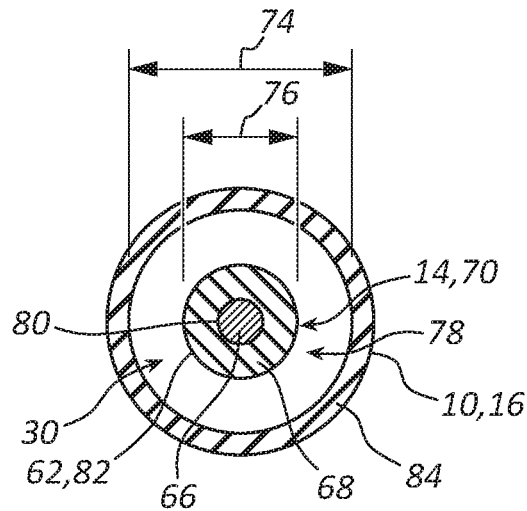
FIG. 6A is a cross sectional view showing an exemplary embodiment of a cladding-encased optical element as centered within a single lumen of the catheter line tubing.

FIGS. 6A-G is a series of illustrative cross-sectional views of alternative optical elements 14 as disposed within an exemplary single-lumen catheter 10 (FIGS. 6A-C) or exemplary multi-lumen catheters 10 (FIGS. 6D-G). FIG. 6A is a cross sectional view showing an exemplary embodiment of a cladding-encased fiber optic 70 as centered within a lumen 30 of the catheter line tubing 16 of a single lumen catheter 10. The single lumen line tubing 16/catheter 10, depicted in cross section, has an inner diameter 74 and a catheter wall 84. The cladding-encased fiber optic 70 is an optical element 14 and has an outer diameter 76, a core-cladding boundary 80 and a cladding outer boundary 82. When the cladding-encased fiber optic 70 is centered, as depicted in FIG. 6A, an annular void 78 is created between the cladding outer boundary 82 and the catheter wall 84 when the inner diameter 74 of the catheter wall 84 is larger than the outer diameter 76 of the cladding-encased fiber optic 70. Fluids may travel through this void 78, whether by injection or retrieval, when the cladding-encased fiber optic 70 resides within the lumen 30 of a single lumen catheter 10.

Figure 6B:
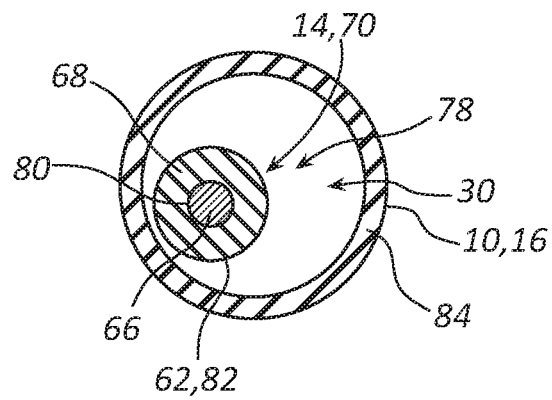
FIG. 6B is a cross sectional view showing an exemplary embodiment of the cladding-encased optical element non-centered within a single lumen of the catheter line tubing.

FIG. 6B is a cross sectional view showing an exemplary embodiment of the cladding-encased fiber optic 70 non-centered within a lumen 30 of the catheter line tubing 16 of a single lumen catheter 10. However, the void 78 formed within the lumen 30 is not annular, and without structure to hold the cladding-encased fiber optic 70 in a centered disposition, the non-centered disposition may occur when the optical element 14 is removably inserted into the lumen 30 of the catheter 10. Consequently, the therapeutic EMR emitted radially from the optical element 14 must pass through the void 78 before reaching and passing through the catheter wall 84. Especially when there is fluid present within the void 78, the intensity of the therapeutic EMR may need to be increased so that the therapeutic EMR emerging from the catheter wall 84 is sufficient to inactivate infectious agents and/or to enhance healthy cell growth in the tissue surrounding the indwelling catheter 10.

Figure 6C:
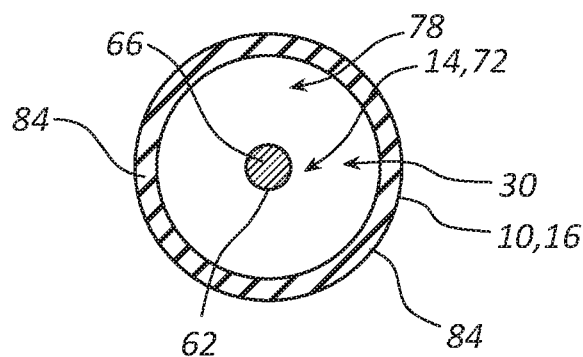
FIG. 6C is a cross sectional view showing another exemplary embodiment of a bare fiber optical element as centered within a single lumen of the catheter line tubing (FIGS. 6A-C are illustrative cross-sectional views of alternative optical elements as disposed within a single-lumen catheter)

FIG. 6C is a cross sectional view showing another exemplary embodiment of a bare fiber optic 72 as centered within a lumen 30 of the catheter line tubing 16 of a single lumen catheter 10. With this embodiment, the void 78 is created between the catheter wall 84 and the exterior surface 62 of the bare fiber optic 72.

Of course, multi-lumen catheters 10 are also contemplated by this disclosure and the context of FIGS. 6A-C can easily be understood by those skilled in the art to apply equally to multi-lumen catheters 10 wherein one or more optical elements 14 may reside within one or more of the multiple lumens 30. Examples of multi-lumen catheters are described and depicted in the Great-Grandparent application (U.S. application Ser. No. 13/801,750, filed on Mar. 13, 2013) which has been incorporated into this application by a specific reference above.

Figure 6D:
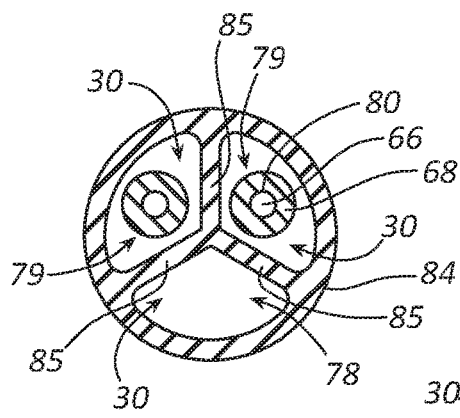
FIG. 6D is a cross sectional view of an exemplary three-lumen catheter showing exemplary cladding-encased optical elements each within separate lumens of the catheter line tubing.

FIG. 6D is a cross sectional view of an exemplary three-lumen catheter 10 showing exemplary cladding-encased fiber optics 70 each centered within separate lumens of the catheter line tubing 16. The three-lumen line tubing/catheter 10, depicted in cross section, has a catheter wall 84 and interior divider walls 85 separating the lumens 30 from each other. When the cladding-encased fiber optics 70 are centered, as depicted in FIG. 6D, a surrounding void 79 is created between the cladding outer boundary 82 and the catheter wall 84 and interior divider walls 85. Fluids may travel through the surrounding void 79, if needed, whether by injection or retrieval.

Figure 6E:
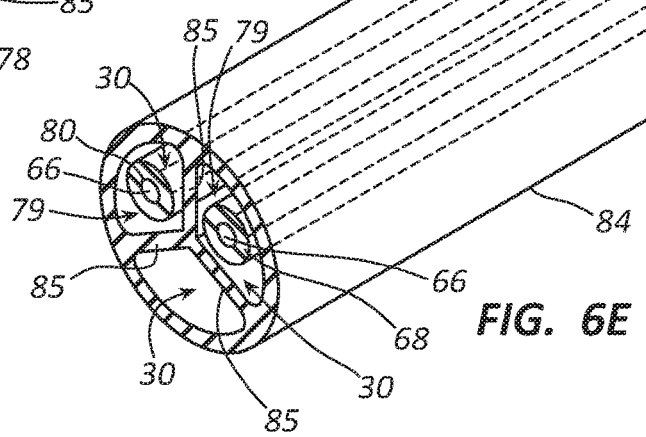
FIG. 6E is a perspective view of a portion of the three-lumen catheter of FIG. 6D cut away to show the length of each cladding-encased optical element to be the same.

FIG. 6E is a perspective view of a portion of the three-lumen catheter 10 of FIG. 6D cut away to show the length of each cladding-encased fiber optic 70 to be the same. With this exemplary embodiment, controlled relative intensity of EMR doses may be delivered simultaneously, alternately, and/or alternatively to each cladding-encase fiber optic 70 for radial emission for treatment region specific dosing as described throughout this disclosure.

Figure 6F:
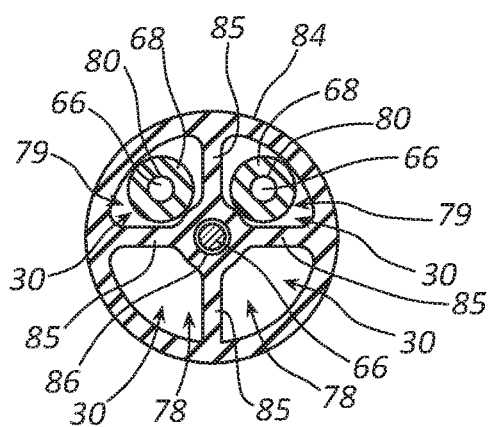
FIG. 6F is a cross sectional view of an exemplary four-lumen catheter with a central core showing exemplary cladding-encased optical elements each within separate lumens of the catheter line tubing and a bare fiber optical element concentrically embedded within the central core.

FIG. 6F is a cross sectional view of an exemplary four-lumen catheter 10 with a central core 86 showing exemplary cladding-encased fiber optics 70 each within separate lumens 30 of the catheter line tubing 16 and a bare fiber optic 72 concentrically embedded within a central core 86.

Figure 6G:
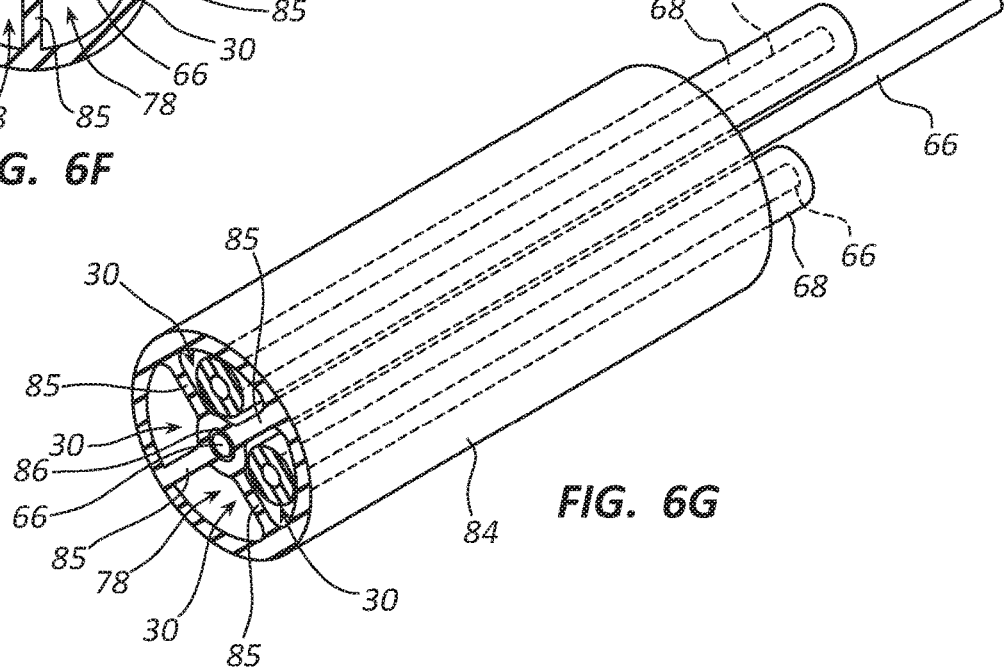
FIG. 6G is a perspective view of a portion of the four-lumen catheter of FIG. 6G cut away to show the length of each cladding-encased optical element and the bare fiber optical element to be different.

FIG. 6G is a perspective view of a portion of the four-lumen catheter of FIG. 6F cut away to show the length of each cladding-encased optical element and the bare fiber optical element to be different. Again, with this exemplary embodiment, controlled relative intensity of EMR doses may be delivered simultaneously, alternately, and/or alternatively to each cladding-encased fiber optic 70 and/or bare fiber optic 72 for radial emission for treatment region specific dosing as described throughout this disclosure. This embodiment also illustrates that the cladding encased fiber optics 70 and the bare fiber optic 72 may be of differing lengths, thereby adding more versatility to controlled relative intensity and/or treatment region specific dosing.

Figure 7A:
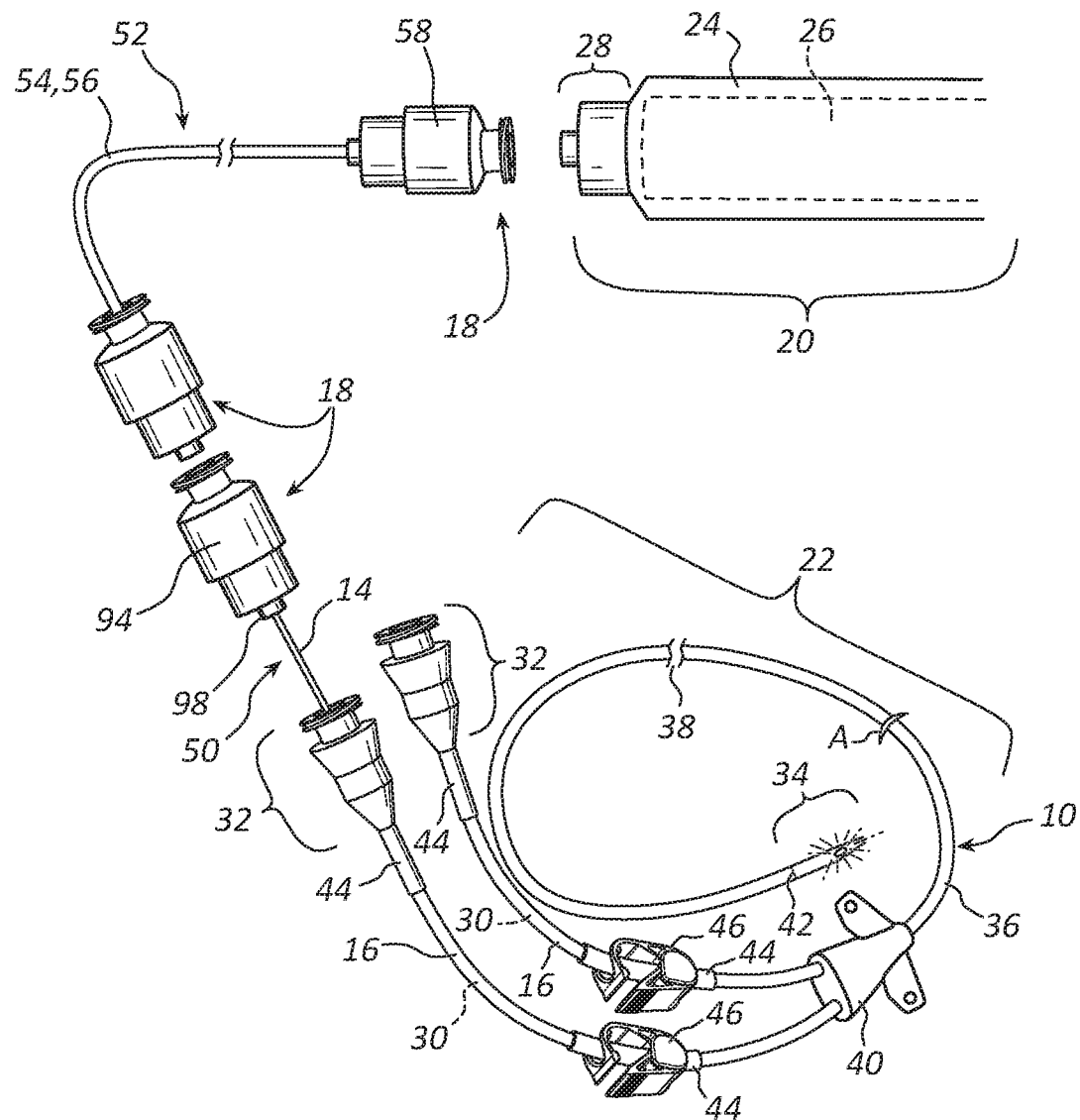
FIG. 7A is a perspective, partially exploded view of an exemplary dual lumen catheter with the removably, insertable optical element of the EMR conduction system disposed partially inside the catheter and showing an intermediate coupling serving as an EMR conduction extending segment.

FIG. 7A shows an exploded perspective view of an exemplary EMR conduction system 18 as partially inserted into the proximal catheter hub assembly 32 and an internal lumen 30. With this exemplary embodiment, an intermediate coupling 52 is shown. Such intermediate coupling 52 may comprise a patch cable 54 or an EMR conduction extending segment 56 used to extend the distance between the EMR power source 26 and the optical element connector 94 of the insertable optical element 14, without appreciable loss of light intensity. Each of the patch cable 54 or EMR conduction extending segment 56 may have a forward connector 58 to securely engage coupling element 28, and a rearward connector 60 to securely engage the optical element connector 94. Hence, by using a patch cable 54 or an EMR conduction extending segment 56, the EMR power source 26 may be operated some desired distance from the patient to reduce noise or heat concerns and/or to position the EMR power source 26 proximate to a power source (not shown) such as an electrical outlet or battery pack.

Figure 7B:
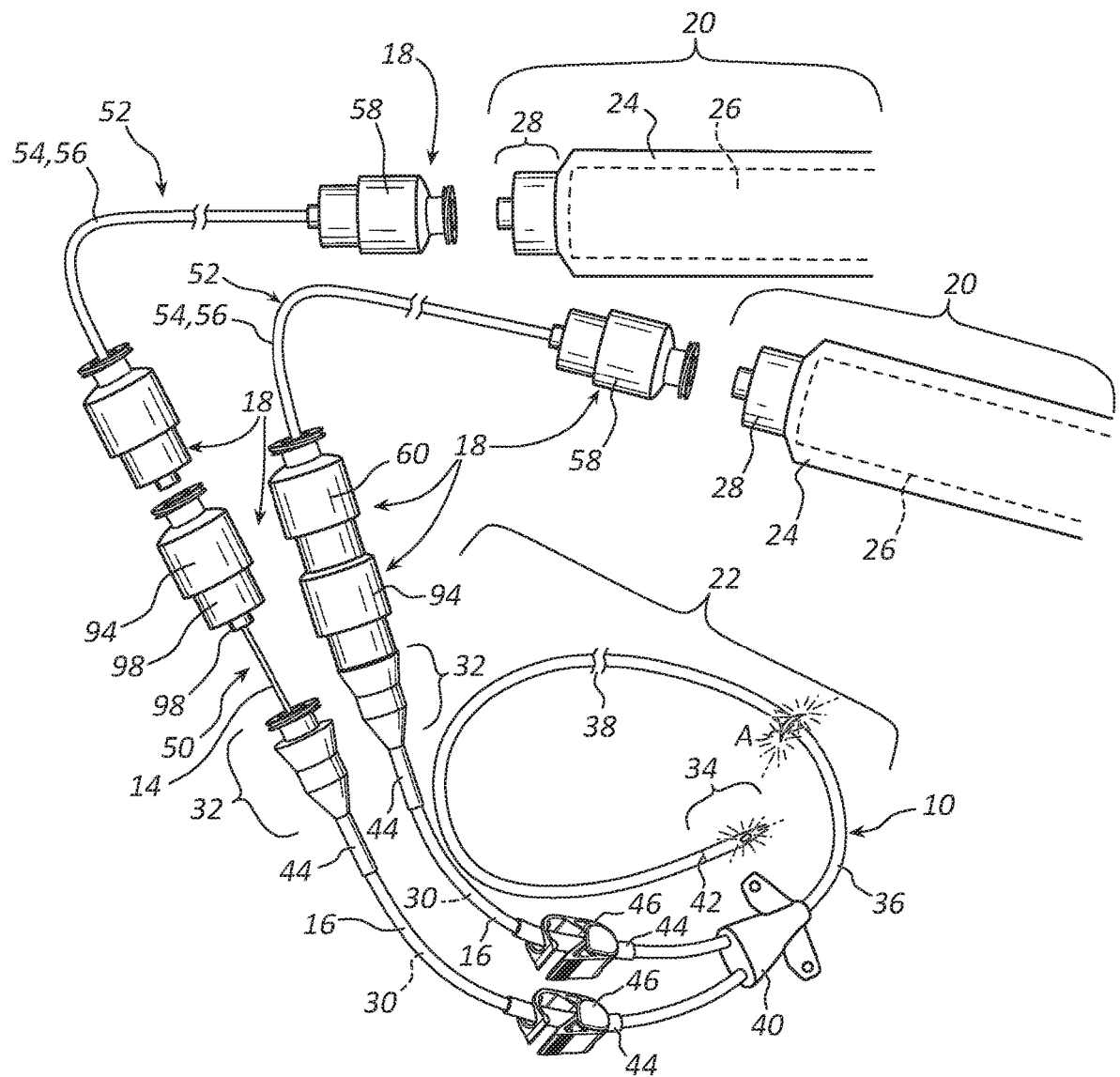
FIG. 7B is a perspective, partially exploded view of the exemplary dual lumen catheter of FIG. 7A showing two EMR conduction systems one having the removably, insertable optical element of the EMR conduction system disposed partially inside the catheter and the other having the removably, insertable optical element of the EMR conduction system disposed fully inside and encapsulated by the catheter.

FIG. 7B is a perspective, partially exploded view of the exemplary dual lumen catheter 10 of FIG. 7A showing two EMR conduction systems 18 one having the removably, insertable optical element 14 of the EMR conduction system 18 disposed partially inside the catheter 10 and the other having the removably, insertable optical element 14 of the EMR conduction system 18 disposed fully inside and encapsulated by the catheter 10. With this exemplary embodiment, controlled relative intensity of EMR doses may be delivered simultaneously, alternately, and/or alternatively using different EMR sources and may also be used to add more versatility to controlled relative intensity and/or treatment region specific dosing.

FIGS. 8A-E is a series of elevation views of several exemplary embodiments of an optical assembly 50 showing various locations with non-gradient and gradient degrees of alteration on the exterior surface 62 of the insertable optical element 14. Each view of the series of views shows an optical assembly 50 with an insertable optical element 14 connected to the optical element connector 94. The exemplary optical element connector 94 (see also FIGS. 7A and 9A) has a connecting element 88, an EMR hub connection 90, a collimating lens 92, and an alignment shaft 98.

The first view (uppermost, FIG. 8A) of the series of views shows an unaltered optical span 100 of the insertable optical element 14 that is without any radial dispersion (i.e., the insertable optical element 14 has not been treated or altered to provide radial emission of light from the body of the insertable optical element 14). With this embodiment, therapeutic, non-ultra-violet EMR may be provided to a distal end 64 of the optical element 14 with no radial emission from the optical span 100 other than at the distal end 64.

The second view (next view down, FIG. 8B) of the series of views shows an exemplary radial transmission equivalency over a radial emission portion 103 (i.e., radial emission portion 103, as depicted, has a gradient modification such that the emitted EMR has substantially uniform intensity and power over the length of the radial emission portion 103) that provides radially dispersed light from a segment-modified optical span 102. The location of the single radial emission portion 103, in this instance, corresponds to where the catheter 10 enters the insertion site A when the insertable optical element 14 is inserted fully into the catheter 10. With this embodiment, radially emitted visual light may sterilize and/or enhance healthy cell growth at the insertion site A and the transdermal area 48 or any other predetermined site within the patient's body 12 by positioning one or more segment-modified optical spans 102 along the length of the insertable optical element 14.

Figure 8A:
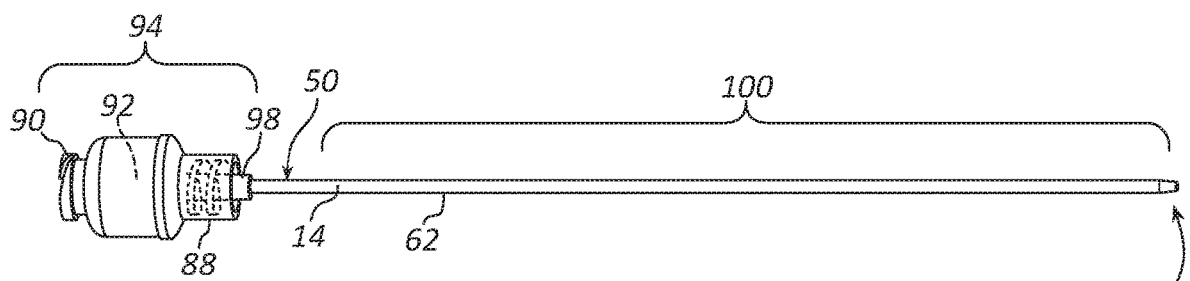
FIGS. 8A-E is a series of elevation views of several exemplary embodiments of a removably, insertable optical element with varying locations, lengths, and degrees of alteration, and with an optical element connector shown as transparent to better illustrate internal features that are shown in phantom lines.
Figure 8B:
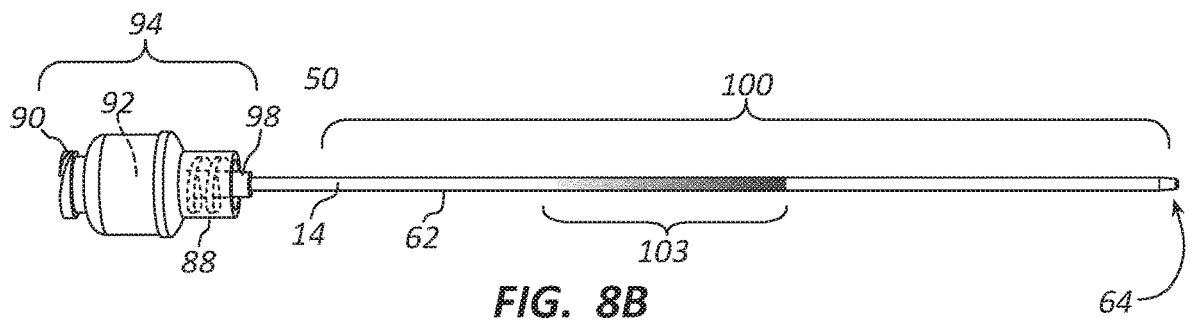
Figure 8C:
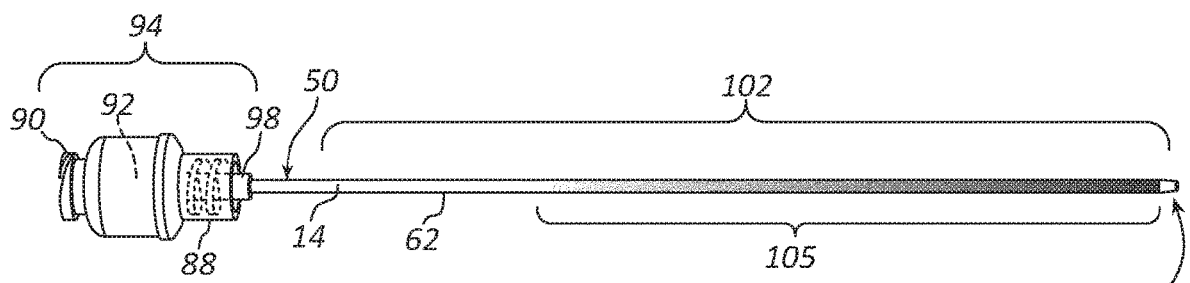
Figure 8D:
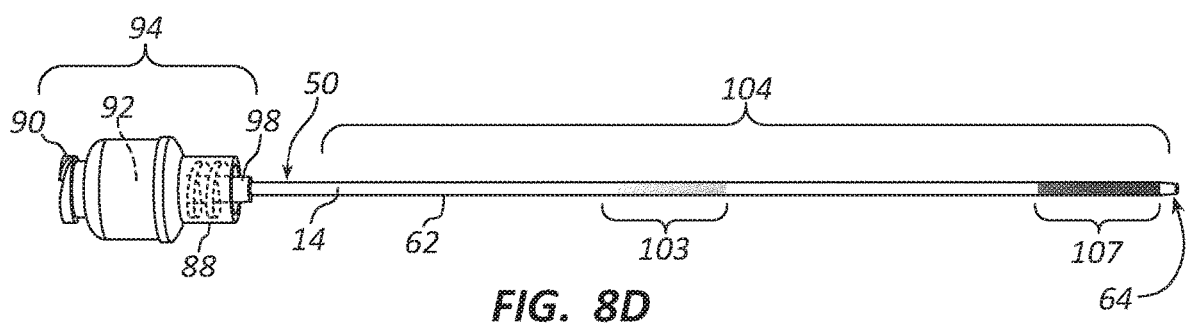
Figure 8E:
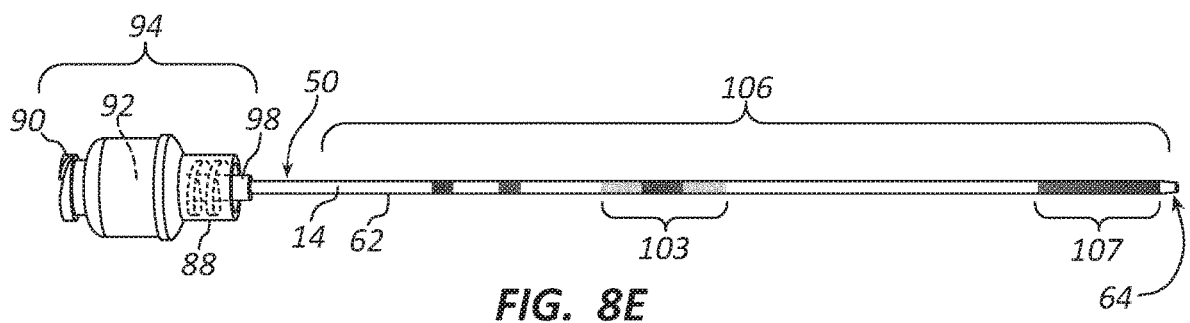

Each of the views in FIGS. 8B-E depicts a gradient modification to facilitate emitting EMR in a pattern wherein there is substantially uniform intensity and power over the length of the radial emission portion(s) 103, 105. It should be understood, however, that although each of the views depict EMR of uniform intensity and power, any desired pattern of EMR emission may be achieved by varying the degree of modification within the radial emission portion 103 because less ablation will permit less radial emission of EMR and more ablation will permit more radial emission of EMR. For example, as shown in FIG. 8E, a radial emission portion 103 with less ablation proximate each end and more ablation in the middle will emit EMR of lesser intensity and power on each end with more intensity and power emitting in the middle. Hence, any desired pattern of EMR emission may be created by adjusting the pattern of ablation within the radial emission portion 103.

The third view of the series of views (FIG. 8C) shows an example of a single radial emission portion 105 that provides radially dispersed EMR from optical element 14 extending along most of a fully-modified optical span 104. The location of the single radial emission portion 105 corresponds generally to the entire length of the insertable catheter component 22 of the catheter 10 from insertion site A to distal end 64. With this embodiment, therapeutic EMR may be provided for substantially the entire length that the catheter 10 that would be inserted within the patient's body 12, including the incision site A.

The fourth view of the series of views (FIG. 8D) shows an example of radial transmission uniformity at multiple locations. A single radial emission portion 103 and an additional distal end region radial emission portion 107 are spaced along a multi-modified optical span 106. The locations of the radial emission portion 103 and the distal end region radial emission portion 107 correspond to areas of the body, including for example the insertion site A, where the delivery of non-ultraviolet, therapeutic EMR may be desired for sterilization and/or healing. It should be understood that there may be more than one radial emission portion 103 disposed along the length of the multi-modified optical span 106 and/or each radial emission portion 103 may be distinct from each other radial emission portion 103 and each may have differing lengths and degrees of gradient ablation.

Also, it should be understood that in each of these views the radial emission portions depicted may be of modifications other than modification of the exterior surface 62 of the insertable optical element 14, such as for example, modifications including microscopic structures embedded within the insertable optical element 14 that allow radial transmission of light from the insertable optical element 14. Further, such radial emission portions 103, 105, 107 may have gradient patterns that allow for an overall substantially-uniform distribution of light over the length of each radial emission portion 103, 105, 107 or non-gradient of variant gradient patterns may result in non-uniform distribution of light over the length of each radial emission portion 103, 105, 107. It should also be understood that the versatility of degree, length and location of each radial emission portion 103, 105, 107 facilitates controlled relative intensity and/or treatment region specific dosing.

Figure 9A:
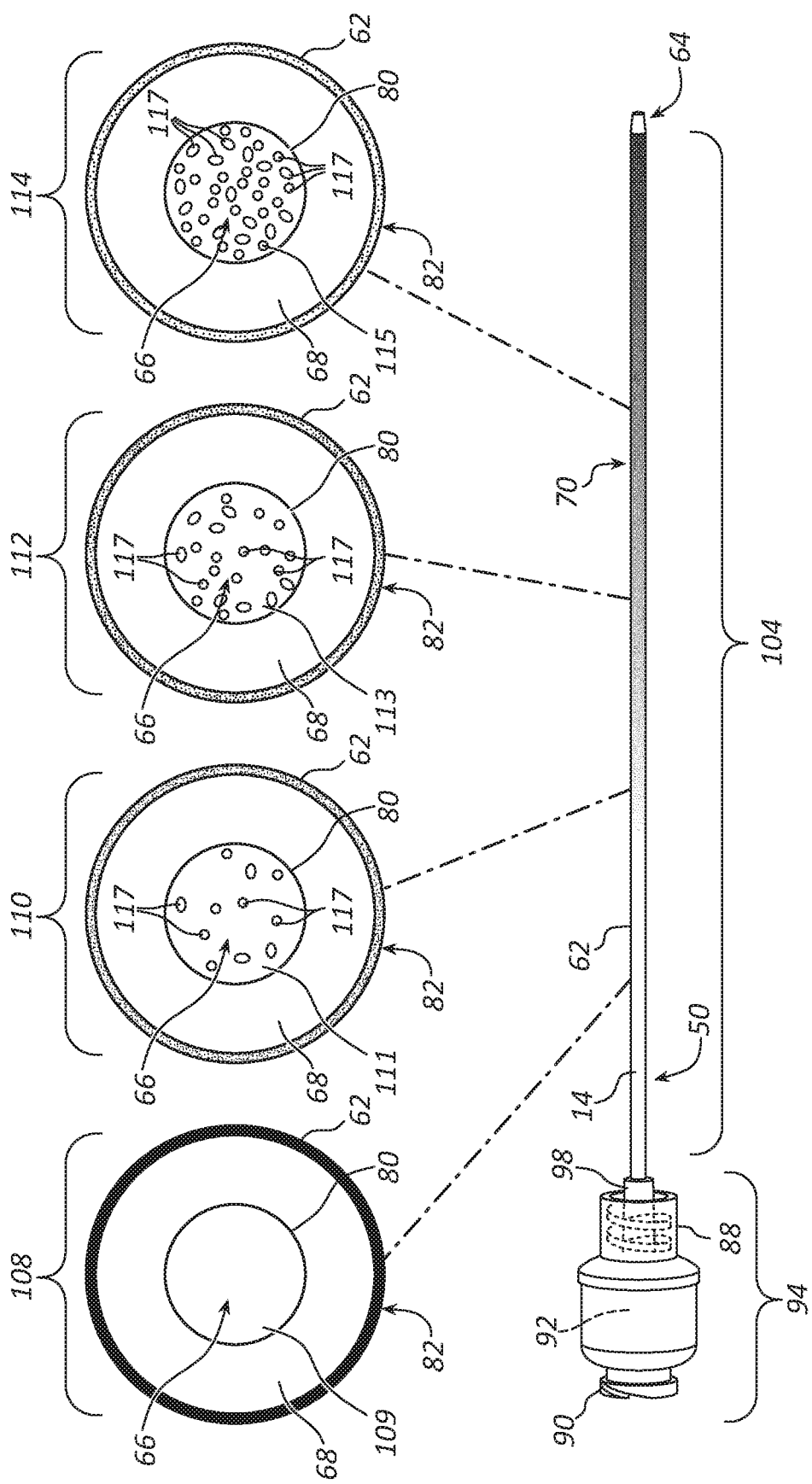
FIG. 9A shows cross-sectional views of multiple portions of an exemplary removably, insertable optical element (similar to that shown in FIG. 8C) with various EMR radial, gradient emission levels.

FIG. 9A is a schematic view of an optical assembly 50 with an insertable optical element 14 coupled to an optical element connector 94. The insertable optical element 14 has a fully-modified optical span 104. Multiple locations along the insertable optical element 14 are shown in enlarged cross-sectional views. These locations are axially spaced along the insertable optical element 14 to assist in describing the nature of an exemplary insertable optical element 14 at each location. As depicted, there are four section locations, a first section 108, a second section 110, a third section 112, and a fourth section 114. For brevity, the modifications on and in the insertable optical element 14 at each of the four sections are combined in the depictions of FIG. 9A. Of course, the radial emission portions of the insertable optical element 14 may be singular or multiple, may be any length or gradient or non-gradient, and may be coincident, overlapping or not.

The first section 108 represents an internally reflected region of the insertable optical element 14. As shown at the first section 108, there is no ablation (or other modification) and no microscopic structure within the core 66 of the insertable optical element 14. No therapeutic, non-ultraviolet EMR will emit radially from the insertable optical element 14 at the first section 108.

The second section 110 represents a minimally emissive region of the insertable optical element 14. As shown at the second section 110, there is minimal ablation (or other modification) to the exterior surface 62 of the insertable optical element 14 and a minimal dispersal of microscopic structures 117 within the core 66 of the insertable optical element 14. From the second section 110, minimal therapeutic, non-ultraviolet EMR will emit radially from the insertable optical element 14. However, the amount of EMR emitted should have sufficient intensity and power to inactivate infectious agents and/or promote healing proximate the second section 110.

The third section 112 represents a moderately emissive region of the insertable optical element 14. As shown at the third section 112, there is moderate ablation (or other modification) to the exterior surface 62 of the insertable optical element 14 and moderate dispersal of microscopic structures 117 within the core 66 of the insertable optical element 14. From the third section 112, a moderate amount of therapeutic, non-ultraviolet EMR will emit radially from the insertable optical element 14 proximate the third section 112. However, prior to reaching the third section 112, the amount of light traveling axially along the insertable optical element 14 diminishes due to the radial emission of some of the light such as at second section 110. Consequently, the degree of the gradient of modification is selected so that the amount of EMR emitted radially at third section 112 should be substantially uniform with the radial emission at the second section 110. Hence, the intensity and power of the EMR emitted may be substantially uniform with the intensity and power emitted at second section 110 and is of sufficient intensity and power to inactivate infectious agents and/or promote healing.

The fourth section 114 represents a maximally emissive region of the insertable optical element 14. As shown at the fourth section 114, there is maximal ablation (or other modification) to the exterior surface 62 of the insertable optical element 14 and maximal dispersal of microscopic structures 117 within the core 66 of the insertable optical element 14. From the fourth section 114, a maximum amount of therapeutic, non-ultraviolet EMR will emit radially from the insertable optical element 14 proximate the fourth section 114. Again, prior to reaching the fourth section 114, the amount of light continuing to travel axially along the insertable optical element 14 diminishes due to the radial emission of some of the light such as at second section 110 and at third section 112. Consequently, the degree of the gradient of modification is selected so that the amount of EMR emitted radially at fourth section 114 should be substantially uniform with the emissions at second section 110 and third section 112. The intensity and power of the EMR emitted may be substantially uniform with the intensity and power emitted at second section 110 and third section 112 and is of sufficient intensity and power to inactivate infectious agents and/or promote healing.

The radial emission portions may be modified by chemical, physical or other cladding modification (e.g., ablation) to alter the critical angle enough to allow light to emit radially. Additionally, or alternatively, the radial emission portions may be modified by dispersing microscopic structures 117 of varying gradient concentration inside the core 66 of the insertable element 14. The gradient concentration of microscopic structures 117 within the core 66 shown in FIG. 9A range from a microscopic structures free area 109, to a minimal concentration 111 of microscopic structures 117, to a moderate concentration 113 of microscopic structures 117, to a maximal concentration 115 of microscopic structures 117.

The concentration of microscopic structures 117 within the core 66 affects the refractive index of the core 66 and the core-cladding boundary 80. The microscopic structures 117 (which may be, for example, reflective flakes or voids, such as bubbles) create changes in the incident angle of the light as it passes through the insertable optical element 14. At certain incident angles, light leaves the optical element cladding 68 and emits radially from the cladding outer boundary 82.

Figure 9B:
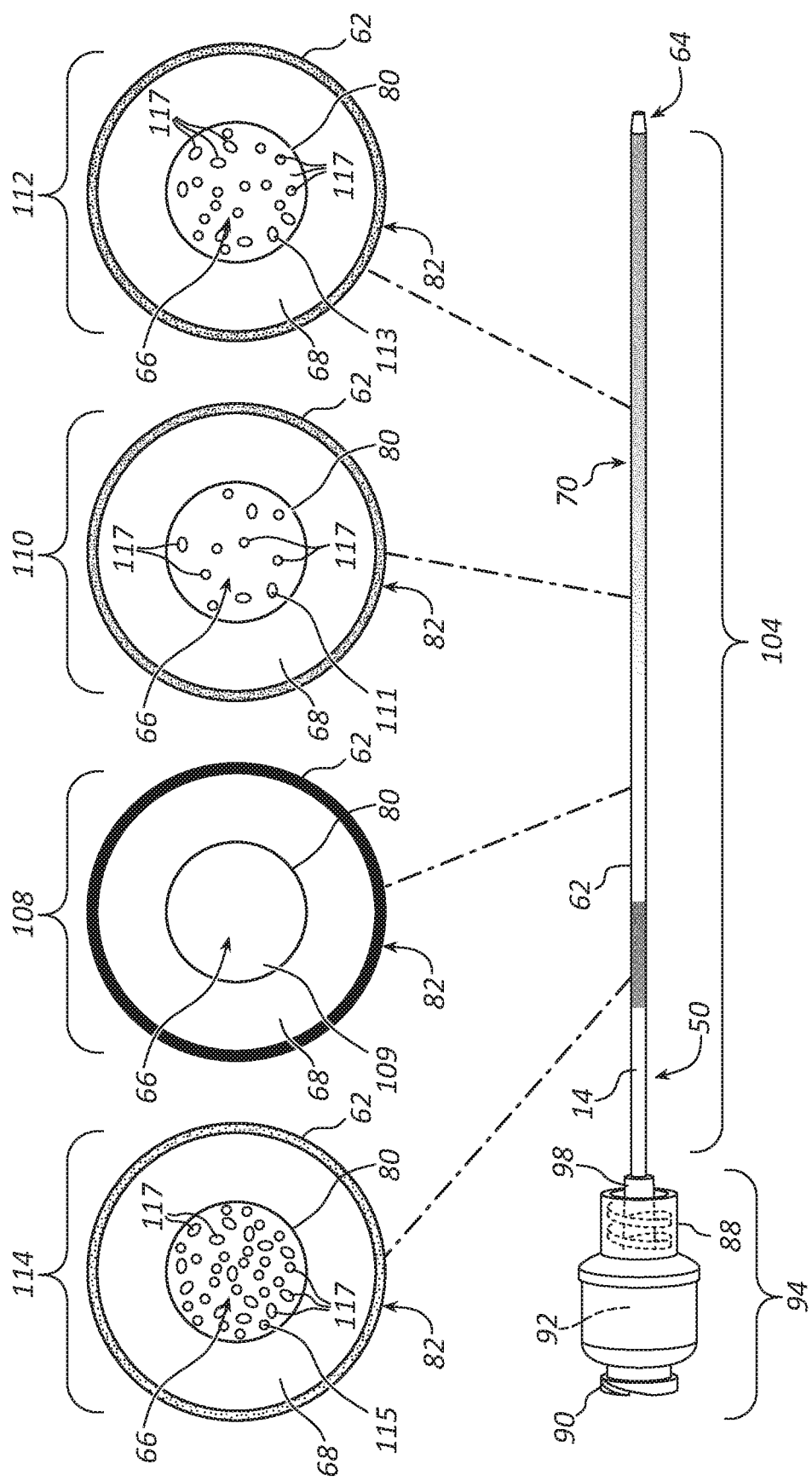
FIG. 9B shows cross-sectional views of multiple portions of yet another exemplary removably, insertable optical element showing examples of non-gradient and gradient EMR radial, emission levels, again an example of controlled relative intensity.

FIG. 9B shows cross-sectional views of multiple portions of yet another exemplary removably, insertable optical element 14 showing examples of non-gradient and gradient EMR radial emission levels, again an example of controlled relative intensity and treatment region specific dosing.

Figure 10:
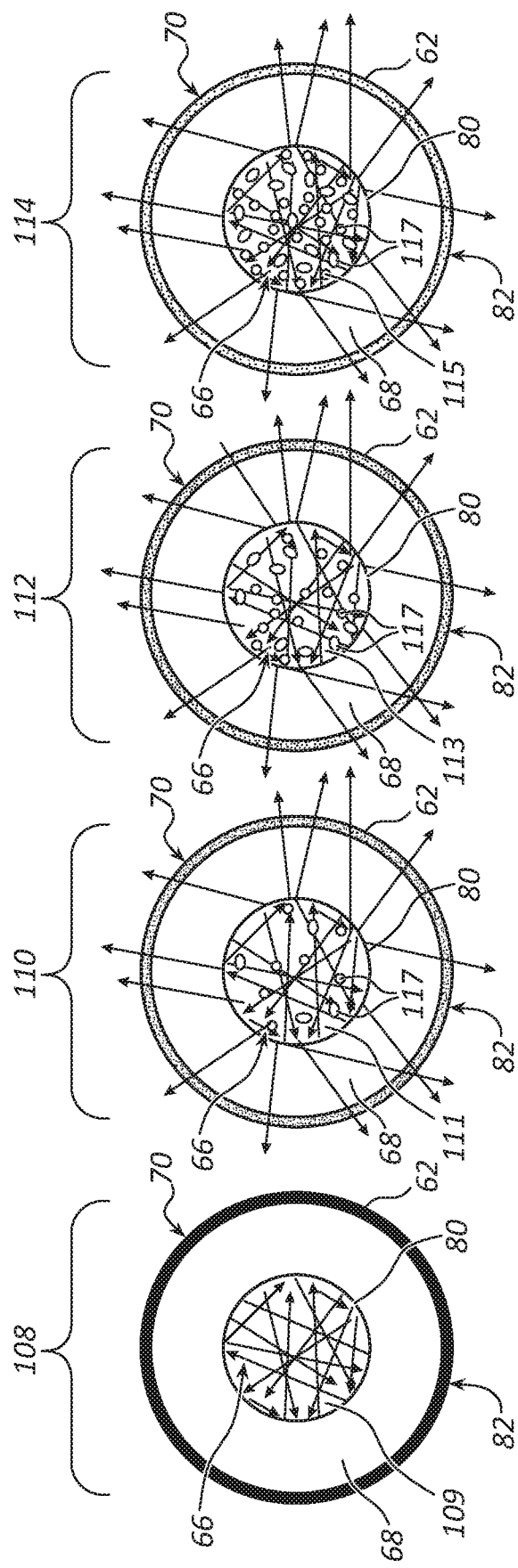
FIG. 10 shows the cross-sectional views of various gradient emission levels of FIG. 9A showing the sections with EMR ray diagrams of internal reflection, and relative radial emission.

FIG. 10 is a schematic view of the cross-sectional views of FIG. 9A depicting light rays as arrows. The same cross-sectional views of the insertable optical element 14 are shown: namely, the first section 108 (internally reflected), the second section 110 (minimally radially emissive), the third section 112 (moderately radially emissive), and the fourth section 114 (maximally radially emissive). These views also show light rays traveling axially along the core 66, that collide with microscopic structures 117 at an incident angle causing the light ray to pass through the optical element cladding 68. An increasing pixilated gradient is depicted on the cladding boundary 82 from the first section 108 (no pixilation), to the second section 110 (minimal pixilation), to the third section 112 (moderate pixilation), to the fourth section 114 (maximal pixilation) represents the chemical, physical or other cladding modification (e.g., ablation) at the cladding boundary 82. Such modification of the insertable optical element 14 alters critical angles enough to allow light to emit radially. As schematically depicted, the number of rays leaving the optical element cladding 68 are substantially equivalent at each site although the amount of light remaining within the core 66 diminishes as the light travels from proximal to distal. The microscopic structures 117 of varying gradient concentration are also shown inside the core 66, from the microscopic structure free area 109, to a minimal concentration 111, to a moderate concentration 113, to a maximal concentration 115. Each of the microscopic structures 117 has a refractive index that differs from that of the core 66 and the optical element cladding 68. The microscopic structures 117 (which may be, for example, reflective flecks or voids, such as bubbles) create changes in the incident angle of the light as it passes through the insertable optical element 14. At certain incident angles, light leaves the optical element cladding 68 and emits radially.

Figure 11:
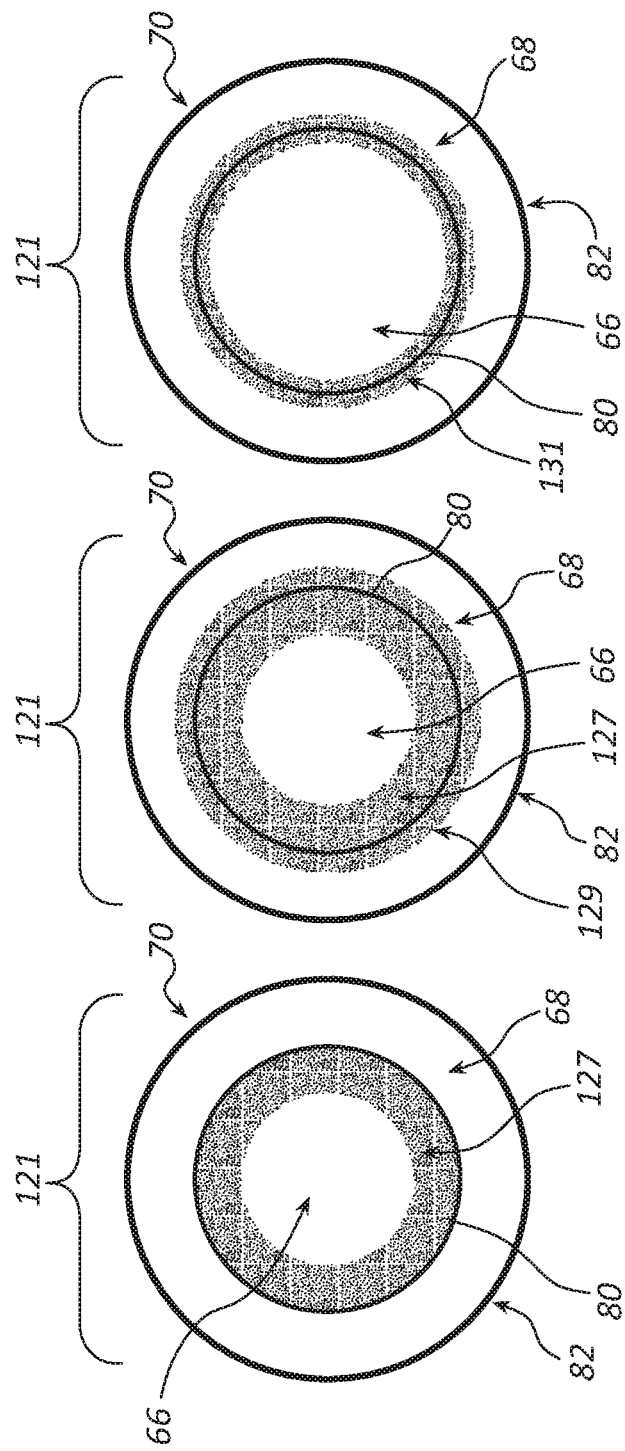
FIG. 11 shows cross-sectional views of various exemplary dispersals of microscopic structures (such as flecks or bubbles) within a fiber optic's core, cladding, and the core/cladding boundary.

FIG. 11 shows cross-sectional views of various exemplary dispersals of microscopic structures 117 (such as flecks or bubbles) within a fiber optic's core 66, cladding 68, and the core/cladding boundary 80. With each of the exemplary embodiments depicted, microscopic structures 117 are dispersed within the insertable optical element 14 (in this case an optical fiber) to achieve radial transmission of light. These microscopic structures 117 may be positioned within the core 66 and/or at the core-cladding boundary 80 and/or within the cladding 68 of the optical fiber 14. The microscopic structures 117 having a refractive index lower than the region free of microscopic structures 117. The microscopic structures 117 may be a material added to the optical fiber core 66 or the core-cladding boundary 80, such as a metal, rubber, glass beads, or plastic. The microscopic structures 117 may also be the lack of material creating an aberration within the optical fiber core 66 and/or the core-cladding boundary 80 and/or within the cladding 68. For example, the presence of microscopic structures 117 (such as bubbles) in the optical fiber core 66 creates an aberration or imperfection that would alter the materials refractive index, resulting in EMR being emitted radially from the optical fiber (insertable optical element 14).

In FIG. 11, three exemplary dispersals, a first dispersal 121, a second dispersal 123, and a third dispersal 125, are depicted. The first dispersal 121 has microscopic structures 117 (such as flecks or bubbles) dispersed within and outer region 127 of the core 66 only. The second dispersal 123 has microscopic structures 117 dispersed within an inner region 129 of the cladding 68 as well as within the outer region 127 of core 66. The third dispersal 125 has microscopic structures 117 dispersed proximate to the core/cladding boundary 80 and are depicted as identifying a boundary region 131 that is thinner than the outer region 127 of the core 66 and the inner region 129 of the cladding 68. With each of the exemplary dispersals, at least some of the light traveling the length of the insertable optical element 14 (fiber optic) will not encounter any microscopic structures 117 while the remainder of the light may encounter at least one microscopic structure 117 and be deflected to emit radially from the insertable optical element 14.

Figure 12:
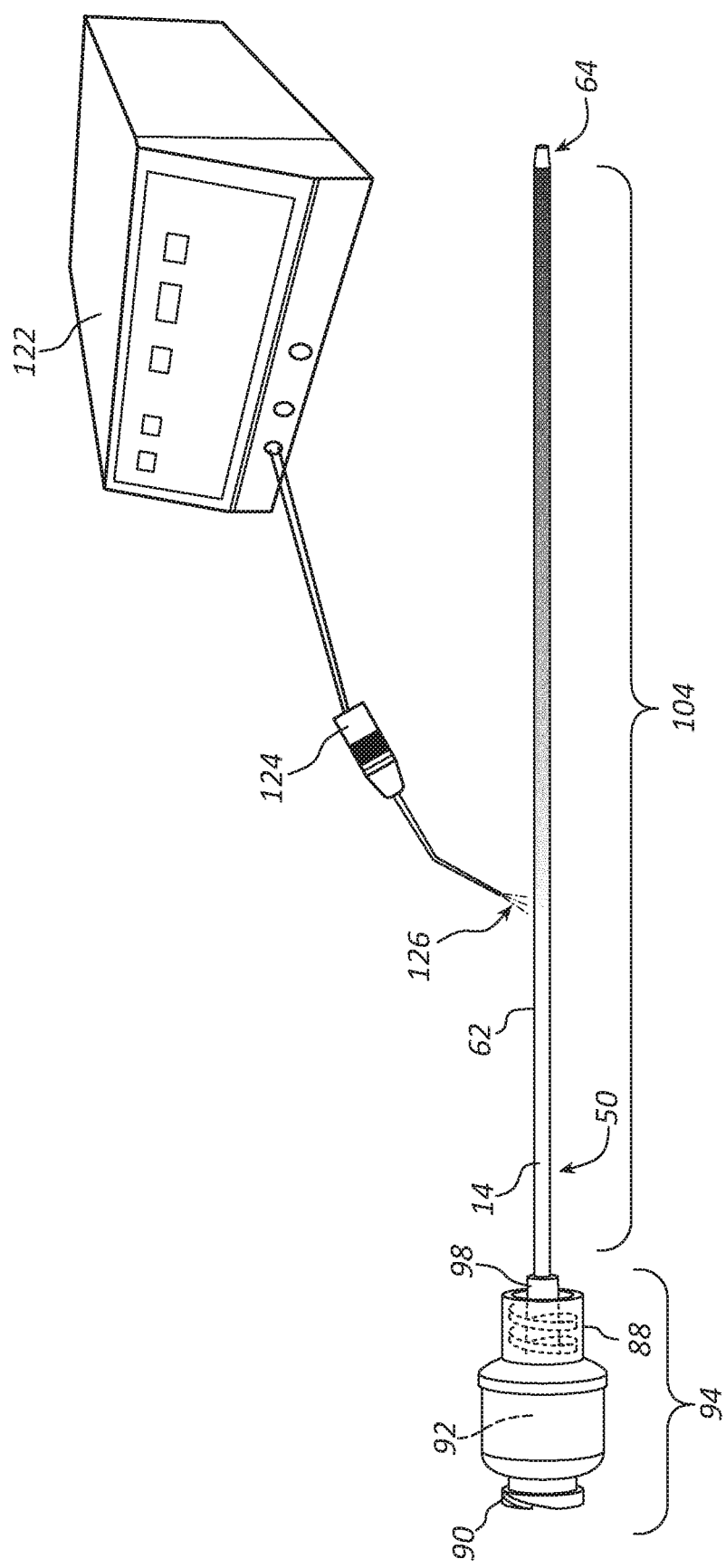
FIG. 12 is a schematic view of an ablating treatment being applied to the removably, insertable optical element remote from its distal end.

FIG. 12 is a schematic view of an exemplary optical element modification method for creating gradient modification on the exterior surface 62 of the insertable optical element 14. Such modification of the core 66 or optical element cladding 68 alters the incident angle of light rays so that they differ from the critical angle needed to remain internally reflected. Depicted in FIG. 12 is a control device 122 with a wand 124 delivering an acid spray 126 for etching the insertable optical element 14.

There are several methods for achieving this gradient modification. Chemically, the insertable optical element 14 may be etched using a strong acid such as hydrofluoric acid or sulfuric acid and hydrogen-peroxide. Also, quartz powder, calcium fluoride, or an etching cream, usually carrying a fluorinated compound, may be used. Physically, heating the insertable optical element 14 or physical modification such as ablation by sanding, media blasting, grinding, or laser ablation modifications are also methods for creating gradient modification. Additionally, plasma ablation by laser modification causes the ionization of molecules and alteration of the exterior surface 62 of the insertable optical element 14. Other known methods for creating gradient ablation are contemplated by this disclosure. Regardless of the modification or manufacturing process, whether presently known or not, the insertable optical element 14 may be modified to have substantially equivalent radially emitted light along desired lengths. This uniformity in radially emitted light allows for a more accurate treatment dose for inactivating infectious agents and/or promoting healing.

In FIGS. 8A-E, 9A, 9B, and 12 of the present disclosure, a transparent view of the optical element connector 94 is depicted, comprising a connecting element 88, an EMR hub connection 90, a collimating lens 92, and an alignment shaft 98. The insertable optical element 14 may be inserted into an aligning bore of the optical element connector 94 to collimate the light into a small diameter core 66 or one or more optical fibers.

The exemplary disclosure depicts an optical diversion element as a single collimating lens 92, but other types of optical diversion elements such as multiple lenses or different types of lenses may be used to collimate the light. Depending on the optical element 14 diameter, numerical aperture, and refractive index, specific lenses will be needed as an optical diversion element to reduce light loss.

Figure 13:
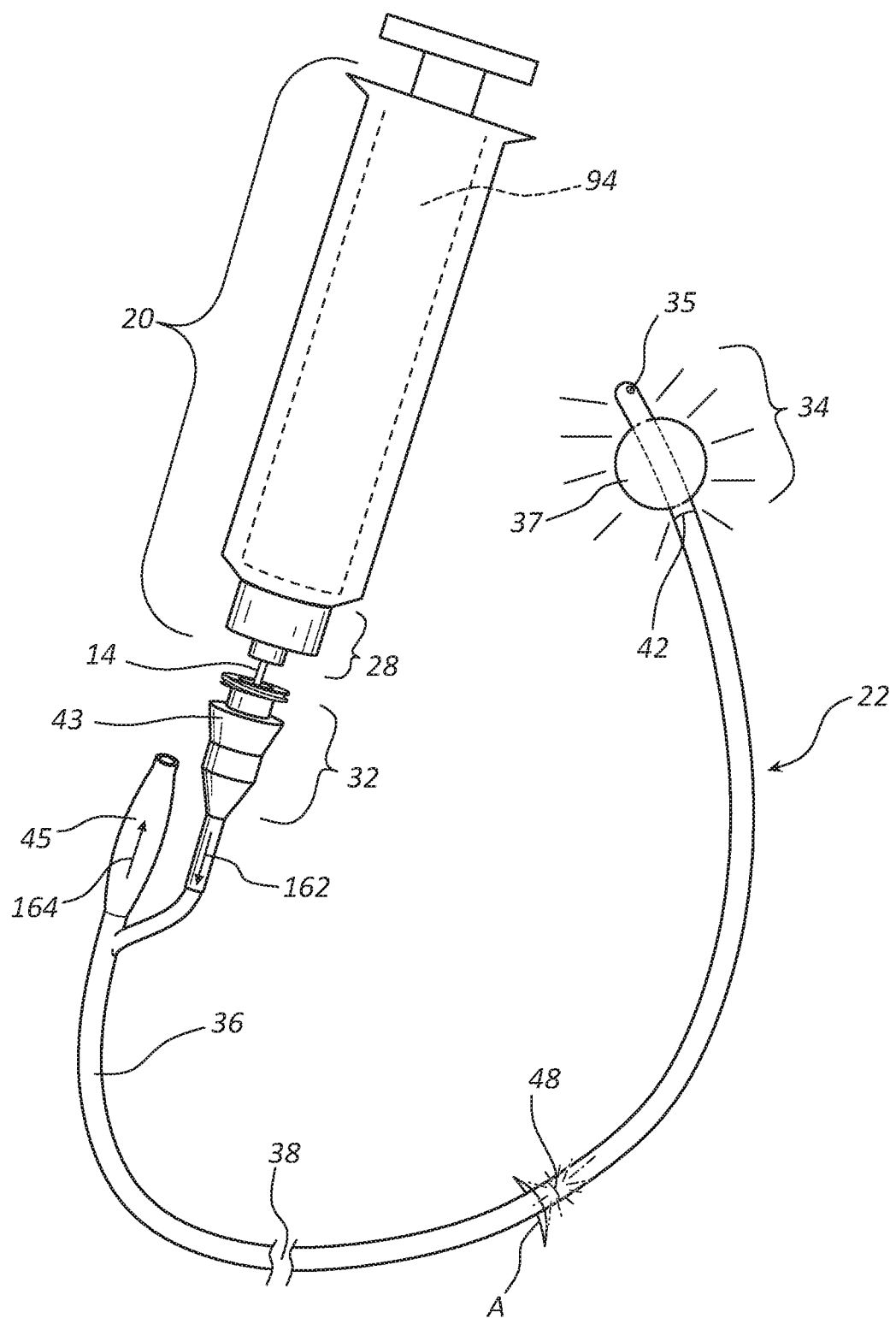
FIG. 13 is a perspective, partially exploded view of an exemplary embodiment of a urinary catheter with the removably, insertable optical element shown partially inserted into an input port and the balloon cuff inflated.

Turning now to FIG. 13, a urinary catheter assembly is depicted. The urinary catheter assembly comprises and electromagnetic radiation component 20 and an insertable catheter component 22. The insertable catheter component comprises a proximal catheter hub assembly 32, an elongate catheter body 36 and a distal end 34 region. The proximal catheter hub assembly 32 serves as an input port 43 (the arrow showing the direction of fluid flow and/or therapeutic EMR propagation 162). The elongate catheter body 36 also comprises an output port 45 for draining urine from the patient (the arrow showing the direction of urine flow 164), an inflatable balloon cuff 37 (shown inflated), and an aperture 35, the balloon cuff 37 and aperture 35 are disposed within the distal end 34 region. The insertable catheter component 22 may be made in varying lengths 38 as female urinary catheters are typically shorter than male urinary catheters which are made to different lengths.

The electromagnetic radiation component 20 comprises an EMR power source 26, a coupling element 28, and an optical element 14. As depicted, the coupling element 28 is spaced from the catheter hub assembly 32 to reveal the optical element 14 that is partially inserted into the lumen 30 of the elongate catheter body 36. When the coupling element 28 is connected to the catheter hub assembly 32, the optical element will be fully inserted and the distal end of the optical element 14 will extend to the termination 42 so not to interfere with the inflatable balloon cuff 37 or the aperture 35. In this fully inserted disposition, the optical element 14 may emit radially therapeutic EMR at the incision site A and into the transdermal area 48, as well as in the distal end region 34.

Figure 14:
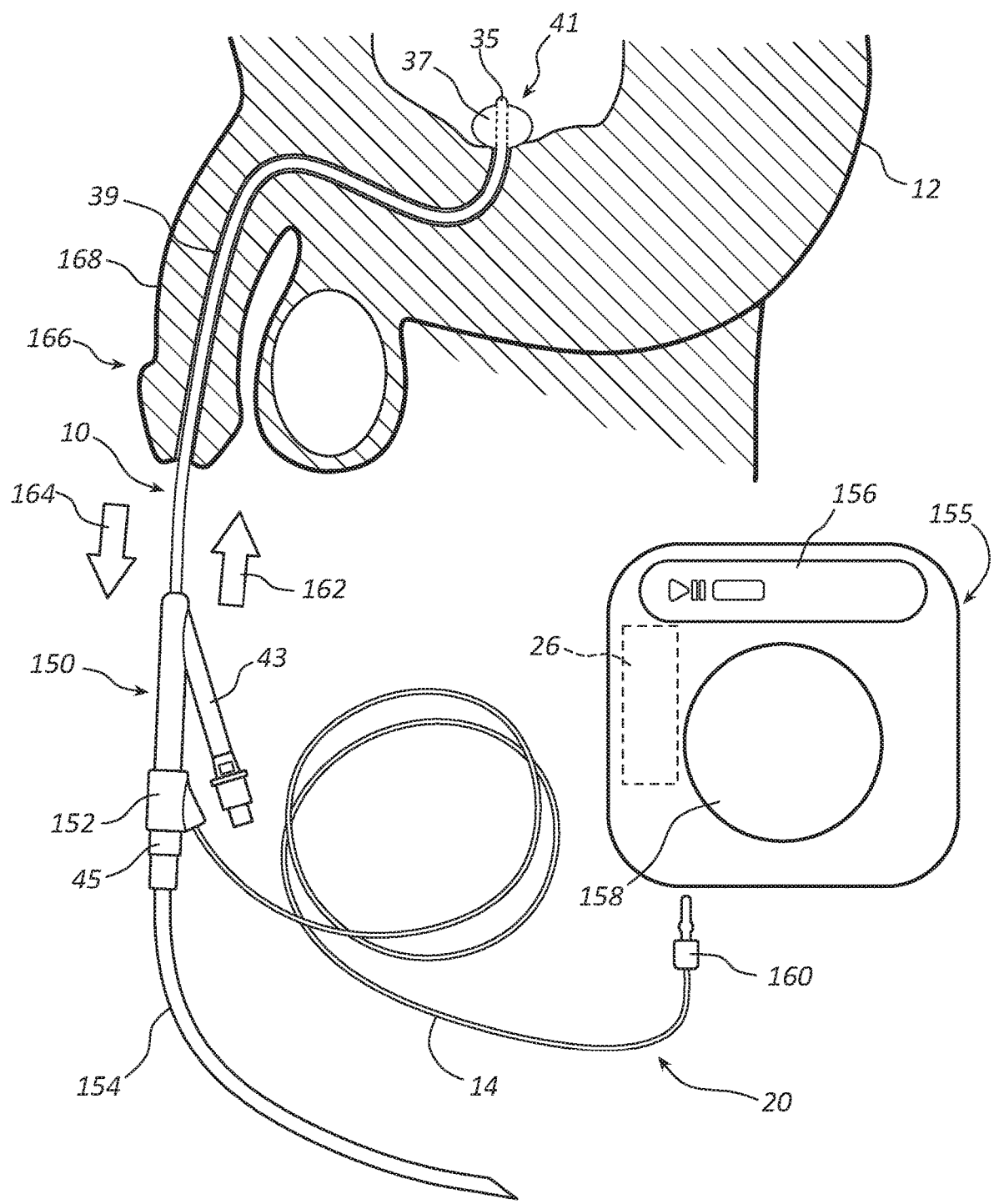
FIG. 14 is a schematic view of another exemplary embodiment of a urinary catheter positioned to drain urine and to provide therapeutic EMR within a male patient.

FIG. 14 depicts another exemplary urinary catheter 10 as positioned within a male patient 12. As shown, the urinary catheter 10 has been inserted into the patient's bladder 41 through the urethra 39 and the balloon cuff 37 has been inflated to seal the bladder 41 from leaking around the urinary catheter 10. This exemplary urinary catheter 10 comprises an elongate catheter body 36, an adapter 150, a securing sleeve 152, and a drain tube 154. The adapter 150 has an input port 43 and an output port 45. An EMR component 20 may be utilized in conjunction with the exemplary urinary catheter 10 to provide therapeutic EMR along the urethra 39 and into the bladder 41 to inactivate infectious agents and/or to promote healthy cell growth. The EMR component 20 comprises a control device 155 that houses an EMR power source 26, operational control features 156 and a display 158, an optical element 14, and an optical jack 160.

When positioned as shown in in FIG. 14, the optical element 14 has been threaded into the adapter 150 and secured by the securing sleeve 152 and urine freely drains through the elongate body 36 into the drain tube 154 to be deposited in a urine drain bag (not shown). Frequently, urinary catheters 10 are indwelling for long periods of time and consequently are a concern for the build-up and proliferation of infectious agents in, on, or around the urinary catheter 10. To provide therapeutic EMR to prevent, reduce, or eliminate the proliferation of infectious agents and/or to enhance healthy cell growth, the optical jack 160 is plugged into the control device 155 connecting the optical element 14 to the EMR power source 26 and the operational control features 156 are activated to set the frequency or frequencies, intensity, power, duty cycle, and other operational parameters, and turn on the EMR delivery into the optical element 14. The setting of the operational features and the monitoring of the parameters may be viewed on the display 158.

Figure 15:
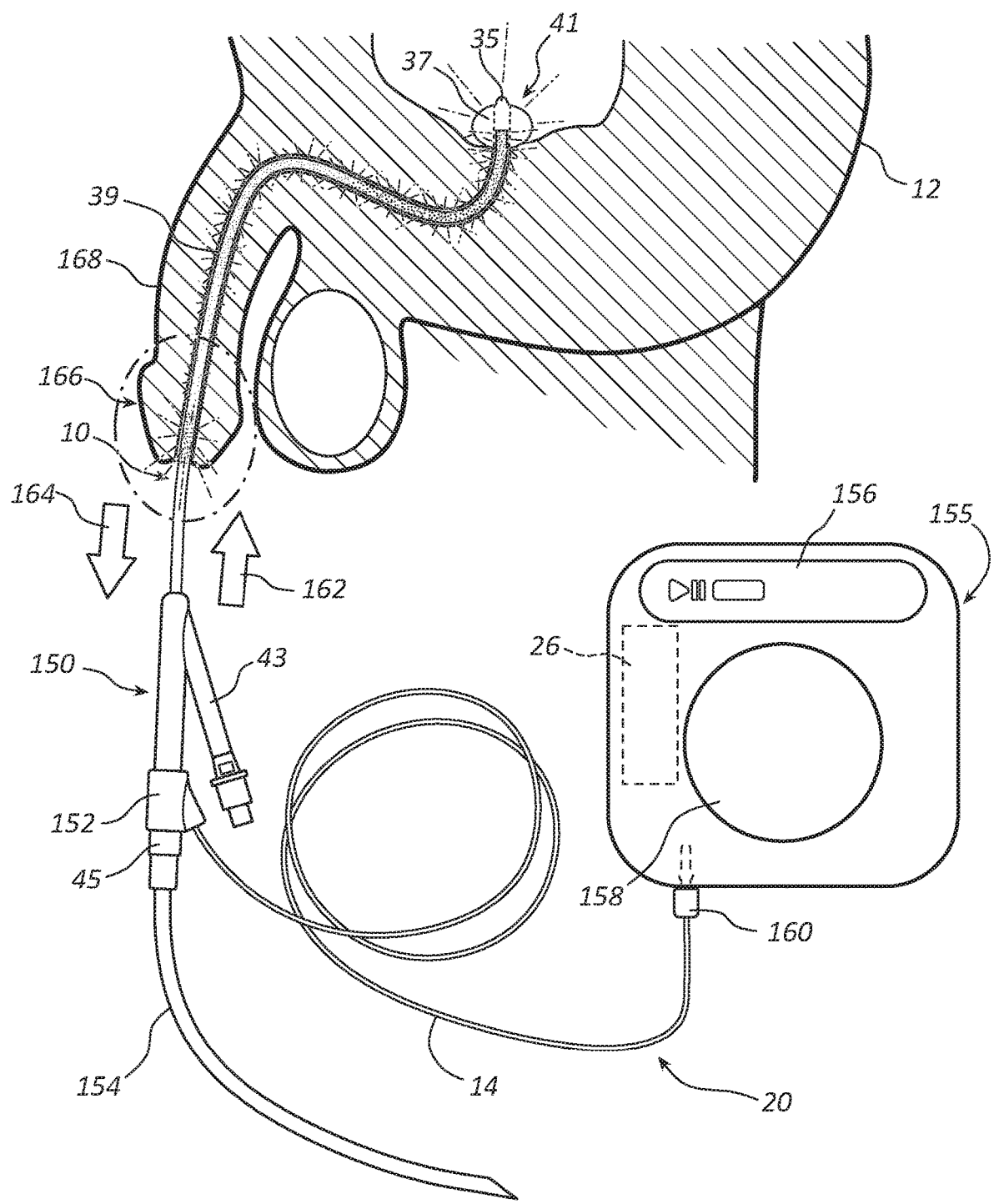
FIG. 15 is a schematic view of the urinary catheter positioned to drain urine and to provide therapeutic EMR within a male patient and illustrating an exemplary delivery of EMR with increased intensity at the meatal region of the penis and within the bladder relative to the dosing internal to the urethra.
Figure 15A:
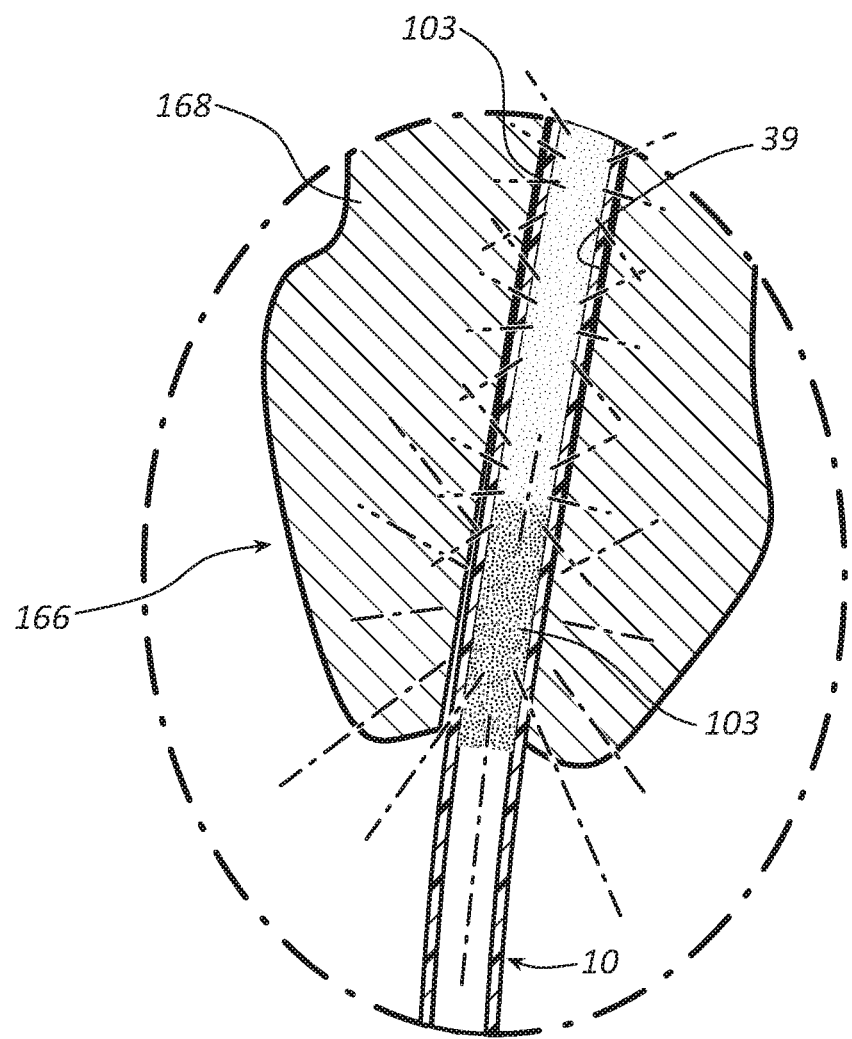
FIG. 15A is a schematic enlargement of the circle of FIG. 15 showing the radial emission portion of the optical element in the vicinity of the meatal region.

FIG. 15 is a schematic view of the urinary catheter 10 of FIG. 14 positioned to drain urine and to provide therapeutic EMR within a male patient 12 and illustrating an exemplary delivery of EMR using both controlled relative intensity and treatment region specific dosing with increased intensity at the meatal region 166 of the penis 168 and within the bladder 41 relative to a maintenance dosing internal the urethra 39. FIG. 15A is a schematic enlargement of the circle of FIG. 15 showing the radial emission portion of the optical element 14 in the vicinity of the meatal region 166. Also, because the meatal region 166 is more susceptible to infection, an increased dosing intensity may be warranted, whereas a lower intensity may be used within the urethra 39 and bladder 41 as a precautionary measure to ward off the creation of biofilm or the inception of infection.

Figure 16A:
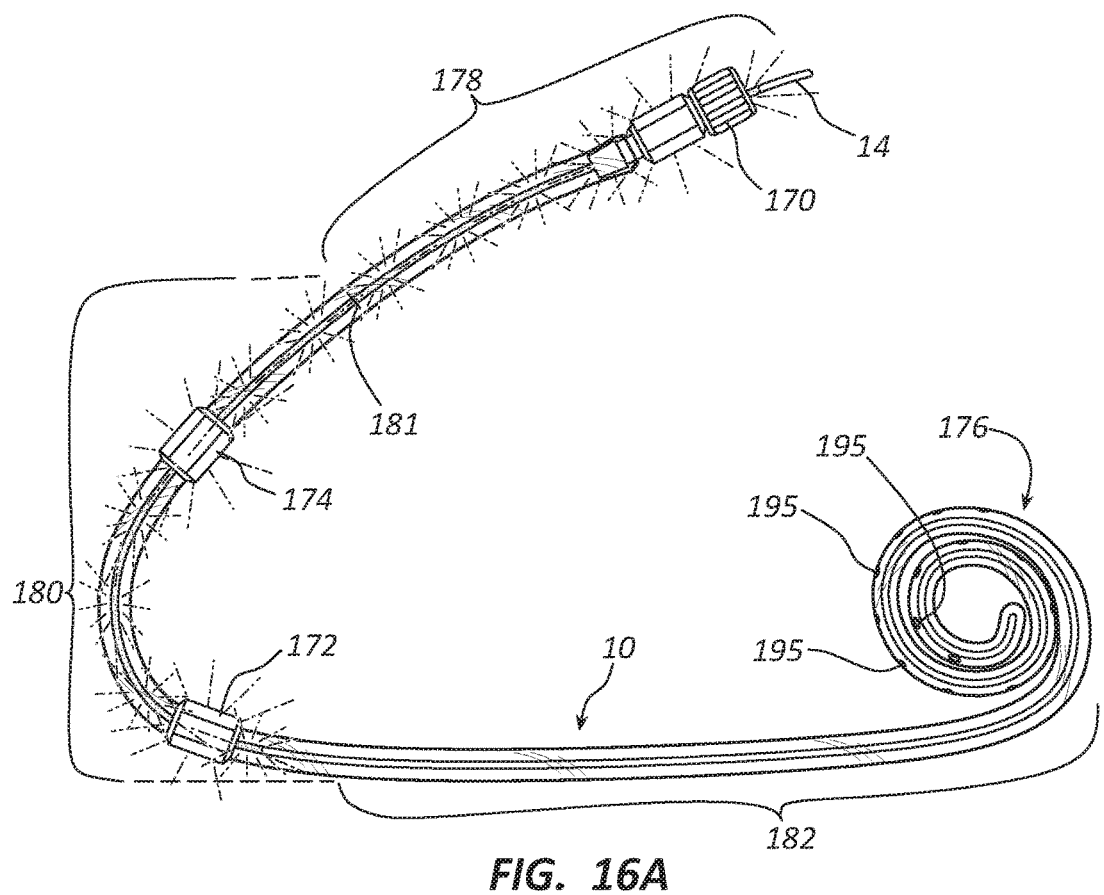
FIGS. 16A-C is a series of perspective views of an exemplary two-cuff peritoneal dialysis catheter illustrating exemplary radial EMR emissions.
Figure 16B:
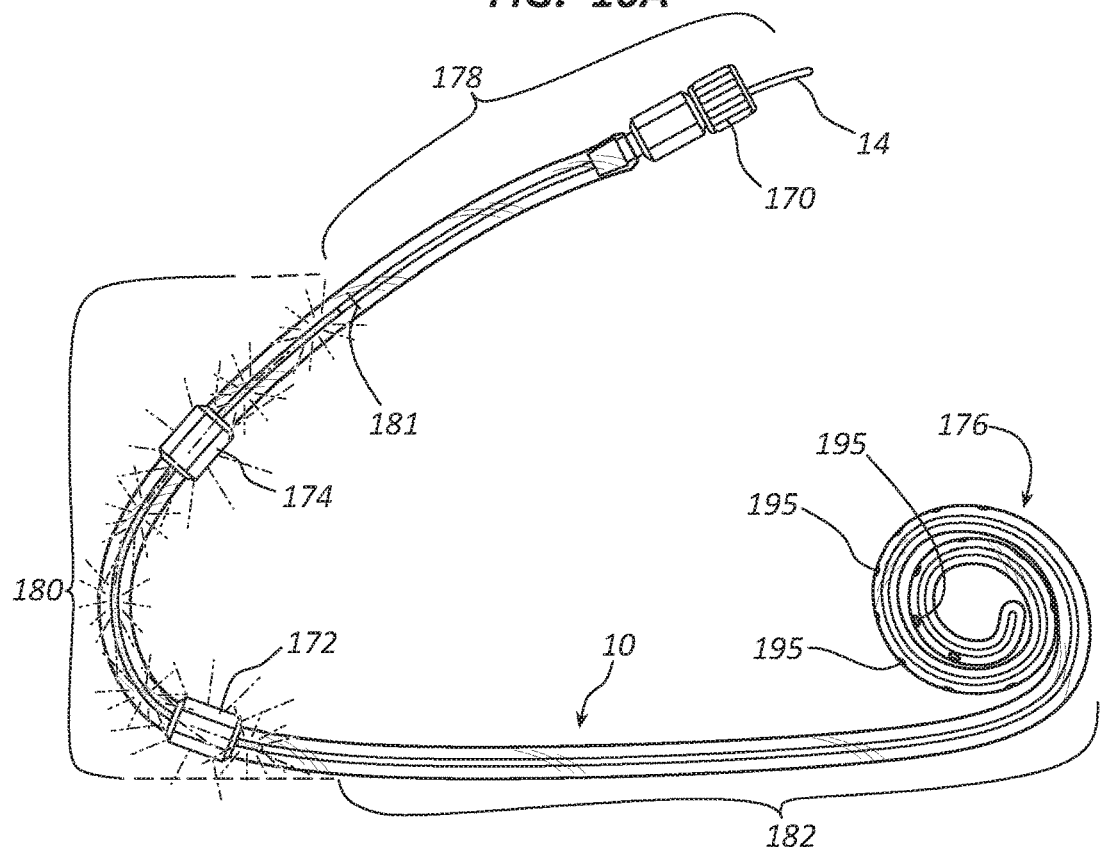
Figure 16C:
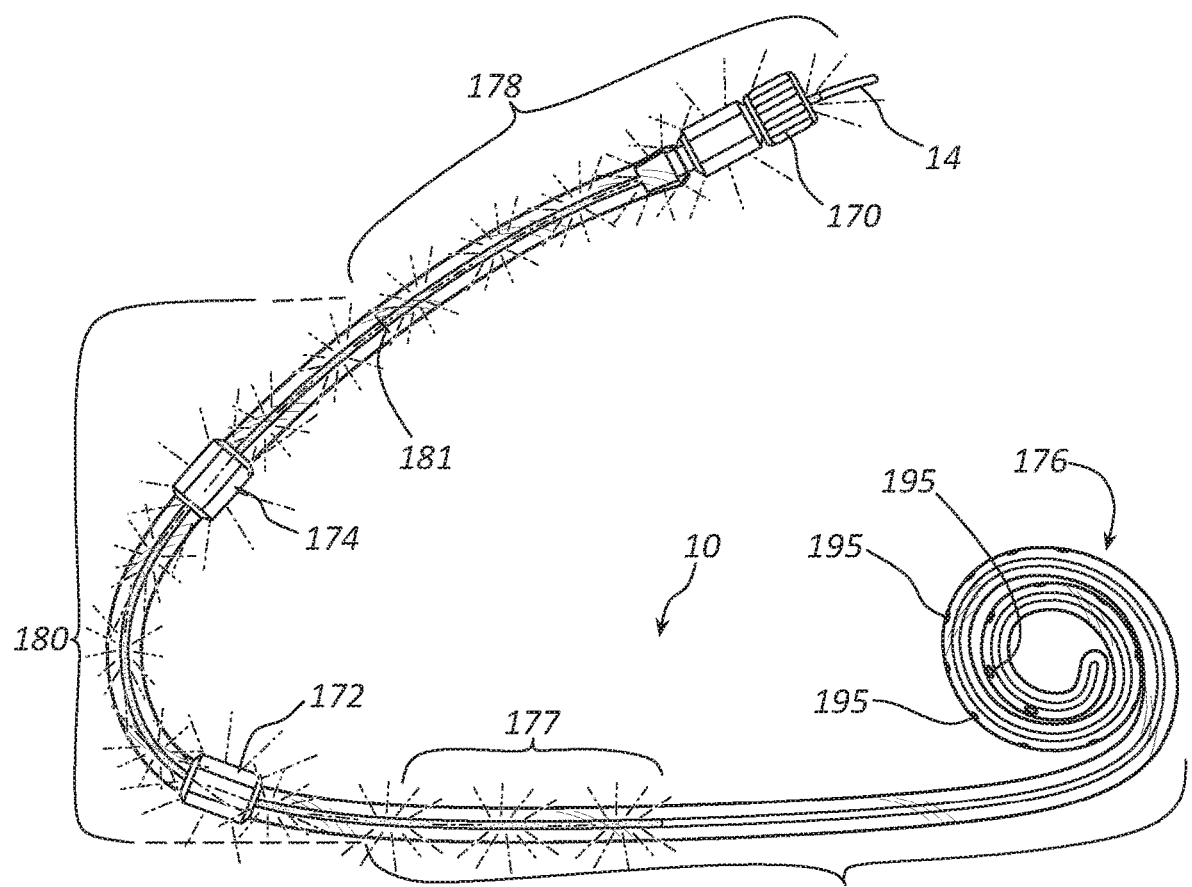

The collection of FIGS. 16A-C is a series of perspective views of an exemplary peritoneal dialysis catheter 10 illustrating exemplary radial EMIR emissions. Although both peritoneal dialysis and hemodialysis require access to a patient's body 12 via some type of dialysis access (in this case a peritoneal dialysis catheter 10), peritoneal dialysis has several advantages over hemodialysis including quality of life due to its ability to provide better patient mobility and independence, the simplicity of the dialysis access, the simplicity of use, as well as the clinical advantages of maintaining residual renal function and lower mortality in the first years after starting peritoneal dialysis. A disadvantage of peritoneal dialysis is the risk of peritonitis. Peritonitis is often the result of contamination with skin bacteria, but it may also be due to the retrograde migration of microbes on the catheter. Systemic or intra-peritoneal antibiotics may be administered, and the exchange volumes may be decreased. Although peritoneal dialysis catheter-related peritonitis may resolve with proper antibiotic therapy, delivery of EMR using both controlled relative intensity and treatment region specific dosing utilized alternatively, simultaneously, or alternately may prove to be more effective in preventing and assisting in the treatment of peritonitis. If the infection persists, catheter removal and use of hemodialysis for 4-6 weeks may be required to resolve the peritonitis. Because there is a strong association between exit-site infections and subsequent peritonitis, early, preventative delivery followed by maintenance delivery of EMIR as described herein may inhibit or eliminate exit-site infections that may lead to peritonitis.

Peritoneal refers to the lining that surrounds the organs in a patient's abdomen. That lining is called the peritoneal membrane. It forms a space called the peritoneal cavity that can hold fluid. With peritoneal dialysis, a long-term, indwelling or permanent catheter is inserted through the lining into the space around the patient's organs. Dialysis solution (also known as dialysate) is delivered through the catheter into that space. The peritoneal lining contains many blood vessels. The solution draws extra fluid, chemicals, waste out of those blood vessels and through the lining. The lining acts as a filter. The solution is left in place for a number of hours while dialysis occurs. Then the old, waste-laden solution (also known as waste dialysate) is allowed to drain out through the catheter for disposal. New, clean solution (dialysate) is immediately delivered in, filling in the space again. This process of exchanging old solution with new is called an exchange.

The two-cuff peritoneal dialysis catheter 10 shown in FIGS. 16A-C comprises a connector hub 170, line tubing 16 (not shown in FIGS. 16A-C, see FIGS. 1, 3-5, and 7A-B) connectable to the connector hub 170, a peritoneal cuff 172, a subcutaneous cuff 174, and a coiled Tenckhoff 176. This exemplary peritoneal dialysis catheter 10 is divided into three segments, an external segment 178, a tunneled segment 180 (extending from the exit site location 181 to just inside the peritoneal membrane), and an intra-peritoneal segment 182. When the two-cuff peritoneal dialysis catheter 10 is placed within the patient 12, the external segment 178 protrudes from the body of the patient 12 at the exit site location 181 and is visible, the tunneled segment 180 is tunneled through the subcutaneous tissue, the rectus muscle, and the peritoneal membrane, while the intra-peritoneal segment 182 is disposed within the peritoneal cavity. It should be understood that the exit site is the region where external segment 178 protrudes from the patient's body 12 and is depicted as an exit site location 181 on the catheter 10 (in FIGS. 16A-C) when the catheter 10 is positioned for dialysis. An optical element 14 is shown as disposed within the lumen of the 30 of the peritoneal dialysis catheter 10.

FIG. 16A is a perspective view of an exemplary two-cuff peritoneal dialysis catheter 10 showing an exemplary radial emission of EMR extending from a connector hub 170 to a point proximate to and downstream from a peritoneal cuff 172 inside of the peritoneal membrane (including radial EMR emission within the external segment 178, and the tunneled segment 180).

FIG. 16B is a perspective view of an exemplary two-cuff peritoneal dialysis catheter 10 showing the radial emission of EMR between the exit site location 181 upstream of a subcutaneous cuff 174 and a point downstream of the peritoneal cuff 172 inside of the peritoneal membrane (radial EMR emission within the tunneled segment 180).

FIG. 16C is a perspective view of an exemplary two-cuff peritoneal dialysis catheter 10 showing the radial emission of EMR between the connector hub 170 and a point downstream of the peritoneal cuff 172 and extending into a peritoneal dialysis solution region 177 during dialysis (including radial EMR emission within the external segment 178, the tunneled segment 180, and the intra-peritoneal segment 182).

Figure 17A:
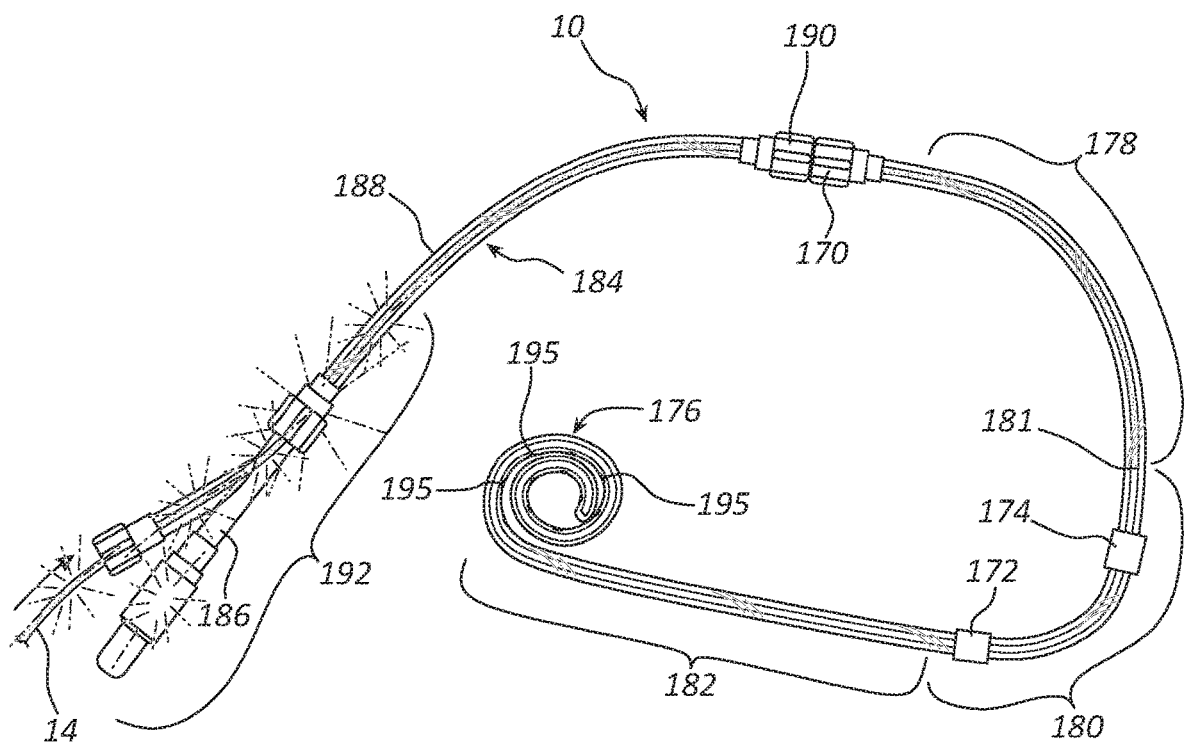
FIG. 17A is an elevation view of an exemplary two-cuff peritoneal dialysis catheter with an extension set interface showing radial EMR emission in the Y-site/transfer region only.

FIG. 17A is an elevation view of the two-cuff peritoneal dialysis catheter 10 connected to an extension set interface 184. The extension set interface 184 comprises a Y-port adapter 186, extension line tubing 188, and a connecting luer 190. Radial EMR emission is shown only in a Y-site/transfer region 192.

Figure 17B:
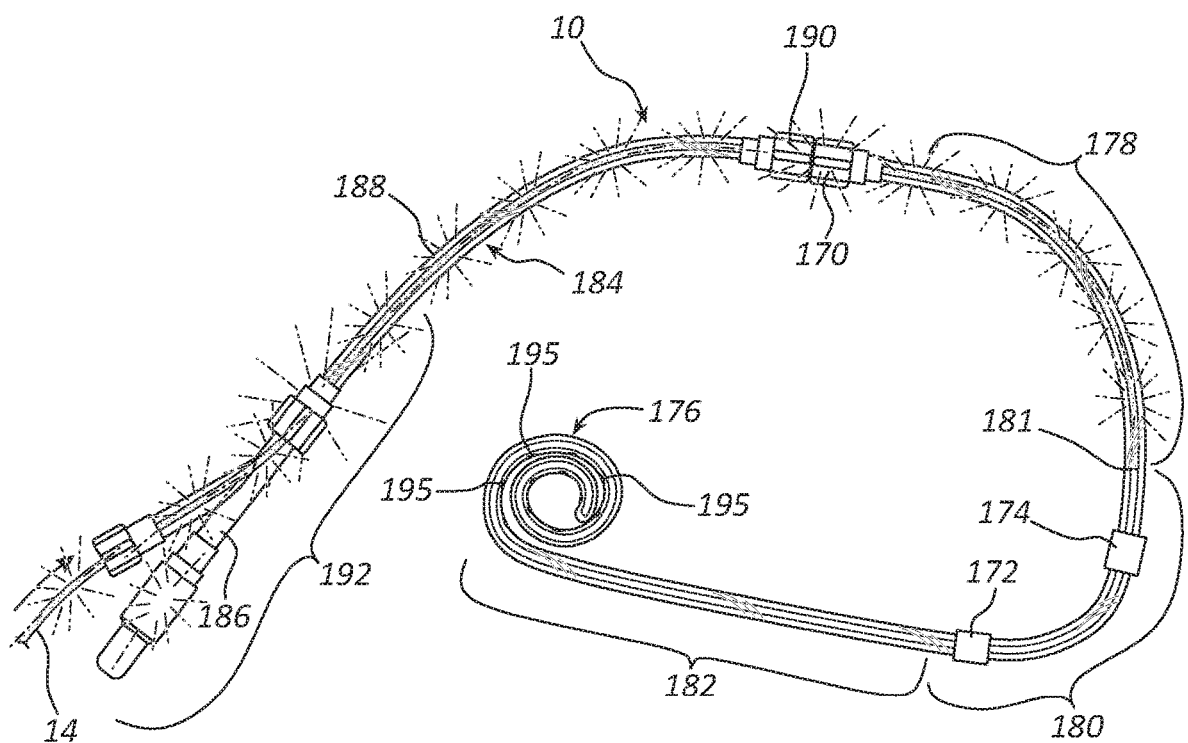
FIG. 17B is an elevation view of the two-cuff peritoneal dialysis catheter 10 connected to the extension set interface, showing radial EMR emission only exterior to the patient's body.

FIG. 17B is an elevation view of the two-cuff peritoneal dialysis catheter 10 connected to an extension set interface 184, showing radial EMR emission only exterior to the patient's body 12 (i.e., within the Y-site/transfer region 192, along the extension line tubing 188, within a connecting luer/connector hub region 194, and within the external segment 178).

Figure 17C:
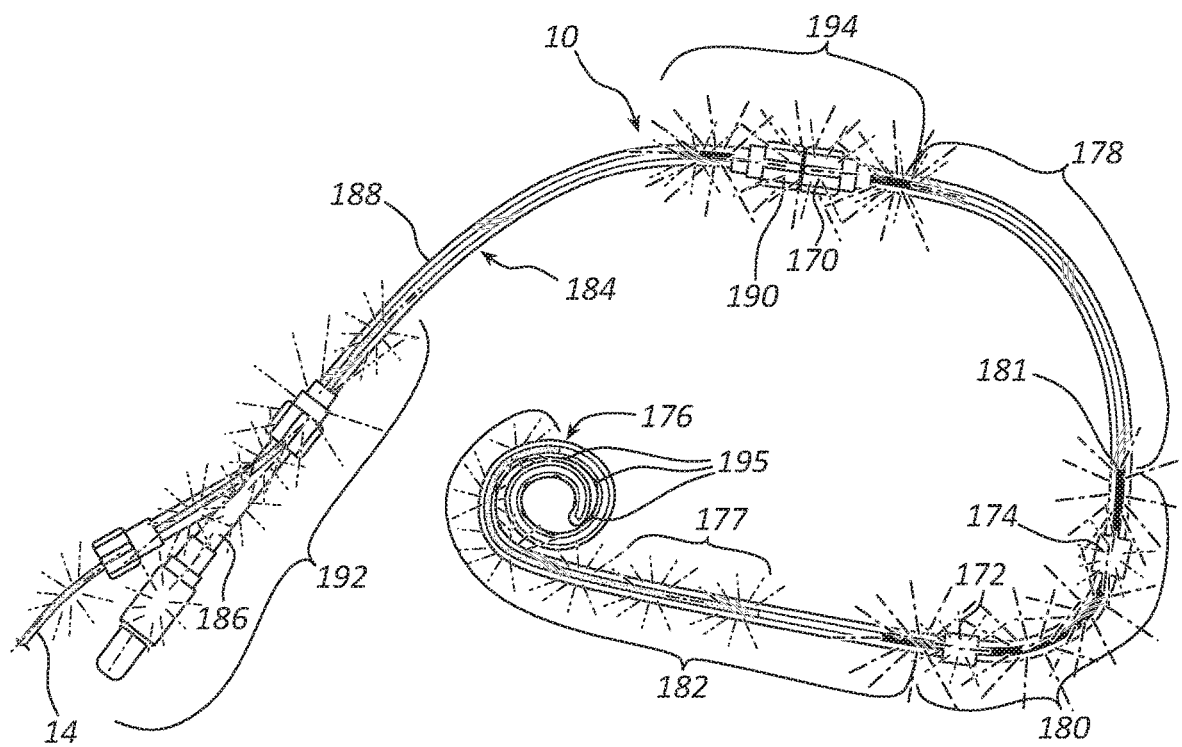
FIG. 17C is an elevation view of another exemplary two-cuff peritoneal dialysis catheter with an extension set interface showing radial EMR emission in the Y-site/transfer region, a connector hub region, a tunneled segment, and within the peritoneal dialysis solution region.

FIG. 17C is an elevation view of the two-cuff peritoneal dialysis catheter 10 connected to an extension set interface 184 but showing radial EMR emission within the Y-site/transfer region 192, the connecting luer/connector hub region 194, the tunneled segment 180, and the intra-peritoneal segment 182. This exemplary embodiment provides additional radial EMR emission in exterior regions susceptible to contamination-caused infections; namely, the Y-site/transfer region 192 and the connecting luer/connector hub region 194.

Figure 17D:
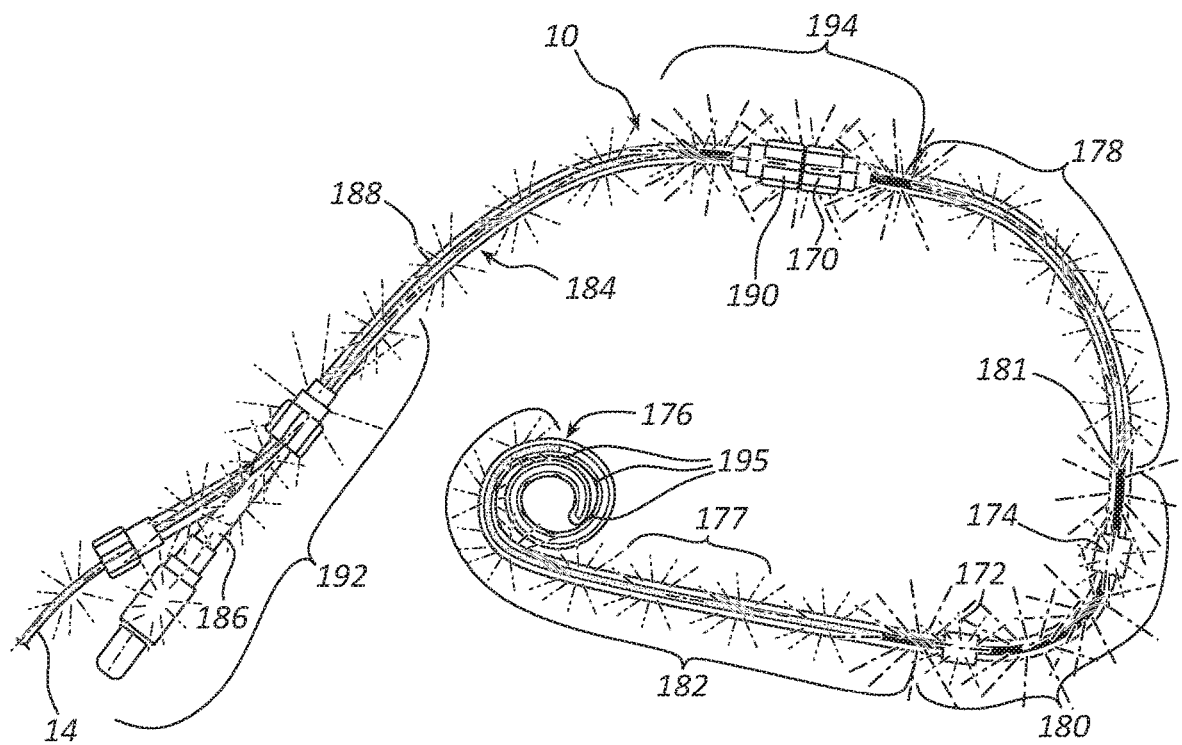
FIG. 17D is an elevation view of still another exemplary two-cuff peritoneal dialysis catheter with an extension set interface showing radial EMR emission in the Y-site/transfer region, a connector hub region, a tunneled segment, and within the peritoneal dialysis solution region extending into the coiled Tenckhoff.

Similarly, FIG. 17D shows an elevation view of the two-cuff peritoneal dialysis catheter 10 connected to an extension set interface 184 but showing radial EMR emission within the Y-site/transfer region 192, the connecting luer/connector hub region 194, the tunneled segment 180, the intra-peritoneal segment 182 and into the coiled Tenckhoff 176. This exemplary embodiment demonstrates that radial EMR emission may be delivered over the full extent of the catheter 10, including exterior regions susceptible to contamination-caused infections and regions within the patient's body 12. In combination with the other figures, FIG. 17D demonstrates that any combination of regions along the length of the catheter 10 may have radial emitted EMR on or off as desired to employ controlled relative intensity and/or treatment region specific application of the therapeutic doses.

Also, by extending the optical element 14 into the coiled Tenckhoff 176 as shown in FIG. 17D, the optical element 14 may prevent occlusion of holes 195 and/or tissue adhesion to the catheter 10. To avoid uncoiling the coiled Tenckhoff 176, a smaller diameter optical element 14 fiber may be required (at least in the region of the optical fiber that extends into the coiled Tenckhoff 176).

Figure 18A:
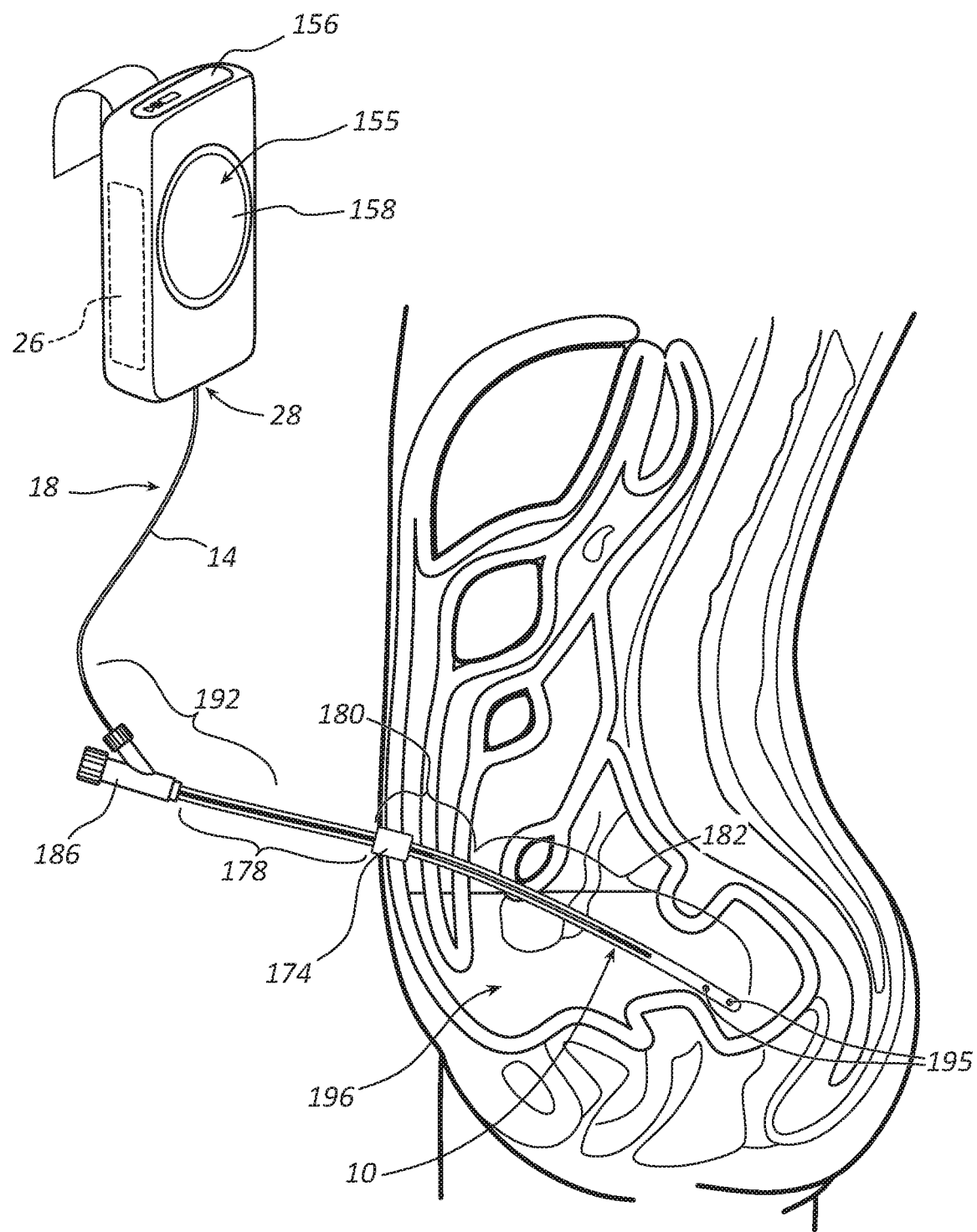
FIG. 18A is a schematic view of an exemplary embodiment of a single-cuff peritoneal dialysis catheter as inserted within a female patient's body.

FIG. 18A is a schematic view of another exemplary embodiment of a peritoneal dialysis catheter 10 as inserted within a female patient's body 12. This exemplary embodiment shows a single-cuff peritoneal dialysis catheter 10 providing no radial EMR emission because to the EMR is turned off.

Figure 18B:
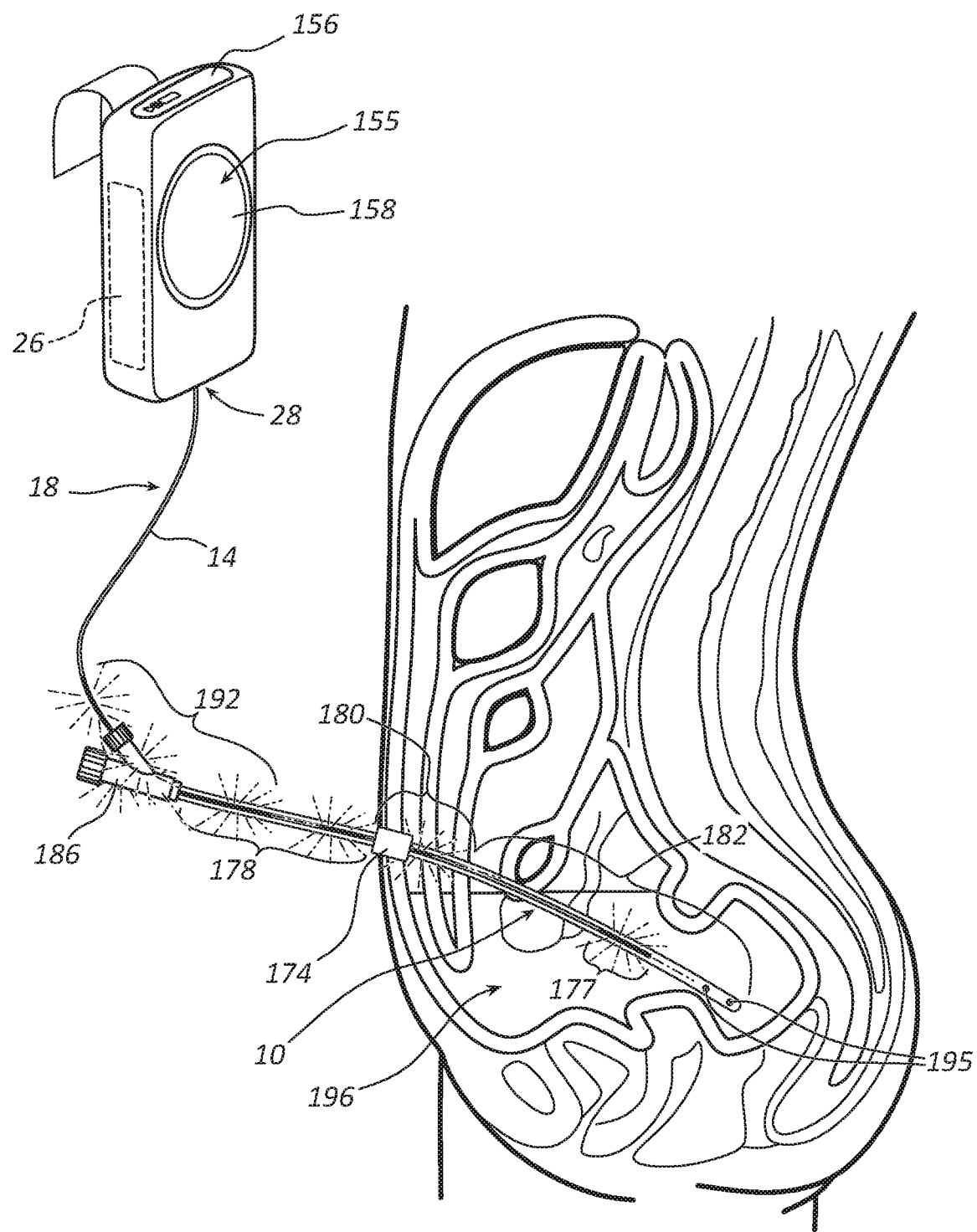
FIG. 18B is a schematic view of another exemplary embodiment of a single-cuff peritoneal dialysis catheter as inserted within a female patient's body showing radial EMR emission received from a point downstream of the EMR source to just downstream of the peritoneal cuff and within the peritoneal dialysis solution region.

FIG. 18B is a schematic view of another exemplary embodiment of a single-cuff peritoneal dialysis catheter 10 inserted within a female patient's body 12. This exemplary embodiment provides radial EMR emission received from a point downstream of the EMR control device 155 to just downstream of the peritoneal cuff 172 (i.e., through the Y-site/transfer region 192, the exterior segment 178, and the tunneled segment 180) and within the peritoneal dialysis solution 196 at a peritoneal dialysis solution region 177.

Figure 19:
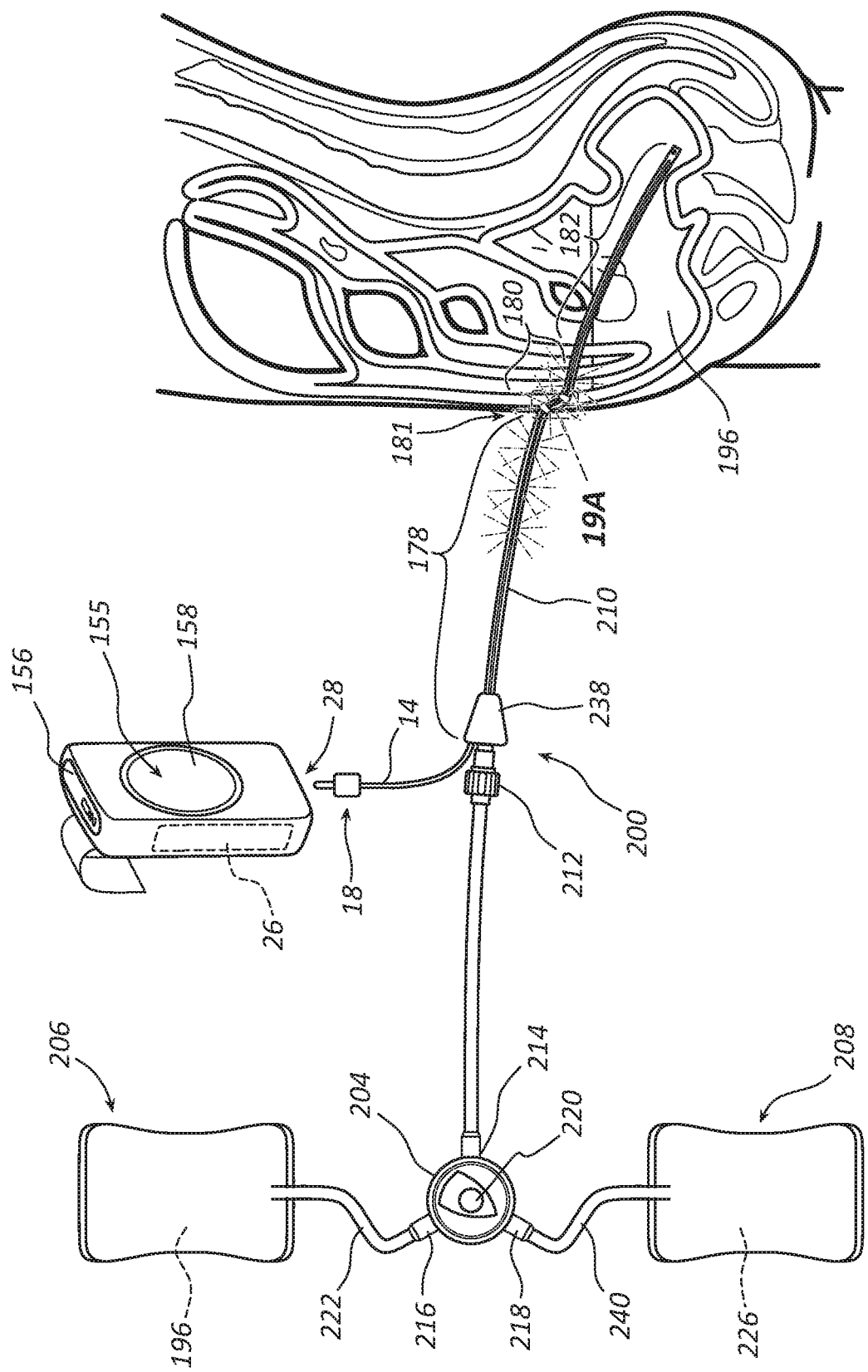
FIG. 19 is a schematic view of an exemplary embodiment of a peritoneal dialysis system showing dialysate supply and return bags and an inset area enlarged as FIG. 19A.

FIG. 19 is a schematic view of an exemplary embodiment of a peritoneal dialysis system 200 showing dialysate supply and return bags. The schematic depiction is a basic representation of peritoneal dialysis systems 200. The use of this basic representation is not intended to be limiting of the scope of the present invention; rather, this disclosure contemplates and considers the use of the disclosed invention within more sophisticated peritoneal dialysis systems, known and yet to be developed, to be within the scope of the present invention. Armed with this disclosure, those skilled in the art will understand where, when, and how the delivery of EMR as disclosed herein may be used in more sophisticated peritoneal dialysis systems, known and yet to be developed.

The basic peritoneal dialysis system 200 (depicted in FIG. 19) comprises dialysis access 201 via a catheter 10, a fluid extension line 202, a dialysate exchange switch 204, a dialysate supply bag 206, and a waste dialysate retrieval bag 208. As described with reference to FIGS. 16A-C, 17A-D, and 18A-B, the catheter 10 (also referred to a PD catheter 210) has an external segment 178, a tunneled segment 180, an intra-peritoneal segment 182, a coupling end and a distal end. The coupling end of the PD catheter 210 is connected to the fluid extension line 202 via an extension connector 212. The fluid extension line 202 is connected to the dialysate exchange switch 204. The dialysate exchange switch 204 has an extension line portal 214, a dialysate inlet 216, a waste dialysate outlet 218 and an exchange selector 220 for selecting fluid flow paths. The dialysate supply bag 206 contains dialysate 196 (also referred to as dialysis solution 196) and is connected to the dialysate exchange switch 204 via a feed line 222 and the dialysate inlet 216, establishing a dialysate flow path (when the exchange selector 220 is moved to select dialysate flow) from the dialysate supply bag 206 into the feed line 222, through the dialysate exchange switch 204, into and through the fluid extension line 202, to the PD catheter 210 for delivery into the patient's body 12.

With peritoneal dialysis, a long-term, indwelling or permanent catheter 10 (a PD catheter 210 in particular) is or may have already been inserted through the peritoneal lining 224 into the abdominal space 177 (sometimes referred to as the peritoneal dialysis solution region 177) around the patient's organs. Dialysis solution 196 (also referred to as dialysate 196) is delivered in the direction of Arrow B from the dialysate supply bag 206 through the PD catheter 210 into that abdominal space 177. The peritoneal lining 224 contains many blood vessels. The dialysate 196 draws extra fluid, chemicals, waste out of those blood vessels and through the peritoneal lining 224. Hence, the peritoneal lining 224 acts as a filter. The dialysate 196 is left in place for a number of hours while dialysis occurs. Then the old, waste-laden dialysis solution 226 (sometimes referred to as waste dialysate 226) is allowed to drain out through the catheter 10 for disposal. New, clean solution (dialysate) 196 is immediately delivered in, filling in the abdominal space 177 again. This process of exchanging old (waste dialysate) solution 226 with new dialysate 196 is called an exchange.

Figure 19A:
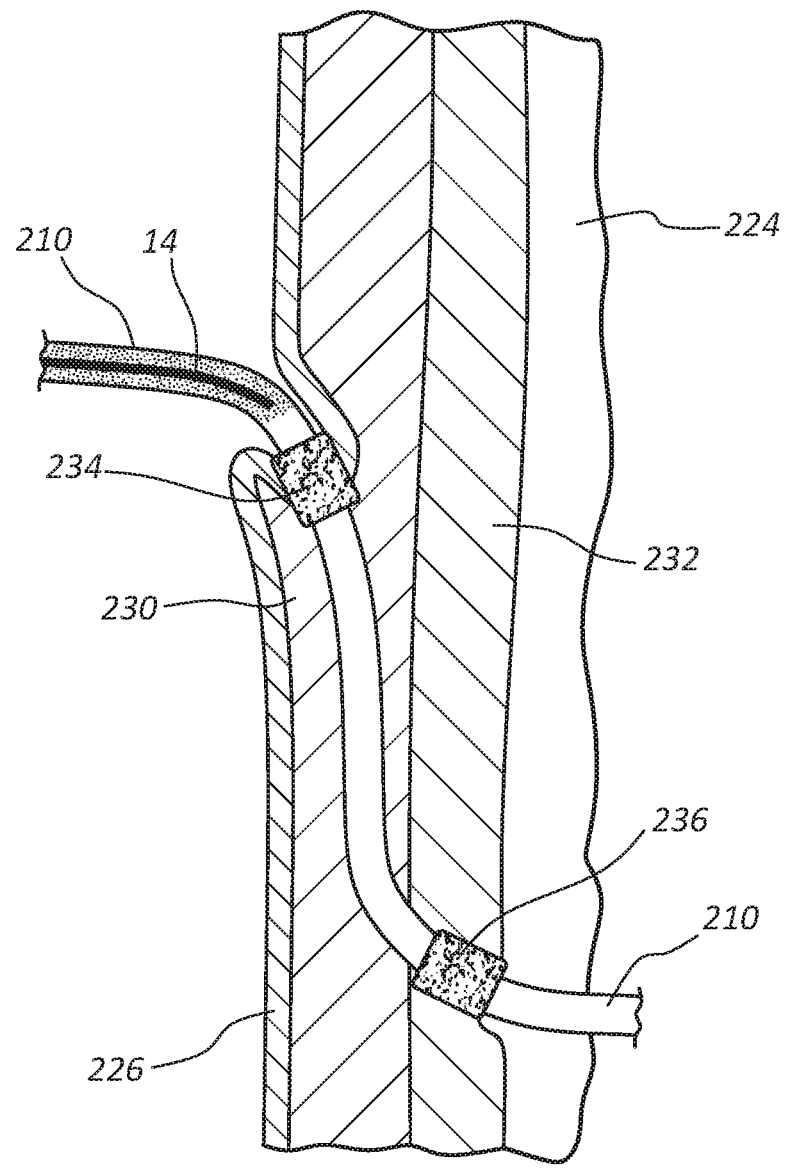
FIG. 19A is an enlargement of the inset area identified in FIG. 19 showing a subcutaneous cuff and a deep abdominal wall cuff that seal the passage of the peritoneal dialysis catheter into the peritoneum.

FIG. 19A shows the inset area identified in FIG. 19 enlarged to show the tunneled segment 180 of the PD catheter 210 in more detail. The PD catheter 210 is tunneled through the skin 228, the subcutaneous layer 230, the abdominal wall 232, and the peritoneal lining 224. The PD catheter 210 has a subcutaneous cuff 234 and a deep abdominal wall cuff 236 that seal the passage of the PD catheter 210 into the abdominal space 177. As noted in FIG. 18A, for example, sometimes a single subcutaneous cuff 174 may be used.

Returning to FIG. 19, the peritoneal dialysis system 200 has been enhanced by adding an EMR conduction system 18 comprising a control device 155 and an optical element 14. This enhancement of the peritoneal dialysis system 200 may be part of a kit that includes the peritoneal dialysis system 200 and the EMR conduction system 18 (whether the EMR conduction system 18 is permanently connected to the peritoneal dialysis system 200 or removably insertable into the peritoneal dialysis system 200). Or, the EMR conduction system 18 may be retrofitted with an existing peritoneal dialysis system 200. As depicted, the optical element 14 of the EMR conduction system 18 is introduced into the external segment 178 of the PD catheter 210 through an introducing adapter 238 that facilitates the passage of the optical element 14 into the lumen of the PD catheter 210 without impairing the free flow of fluid through the PD catheter 210.

The control device 155 houses the EMR power source 26, operational control features 156, a display 158, and a female optical jack port (not shown) for receiving an optical jack 160. Together, the female optical jack port and the optical jack 160 serve as the coupling element 28 so that the desired EMR light is delivered from the EMR power source 26 into the optical element 14 (in this case an optical fiber). The optical jack 160 is shown as detached for description purposes only, When the optical jack is connected to the control device and the optical element 14 is disposed within the lumen of the PD catheter 210 as shown, the therapeutic, non-ultraviolet EMR may be delivered where desired. The depiction in FIG. 19 shows radial delivery of EMR within the external segment 178 and the tunneled segment 180 of the PD catheter 210.

Of course, it should be understood that the invention of this disclosure as described herein may provide radial emission of the EMR light in the locations, at the intensities, and with the controlled relative intensity and/or treatment region specific application of therapeutic doses of the EMR light.

As depicted in FIG. 19, the dialysate exchange switch 204 is set for the waste cycle where waste dialysate 226 is withdrawn from the abdominal space 177 in the direction of Arrows C, through a dialysis access 201 such as the PD catheter 210 and the extension connector 212, into the fluid extension line 202, into the dialysate exchange switch 204 via the extension line portal 214, and out through the waste dialysate outlet 218 into a drainage line 240 and then the waste dialysate retrieval bag 208 for disposal.

Figure 20:
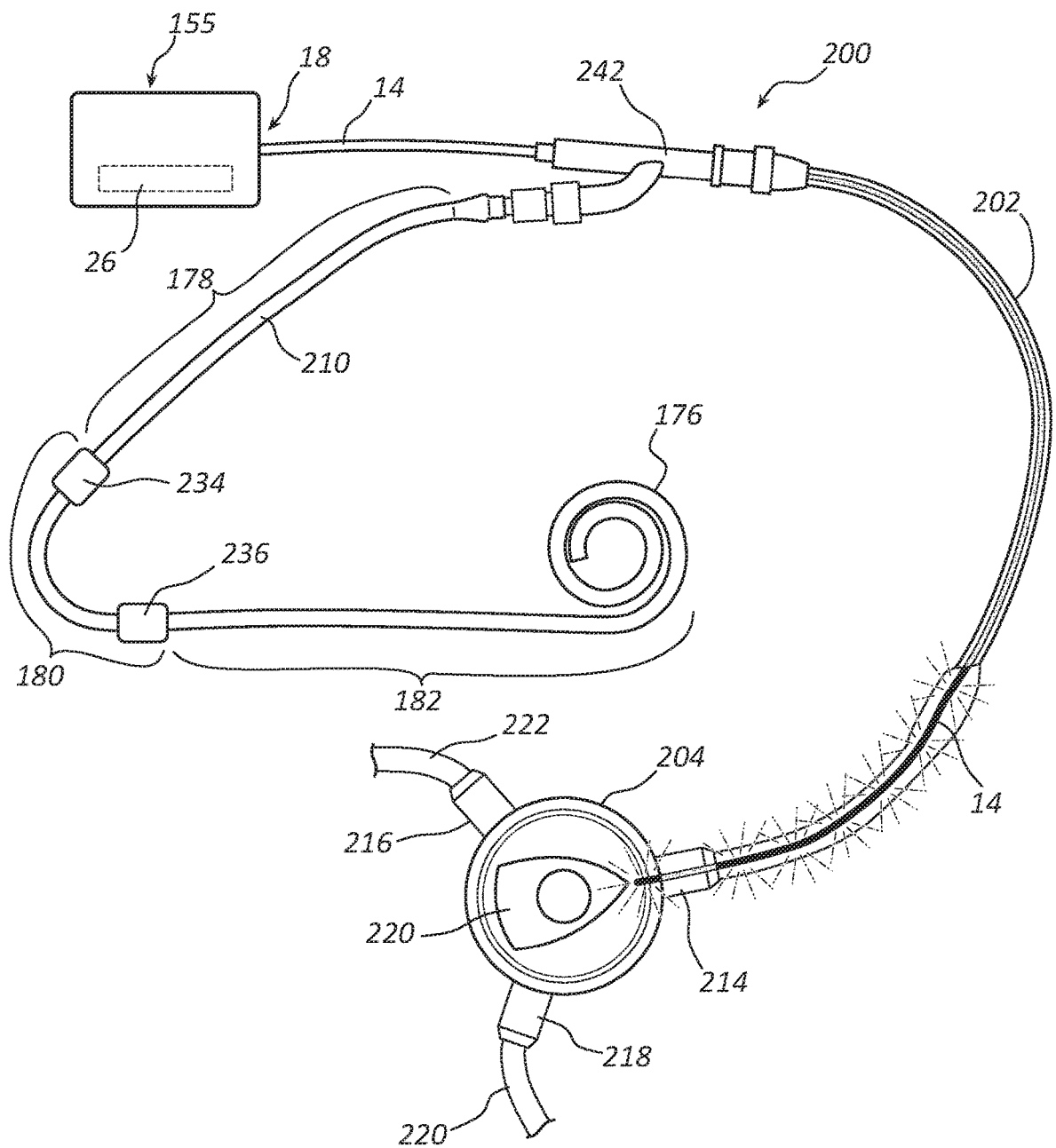
FIG. 20 is a schematic view a portion of an exemplary embodiment of a peritoneal dialysis system showing the emission of EMR at a treatment location in a PD extension catheter and into a dialysate exchange switch.

FIG. 20 is a schematic depiction of another exemplary embodiment of a portion of the peritoneal dialysis system 200 (omitting the dialysate supply bag 206 and the waste dialysate retrieval bag 208) showing the emission of EMR light at a treatment location within the fluid extension line 202 (sometimes called a PD extension catheter) and into the dialysate exchange switch 204 in the vicinity of the extension line portal 214. This exemplary embodiment utilizes a different introducing Y-connector 242 and a PD catheter 210 having a coiled Tenckhoff 176. This depiction illustrates the versatility of the EMR conduction system 18 in that it may also be used to sterilize the fluid extension line 202 and the dialysate exchange switch 204 independent of delivering EMR to the PD catheter 210 by merely switching out the introducing adapter 238 for the introducing Y-connector 242 and inserting the optical element 14 into the fluid extension line 202. Also, the therapeutic EMR light may be delivered before dialysis begins, during dialysis, during waste dialysate 226 retrieval, and/or after the dialysis treatment is complete.

Figure 21:
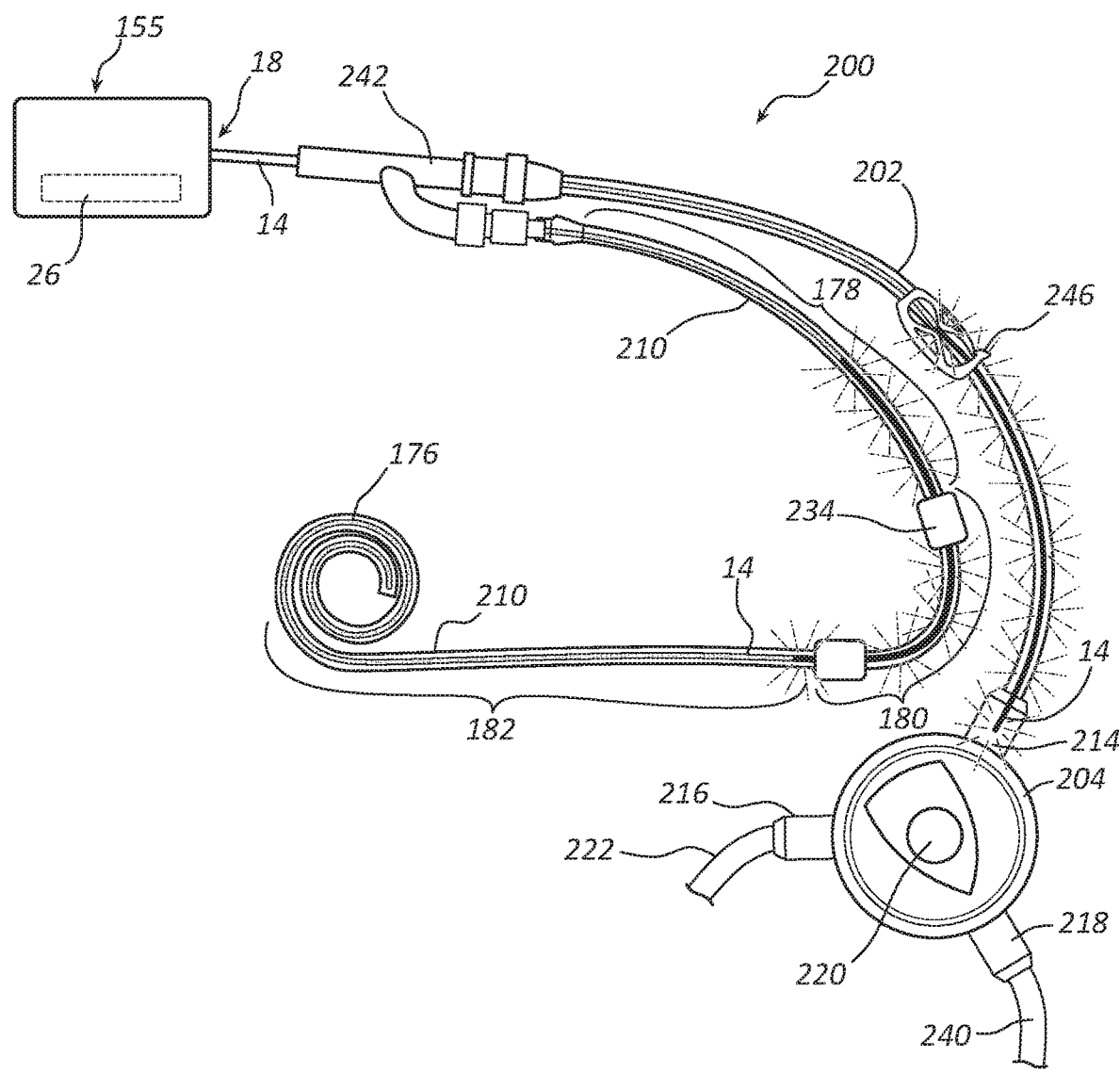
FIG. 21 is a schematic view a portion of another exemplary embodiment of a peritoneal dialysis system depicting dual EMR delivery.

FIG. 21 is a schematic depiction of another exemplary embodiment of a portion of the peritoneal dialysis system 200 (omitting the dialysate supply bag 206 and the waste dialysate retrieval bag 208) showing dual EMR delivery from a single control device 155. With this embodiment, two optical elements 14 extend from the single control device 155 and into a dual introducing Y-connector 244, one optical element 14 being inserted into the fluid extension line 202, and the other optical element 14 being inserted into the PD catheter 210. The EMR light delivered may be the same for each optical element 14. In that case, a single coupling element 28 may be used and the split into two optical elements may be outside of the coupling element 28 (for example within the dual introducing Y-connector 244). Also, the EMR light delivered into the respective optical elements 14 may differ for each optical element 14. In that case, separate coupling elements 28 may be used and the EMR light delivered may be provide alternatively, alternatingly, or simultaneously, and with differing frequencies, intensities, and dosages so to provide controlled relative intensity and/or treatment region specific application of therapeutic doses of the EMR light where and when desired within the peritoneal dialysis system 200.

Specifically, FIG. 21 shows simultaneous EMR delivery into the fluid extension line 202 and the PD catheter 210. Also, depicted is a line clamp 246 used to occlude the fluid extension line 202 so that fluid (waste dialysate 226, as depicted) will not drain through the fluid extension line 202 into the waste dialysate retrieval bag 208 during the dialysis process once the peritoneal dialysis solution region 177 is filled and before the waste cycle. As depicted, the portion of the fluid extension line 202 between the line clamp 246 and the dialysate exchange switch 204 is being sterilized by the EMR light radially emitting from the optical element 14.

Figure 22:
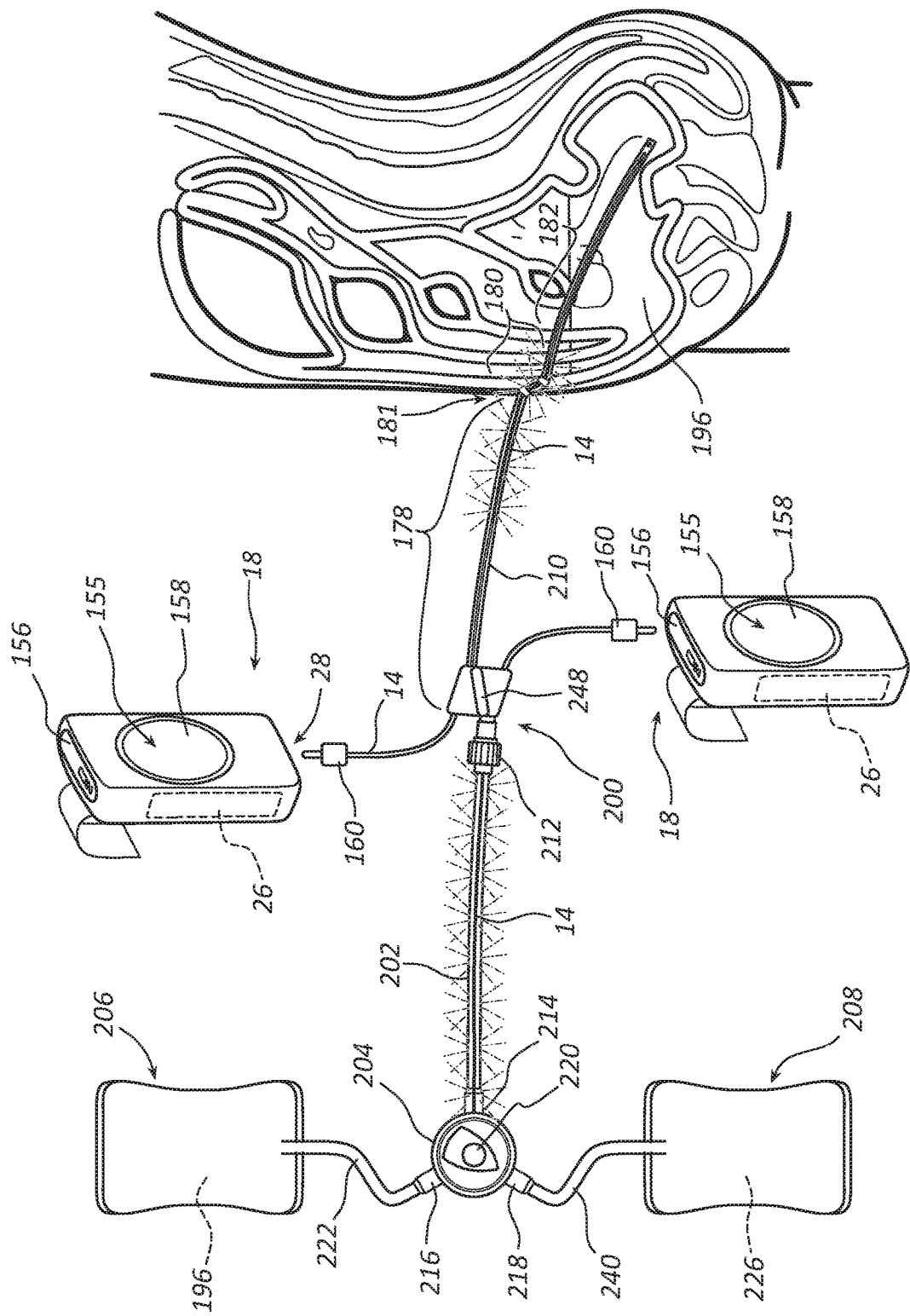
FIG. 22 is a schematic view still another exemplary embodiment of a peritoneal dialysis system depicting another exemplary dual EMR delivery using two EMR sources.

Still another exemplary embodiment of a peritoneal dialysis system 200 is depicted schematically in FIG. 22 showing a dual EMR delivery using two EMR sources. With this embodiment, two optical elements 14 extend from separate control devices 155 and into a dual introducing multi-direction adapter 248, one optical element 14 being inserted into the fluid extension line 202, and the other optical element 14 being inserted into the PD catheter 210. The EMR light delivered may be the same for each optical element 14. However, separate control devices 155 make it possible to have each optical element 14 to operate totally independent of the other optical element 14. Hence, the EMR light delivered may be provided alternatively, alternatingly, or simultaneously, and with differing frequencies, intensities, and dosages so to provide controlled relative intensity and/or treatment region specific application of therapeutic doses of the EMR light where and when desired within the peritoneal dialysis system 200. Specifically, FIG. 22 shows simultaneous EMR delivery into the fluid extension line 202 and the PD catheter 210; however, each may be emitting EMR light with different frequencies, intensities, and dosages.

Figure 23:
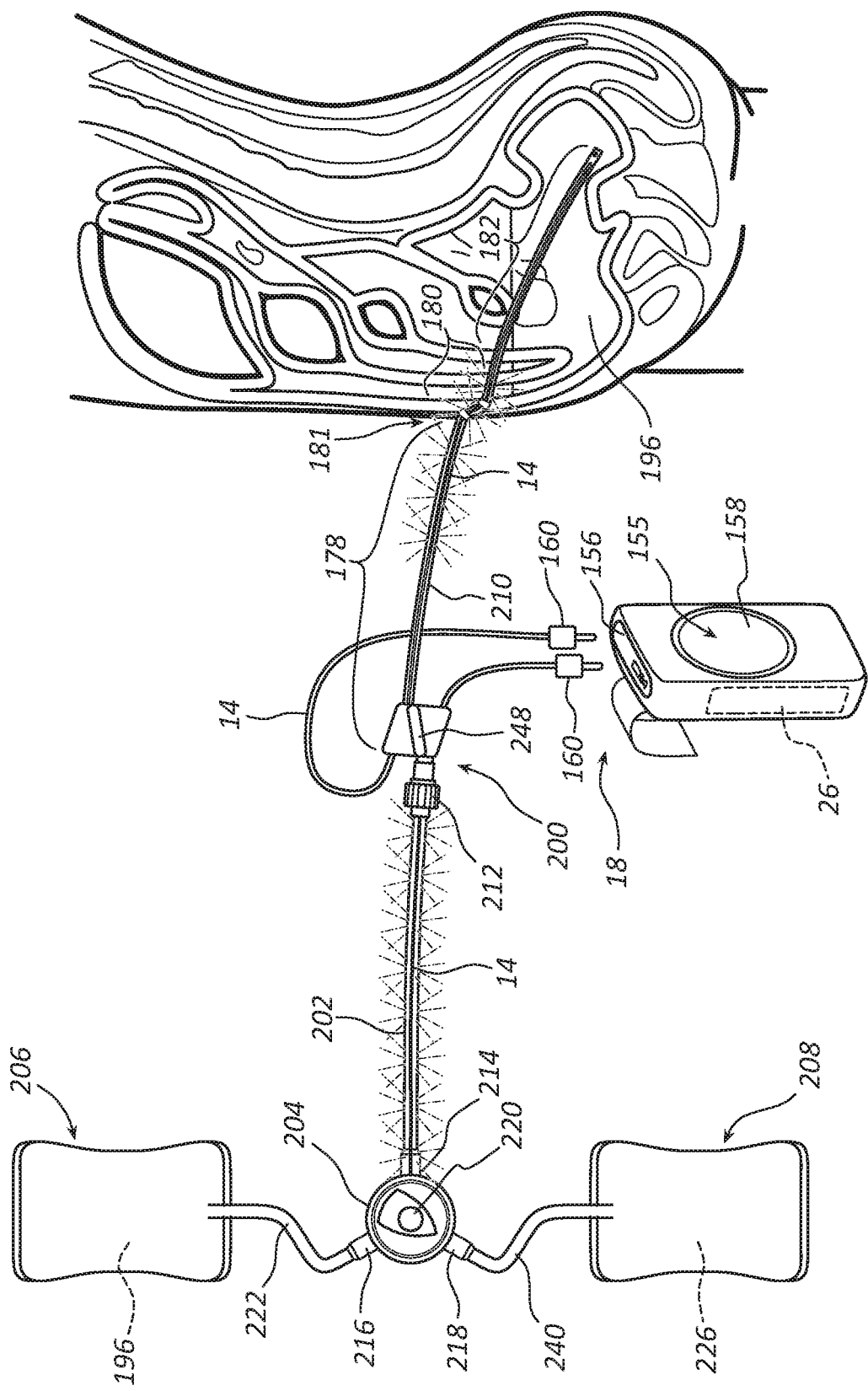
FIG. 23 is a schematic view of yet another exemplary embodiment of a peritoneal dialysis system depicting dual EMR delivery using a single EMR source.

Yet another exemplary embodiment of a peritoneal dialysis system 200 is depicted in FIG. 23 and shows dual EMR delivery (similar to the configuration in FIG. 22) using a single EMR source. With this embodiment, two optical elements 14 extend from separate optical jacks 160 connected (for clarity, the optical jacks 160 are shown as detached) to a single control devices 155 and into a dual introducing multi-direction adapter 248, one optical element 14 being inserted into the fluid extension line 202, and the other optical element 14 being inserted into the PD catheter 210. Again, the EMR light delivered may be the same for each optical element 14. In this instance, however, a single control device 155 capable of delivering differing EMR light to each optical element, makes it possible to have each optical element 14 operate independent of the each other. Again, the EMR light delivered may be provided alternatively, alternatingly, or simultaneously, and with differing frequencies, intensities, and dosages so to provide controlled relative intensity and/or treatment region specific application of therapeutic doses of the EMR light where and when desired within the peritoneal dialysis system 200. Specifically, FIG. 23 also shows simultaneous EMR delivery into the fluid extension line 202 and the PD catheter 210; however, each may be emitting EMR light with different frequencies, intensities, and dosages.

Hemodialysis is a treatment that removes wastes and extra fluid from a patient's blood when the patient's own kidneys have failed. Before hemodialysis can be done, a connection must be made to the blood inside the patient's blood vessels. One of a several different types of dialysis access 201, such as a vascular access, serves as a way to reach a patient's blood for hemodialysis. The dialysis access 201 allows the patient's blood to travel through soft tubes (such as extension tubing, catheters, and the like) to the dialysis machine where it is cleaned as it passes through a special filter acting as an artificial kidney, called a dialyzer. Generally, there are three principal different types of dialysis access 201 used for hemodialysis. They are called a fistula, a graft, and a catheter (or hemodialysis catheter). There pros and cons of each one. Typically, a special surgeon with hemodialysis access experience will determine, recommend, and/or select which type of dialysis access 201 will be appropriate for each patient.

To get blood into the dialyzer, a dialysis access 201, or entrance, into the patient's blood vessels must be made. Typically, this is done with minor surgery, usually to an arm or leg or elsewhere depending on where the dialysis access 201 is most appropriate for the patient.

For hemodialysis, catheters are generally used as a temporary dialysis access 201, in case of an emergency need for dialysis or while waiting for dialysis access surgery to create either a fistula or a graft and for the fistula or graft to mature, but sometimes catheters provide permanent dialysis access 201. Hemodialysis catheters are soft tubes placed into a large vein in the neck or sometimes elsewhere such as in the leg.

An arteriovenous fistula, a dialysis access 201 made by joining an artery and a vein in the patient's arm (or leg), is generally considered advantageous because it lasts longer and has fewer problems such as infections and clotting. An arteriovenous fistula should be placed several months before it is needed to start dialysis. This allows the fistula enough time to be ready for when treatment is needed and starts. A fistula usually takes one to four months to "mature" or enlarge before it can be used. However, some patients may not be able to receive a fistula because their blood vessels are not strong enough.

An arteriovenous graft is a dialysis access 201 made by joining an artery to a closely proximate vein. Minor surgery is done using an artificial tube between the vein and the nearby artery. An arteriovenous graft is usually put inside the bend of a patient's arm or in their upper arm. Sometimes, it may be placed in a patient's leg or chest wall. The arteriovenous graft generally needs to be in place at least two weeks after surgery before it can be used. Each of these dialysis access 201 options are susceptible to infectious agents.

Figure 24:
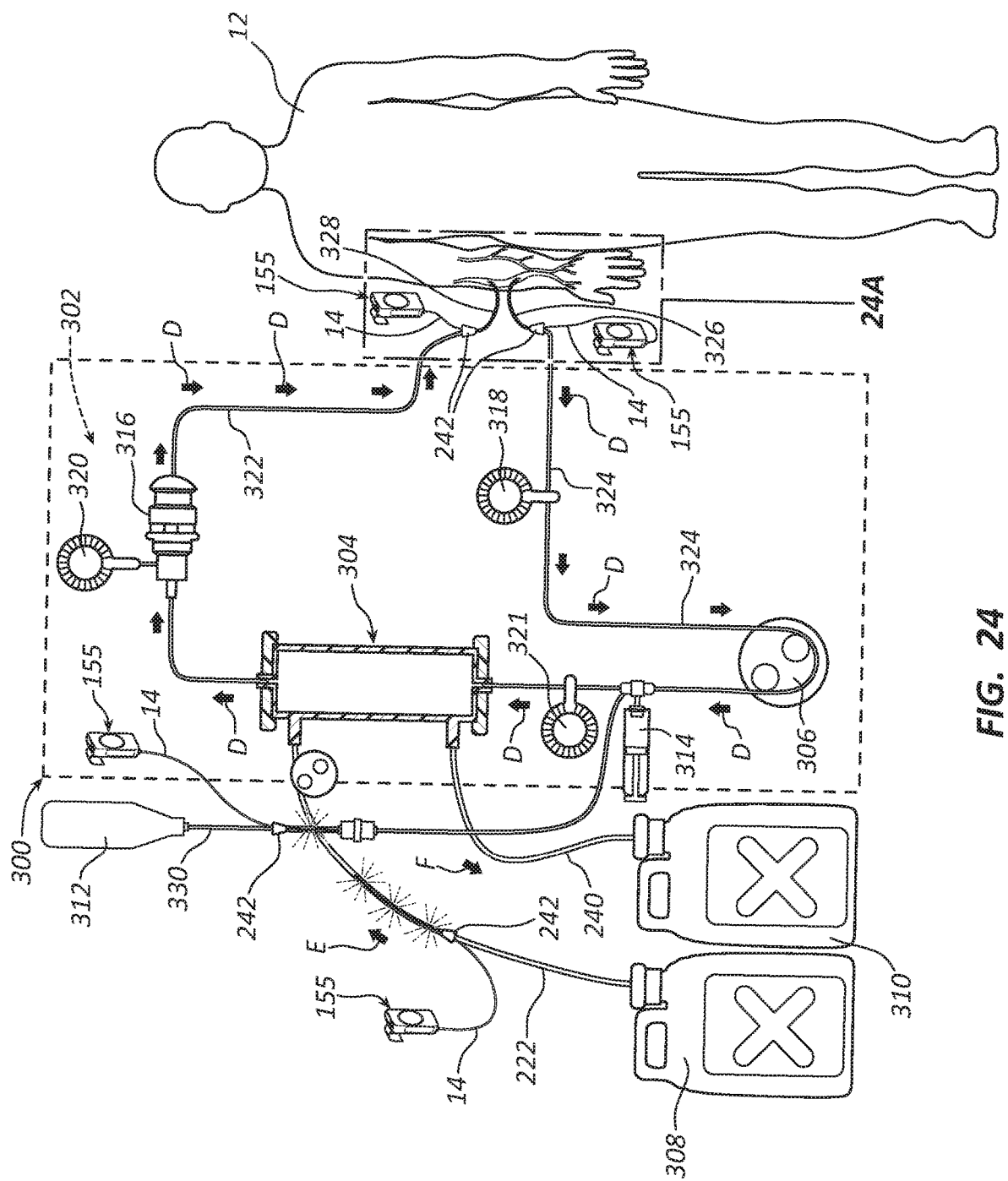
FIG. 24 is a schematic view of a representative exemplary embodiment of a hemodialysis system depicting a hemodialysis unit shown in phantom lines, components of the dialysis system pertinent to the invention of this disclosure, and an inset area enlarged as FIG. 24A.
Figure 24A:
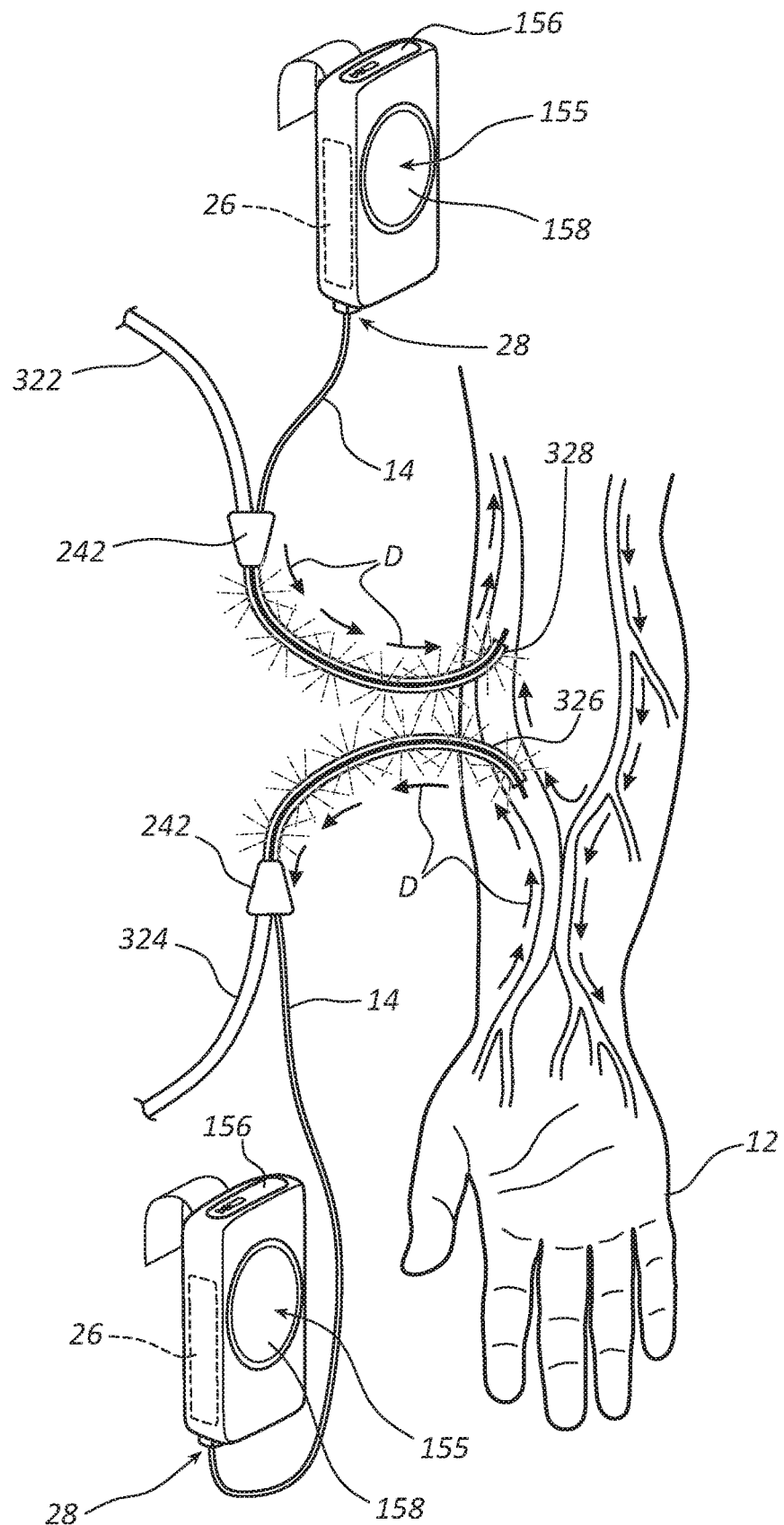
FIG. 24A is an enlargement of the inset area identified in FIG. 24 showing an exemplary dialysis access into the arm of a patient.

FIG. 24 is a schematic view of a representative exemplary embodiment of a hemodialysis system 300 depicting a hemodialysis unit 302 shown in phantom lines, components of the hemodialysis system 300 pertinent to the invention of this disclosure, and an inset area enlarged as FIG. 24A.

The components of the hemodialysis system 300 pertinent to the invention of this disclosure, include but are not limited to a dialysis access 201, a dialyzer 304, a blood pump 306, a dialysate reservoir 308, a waste dialysate reservoir 310, a saline bag 312, a heparin pump 314, an air trap/air detector 316, an arterial-pressure monitor 318, a venous-pressure monitor 320, an inflow-pressure monitor 321, an inbound blood flow tubing 322, and an outbound blood flow tubing 324. Some or most of these components may be enclosed within the hemodialysis unit 32. However, as depicted in FIG. 24, the dialysate reservoir 308, waste dialysate reservoir 310, and saline bag 312 are usually external to the hemodialysis unit and the dialysis access 201, being an access into the patient's body 12, is always outside the hemodialysis unit 302.

FIG. 24A is an enlargement of the inset area identified in FIG. 24 showing an exemplary dialysis access 201, a representative fistula access, into the patient's arm 12, showing an outbound venous line 326 and an inbound arterial line 328.

Blood from the patient 12 is drawn into the outbound venous line 326 and the outbound blood flow tubing 324 in the direction of Flow Arrows D, and is pumped into the dialyzer 304, where the blood is cleaned. A dialysate solution is drawn from the dialysate reservoir 308 into the dialyzer 304, in the direction of Inflow Arrow E, via a feed line 222 to interact with the venous-drawn blood, to filter it and remove waste and extra fluid from the blood, thereby serving as an artificial kidney. The cleaned, fresh blood exits the dialyzer 304 and flows (again in the direction of Flow Arrows D) into the inbound blood flow tubing 322 and then the inbound arterial line 328 to be circulated within the patient 12. The dialysate solution exiting the dialyzer 304 is waste dialysate 226 that carries out the waste, other impurities, and the extra fluid as it drains through the drainage line 240, in the direction of Drainage Arrow F, into the waste dialysate reservoir 310 for disposal.

As the filtered, fresh blood circulates through the patient's body 12, it gathers and collects waste, other impurities, and extra fluid before it again is drawn from the patient 12 into the outbound venous line 326 and the outbound blood flow tubing 324 in the direction of Flow Arrows D, and is pumped into the dialyzer 304 to be cleaned. The cycle of circulation through the patient's body 12 and the hemodialysis unit 302 continues to repeat until dialysis is complete.

During dialysis, the blood pump 306 regulates the flow of the blood through the hemodialysis unit. The heparin pump 314 infuses heparin into the blood to prevent the blood from clotting. A saline solution that flows from the saline bag 312 through a saline line 330 into the outbound blood flow tubing 324 (or, in some instances, directly into the dialyzer 304) is vital to the dialysis process. It is the saline solution in the dialyzer 304 that serves as the agent used to cleanse the venous-drawn blood within the dialyzer 304. The venous-pressure monitor 320 monitors the pressure within the outbound blood flow tubing 324 so that pressure may be maintained in an operable range. Additionally, the inflow-pressure monitor 321 monitors pressure at a location downstream of the blood pump 306 and upstream of the dialyzer so that the blood entering the dialyzer is within a proper operating range for the dialyzer 304. Similarly, the arterial-pressure monitor 318 monitors the pressure within the inbound blood flow tubing 322 so that pressure may be maintained in an operable range. The air trap/air detector 316 detects and traps undesirable air bubbles within the inbound blood flow tubing 322 before such air bubbles enter the patient's body 12 and cause serious consequences to the patient 12.

During preparations for dialysis and the actual hemodialysis process, there are occasions when either the patient 12 or a person assisting the patient may access or handle various connections, materials, or component parts involved in the dialysis. Such accessing or handling may introduce or enhance the possibility of infectious agents contaminating the hemodialysis equipment or process. Certain components can be identified as being particularly susceptible to such contamination. Consequently, being able to sterilize such components and/or to reduce or eliminate such infectious agents could reduce or eliminate one of the most serious concerns about having to undergo dialysis.

FIG. 24 depicts several representative locations where the delivery of therapeutic EMR could be instrumental in reducing or eliminating infections that are known to be pernicious to undergoing dialysis. Four separate EMR conduction systems 18 are depicted in FIG. 24 as representative locations for delivering therapeutic EMR. Although each of the locations depicted are shown as external to the hemodialysis unit 302 and as such may be retrofitted into an existing hemodialysis system 300, it should be understood that that one or more of the EMR conduction systems 18 may be disposed permanently within the hemodialysis unit 302. Also, although FIG. 24 depicts four separate EMR conduction systems 18 having four separate control devices 155, it should be understood that one, more than one, or all of the EMR conduction systems 18 may be operated by a single control device 155.

As depicted, one EMR conduction system 18 is placed to deliver EMR to sterilize the saline solution and/or the saline line 330 or inactivate infectious agents in the saline solution and/or on or in the saline line 330. This EMR conduction system 18 comprises a control device 155 that provides the EMR at the desired intensity(ies), an optical element 14 that receives and conveys the EMR from the control device 155 through an introducing adapter 238 into the saline line 330.

Another EMR conduction system 18 is placed to deliver EMR to sterilize the dialysate solution and/or the feed line 222 or inactivate infectious agents in the dialysate solution and/or on or in the feed line 222. This EMR conduction system 18 comprises a control device 155 that provides the EMR at the desired intensity(ies), an optical element 14 that receives and conveys the EMR from the control device 155 through an introducing adapter 238 into the feed line 222.

The other two EMR conduction systems 18 are used to deliver EMR to the representative dialysis access 201 are best depicted in FIG. 24A. The representative dialysis access 201 depicted is a fistula comprising an arterial access 342 and a venous access 344. The arterial access 342 and the venous access 344 comprises access needles (not shown) and the inbound blood flow tubing 322 and outbound blood flow tubing 324, respectively. One of the EMR conduction systems 18 is placed to deliver EMR to sterilize blood and/or the outbound blood flow tubing 324 or inactivate infectious agents in the blood and/or on or in the outbound blood flow tubing 324. The other EMR conduction system 18 is placed to deliver EMR to sterilize blood and/or the inbound blood flow tubing 322 or inactivate infectious agents in the blood and/or on or in the inbound blood flow tubing 322. Each EMR conduction system 18 comprises a control device 155 that provides the EMR at the desired intensity(ies), an optical element 14 that receives and conveys the EMR from the control device 155 through an introducing adapter 238 into the outbound blood flow tubing 324 and the inbound blood flow tubing 322, respectively.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Exemplary embodiments of the present invention are described above. No element, act, or instruction used in this description should be construed as important, necessary, critical, or essential to the invention unless explicitly described as such. Although several exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under Section 112, 6th paragraph is not intended. Additionally, it is not intended that the scope of patent protection afforded the present invention be defined by reading into any claim a limitation found herein that does not explicitly appear in the claim itself.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A medical device assembly for use with a dialysis system, the dialysis system having at least one fluid extension line disposed external to a patient's body and a dialysis access for insertion into the patient's body, the fluid extension line having at least one fluid lumen and the dialysis access having an elongate body and at least one internal lumen, the at least one fluid lumen and the at least one internal lumen being configured for delivery of a fluid to and/or retrieval of fluid from the patient's body, comprising:
   an electromagnetic radiation (EMR) source for providing non-ultraviolet, therapeutic EMR having an intensity comprising a radiant exposure of at least 0.1 J/cm$^2$ and up to 1.0 kJ/cm$^2$ and power of at least 0.005 mW and up to 1 Watt, such intensity being sufficient to produce a therapeutic effect of at least one of inactivating one or more infectious agents and enhancing healthy cell growth;
   an optical element conducive to the axial propagation of the therapeutic EMR relative to the elongate body of the dialysis access, the optical element having a position with respect to the dialysis access of being within at least one internal lumen of the dialysis access, at least a portion of the optical element comprises a fiber optic for disposition within the at least one internal lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the internal lumen of the dialysis access;
   at least one coupling to connect the EMR source to the optical element; and
   wherein the medical device assembly delivers through the at least one radial emission portion controlled relative intensity of the therapeutic EMR to produce a desired therapeutic effect in, on, or around the elongate body of the dialysis access while the dialysis access is disposed within the patient's body.

2. The medical device assembly as in claim 1 wherein the at least one radial emission portion of the fiber body is disposed at a position such that the emission of the therapeutic EMR radially from the fiber body is directed to a location for treatment region specific dosing of the therapeutic EMR.

3. The medical device assembly as in claim 1 wherein the optical element is removably insertable into the dialysis access.

4. The medical device assembly as in claim 1 wherein the dialysis access is selected from a group consisting of a central venous catheter, an arteriovenous fistula, an arteriovenous graft, a hemodialysis catheter, and a peritoneal catheter.

5. The medical device assembly as in claim 1 wherein the optical element also is conducive to the axial propagation of the therapeutic EMR relative to the fluid extension line, the optical element having a position with respect to the fluid extension line of being within at least one fluid lumen of the fluid extension line, at least a portion of the optical element comprises a fiber optic for disposition within the at least one fluid lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the fluid lumen of the fluid extension line.

6. The medical device assembly as in claim 1 further comprising a second optical element, the second optical element being conducive to the axial propagation of the therapeutic EMR relative to the fluid extension line, the second optical element having a position with respect to the fluid extension line of being within at least one fluid lumen of the fluid extension line, at least a portion of the optical element comprises a fiber optic for disposition within the at least one fluid lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the fluid lumen of the fluid extension line.

7. The medical device assembly as in claim 6 wherein the second optical element is removably insertable into the fluid extension line.

8. The medical device assembly as in claim 1 further comprising a second optical element, the second optical element being conducive to the axial propagation of the therapeutic EMR relative to the dialysis access, the second optical element having a position with respect to the dialysis access of being within at least one internal lumen of the dialysis access, at least a portion of the optical element comprises a fiber optic for disposition within the at least one internal lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the internal lumen of the dialysis access, the second optical element having at least one radial emission portion that differs from at least one radial emission portion of the optical element, and wherein the second optical element is removably insertable into the dialysis access and the second optical element is interchangeably insertable into the same internal lumen of the dialysis access.

9. The medical device assembly as in claim 1 wherein the dialysis access is a peritoneal dialysis catheter.

10. The medical device assembly as in claim 1 wherein the dialysis access is a hemodialysis catheter.

11. A medical device assembly for use in a dialysis system, at least a portion of the medical device assembly being insertable into a patient's body and being for delivery of a fluid to and/or retrieval of fluid from the patient's body, comprising:
   an electromagnetic radiation (EMR) source for providing non-ultraviolet, therapeutic EMR having an intensity comprising a radiant exposure of at least 0.1 J/cm$^2$ and up to 1.0 kJ/cm$^2$ and power of at least 0.005 mW and up to 1 Watt, such intensity being sufficient to produce a therapeutic effect of at least one of inactivating one or more infectious agents and enhancing healthy cell growth;

a dialysis access having an elongate body with at least one internal lumen, a coupling end and a distal end, the distal end being insertable into the patient's body, wherein the elongate body directs both the fluid and the therapeutic EMR axially relative to the dialysis access, axial flow of the fluid within the dialysis access facilitates at least one of delivery of fluid into the patient's body and retrieval of fluid from the patient's body, the dialysis access being selected from a group consisting of a central venous catheter, an arteriovenous fistula, an arteriovenous graft, a hemodialysis catheter, and a peritoneal catheter;

an optical element conducive to the axial propagation of the therapeutic EMR relative to the elongate body of the dialysis access, the optical element having a position with respect to the dialysis access of being within at least one internal lumen of the dialysis access, at least a portion of the optical element comprises a fiber optic for disposition within the at least one internal lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the internal lumen of the dialysis access;

at least one coupling to connect the EMR source to the optical element; and wherein at least one radial emission portion of the fiber body is disposed at a position such that the emission of the therapeutic EMR radially from the fiber body is directed to a location for treatment region specific dosing of the therapeutic EMR.

12. The medical device assembly as in claim 11 wherein the optical element is removably insertable into the dialysis access.

13. The medical device assembly as in claim 11 further comprising a fluid extension line having a fluid lumen, the optical element also being conducive to the axial propagation of the therapeutic EMR relative to the fluid extension line, the optical element having a position with respect to the fluid extension line of being within at least one fluid lumen of the fluid extension line, at least a portion of the optical element comprises a fiber optic for disposition within the at least one fluid lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the fluid lumen of the fluid extension line.

14. The medical device assembly as in claim 11 further comprising a second optical element, the second optical element being conducive to the axial propagation of the therapeutic EMR relative to the dialysis access, the second optical element having a position with respect to the dialysis access of being within at least one internal lumen of the dialysis access, at least a portion of the optical element comprises a fiber optic for disposition within the at least one internal lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the internal lumen of the dialysis access, the second optical element having at least one radial emission portion that differs from at least one radial emission portion of the optical element, and wherein the second optical element is removably insertable into the dialysis access and the second optical element is interchangeably insertable into the same internal lumen of the dialysis access.

15. The medical device assembly as in claim 11 further comprising a fluid extension line having a fluid lumen and a second optical element, the second optical element being conducive to the axial propagation of the therapeutic EMR relative to the fluid extension line, the second optical element having a position with respect to the fluid extension line of being within at least one fluid lumen of the fluid extension line, at least a portion of the optical element comprises a fiber optic for disposition within the at least one fluid lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the fluid lumen of the fluid extension line.

16. A medical device assembly for insertion into a peritoneal cavity of a patient's body and for delivery of a fluid to and/or retrieval of fluid from the patient's body, comprising:

an electromagnetic radiation (EMR) source for providing non-ultraviolet, therapeutic EMR having an intensity comprising a radiant exposure of at least 0.1 J/cm$^2$ and up to 1.0 kJ/cm$^2$ and power of at least 0.005 mW and up to 1 Watt, such intensity being sufficient to produce a therapeutic effect of inactivating one or more infectious agents;

a peritoneal dialysis catheter having an elongate catheter body with at least one internal lumen, a coupling end and a distal end, the distal end being insertable into the peritoneal cavity of the patient's body, wherein the catheter body directs both the fluid and the therapeutic EMR axially relative to the catheter body, axial flow of the fluid within the catheter body facilitates delivery of fluid into the patient's body and retrieval of fluid from the patient's body;

at least one fluid extension line external to the patient's body and having at least one fluid lumen;

an optical element conducive to the axial propagation of the therapeutic EMR relative to the peritoneal dialysis catheter body, the optical element having a position with respect to the peritoneal dialysis catheter body of being within at least one internal lumen of the peritoneal dialysis catheter body, at least a portion of the optical element comprises a fiber optic for disposition within the at least one internal lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the internal lumen of the peritoneal dialysis catheter;

at least one coupling to connect the EMR source to the optical element; and wherein at least one radial emission portion of the fiber body is disposed at a position such that the emission of the therapeutic EMR radially from the fiber body is directed to a location for treatment region specific dosing of the therapeutic EMR.

17. The medical device assembly as in claim 16 wherein at least a portion of the optical element is removably insertable into the internal lumen.

18. The medical device assembly as in claim 16 wherein the optical element also is conducive to the axial propagation of the therapeutic EMR relative to the fluid extension line, the optical element having a position with respect to the fluid extension line of being within at least one fluid lumen of the fluid extension line, at least a portion of the optical element comprises a fiber optic for disposition within the at least one fluid lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the fluid lumen of the fluid extension line.

19. The medical device assembly as in claim 16 further comprising a second optical element, the second optical element being conducive to the axial propagation of the therapeutic EMR relative to the peritoneal dialysis catheter, the second optical element having a position with respect to the peritoneal dialysis catheter of being within at least one internal lumen of the peritoneal dialysis catheter, at least a portion of the optical element comprises a fiber optic for disposition within the at least one internal lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the internal lumen of the peritoneal dialysis catheter, the second optical element having at least one radial emission portion that differs from at least one radial emission portion of the optical element, and wherein the second optical element is removably insertable into the peritoneal dialysis catheter and the second optical element is interchangeably insertable into the same internal lumen of the peritoneal dialysis catheter.

20. The medical device assembly as in claim 16 further comprising a second optical element, the second optical element being conducive to the axial propagation of the therapeutic EMR relative to the fluid extension line, the second optical element having a position with respect to the fluid extension line of being within at least one fluid lumen of the fluid extension line, at least a portion of the optical element comprises a fiber optic for disposition within the at least one fluid lumen, the fiber optic comprises a fiber body having an exterior surface, a coupling end, a distal end, and a core, the fiber optic being conducive to the axial propagation of therapeutic EMR within the core, the fiber optic further comprises at least one radial emission portion disposed between the coupling end of the fiber body and the distal end of the fiber body, the radial emission portion allowing the emission of therapeutic EMR radially from the fiber body into the fluid lumen of the fluid extension line.

* * * * *